US006737520B2

(12) United States Patent
Manoharan et al.

(10) Patent No.: US 6,737,520 B2
(45) Date of Patent: *May 18, 2004

(54) OLIGONUCLEOTIDES HAVING A-DNA FORM AND B-DNA FORM CONFORMATIONAL GEOMETRY

(75) Inventors: Muthiah Manoharan, Carlsbad, CA (US); Venkatraman Mohan, Carlsbad, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/098,816

(22) Filed: Mar. 15, 2002

(65) Prior Publication Data

US 2003/0105311 A1 Jun. 5, 2003

Related U.S. Application Data

(63) Continuation of application No. 09/303,586, filed on May 3, 1999, now Pat. No. 6,369,209.

(51) Int. Cl.$^7$ .......................... C07H 21/02; C07H 21/04
(52) U.S. Cl. ...................................... 536/23.1; 536/24.5
(58) Field of Search .............................. 536/23.1, 24.5

(56) References Cited

U.S. PATENT DOCUMENTS

| | | | |
|---|---|---|---|
| 3,687,808 A | 8/1972 | Merigan et al. | 195/28 |
| 4,689,320 A | 8/1987 | Kaji | 514/44 |
| 4,806,463 A | 2/1989 | Goodchild et al. | 435/5 |
| 5,004,810 A | 4/1991 | Draper | 536/27 |
| 5,166,195 A | 11/1992 | Ecker | 514/44 |
| 5,194,428 A | 3/1993 | Agrawal et al. | 514/44 |
| 5,212,295 A | 5/1993 | Cook | 536/26.7 |
| 5,242,906 A | 9/1993 | Pagano et al. | 514/44 |
| 5,248,670 A | 9/1993 | Draper et al. | 514/44 |
| 5,334,711 A | 8/1994 | Sproat et al. | 536/24.5 |
| 5,442,049 A | 8/1995 | Anderson et al. | 536/24.5 |
| 5,457,189 A | 10/1995 | Crooke et al. | 536/24.5 |
| 5,514,577 A | 5/1996 | Draper et al. | 435/238 |
| 5,514,788 A | 5/1996 | Bennett et al. | 536/23.1 |
| 5,523,389 A | 6/1996 | Ecker et al. | 536/23.1 |
| 5,580,767 A | 12/1996 | Cowsert et al. | 435/172.3 |
| 5,582,972 A | 12/1996 | Lima et al. | 435/6 |
| 5,582,986 A | 12/1996 | Monia et al. | 435/6 |
| 5,591,600 A | 1/1997 | Ecker | 435/69.1 |
| 5,591,623 A | 1/1997 | Bennett et al. | 435/240.2 |
| 5,591,720 A | 1/1997 | Anderson et al. | 514/44 |
| 5,607,923 A | 3/1997 | Cook et al. | 514/44 |
| 5,620,963 A | 4/1997 | Cook et al. | 514/44 |
| 5,639,649 A | 6/1997 | Almond et al. | 435/235.1 |
| 5,658,891 A | 8/1997 | Draper et al. | 514/44 |
| 5,661,134 A | 8/1997 | Cook et al. | 514/44 |
| 5,681,747 A | 10/1997 | Boggs et al. | 435/375 |
| 5,681,944 A | 10/1997 | Crooke et al. | 536/24.5 |
| 5,877,309 A | 3/1999 | McKay et al. | 536/24.5 |

FOREIGN PATENT DOCUMENTS

| | | |
|---|---|---|
| WO | WO 89/12060 | 12/1989 |
| WO | WO 92/03568 | 3/1992 |
| WO | WO 94/08003 | 4/1994 |

OTHER PUBLICATIONS

Cheatham et al., Molecular Dynamics Simulations Highlight the Structural Differences Among DNA:DNA, RNA:RNA and DNA:RNA Hybrid Duplexes, J. American Chem. Soc. vol. 119, No. 21 (1997).*

U.S. patent application Ser. No. 08/837,201, Dean et al., filed Mar. 14, 1997.

U.S. patent application Ser. No. 09/009,490, Bennett et al., filed Jan. 20, 1998.

U.S. patent application Ser. No. 09/044,506, Bennett et al., filed Mar. 19, 1998.

U.S. patent application Ser. No. 09/062,416, Bennett et al., filed Apr. 17, 1998.

Abe, A. et al., "Conformational Energies and the Random–Coil Dimensions and Dipole Moments of Polyoxides CH3O[(CH2)]yOxCH3," *J. Am. Chem. Soc.*, 1976, 6468–6476.

Albert, P.R. et al., "Antisense knockouts: molecular scalpels for the dissection of signal transduction", *Trends Pharmacol. Sci.*, 1994, 15, 250–254.

Altmann, K. et al., "Second Generation Antisense Oligonucleotides–Inhibition of Pkc–1 And c–RAF Kinase Expression by Chimeric Oligonucleotides Incorporating 6–Substituted Carbocyclic Nucleosides and 2'–Ethylene Glycol Substituted Ribonucleosides," *Nucleosides & Nucleotides*, 1997, 16(7–9), 917–926.

Altmann, K. et al., "Second–Generation Antisense Oligonucleotides: Structure–Activity Relationships and the Design of Improved Signal–Transduction Inhibitors", *Biochem. Soc. Trans.*, 1996, 24, 630–637.

Altmann, K. et al., "Second Generation of Antisense Oligonucleotides: From Nuclease Resistance to Biological Efficacy in Animals," *Chimia*, 1996, 50, 168–176.

(List continued on next page.)

*Primary Examiner*—James O. Wilson
*Assistant Examiner*—Traviss C. McIntosh, III
(74) *Attorney, Agent, or Firm*—Woodcock Washburn LLP

(57) ABSTRACT

Modified oligonucleotides containing both A-form conformation geometry and B-from conformation geometry nucleotides are disclosed. The B-form geometry allows the oligonucleotide to serve as substrates for RNase H when bound to a target nucleic acid strand. The A-form geometry imparts properties to the oligonucleotide that modulate binding affinity and nuclease resistance. By utilizing C2' endo sugars or O4' endo sugars, the B-form characteristics are imparted to a portion of the oligonucleotide. The A-form characteristics are imparted via use of either 2'-O-modified nucleotides that have 3' endo geometries or use of end caps having particular nuclease stability or by use of both of these in conjunction with each other.

38 Claims, 9 Drawing Sheets

OTHER PUBLICATIONS

Baker, B.F. et al., "2'-O-(2-Methoxy)ethyl-modified Anti-intercellular Adhesion Molecule 1 (ICAM-1) Oligonucleotides Selectively Increase the ICAM-1 Translation Initiation Complex in Human Umbilical Vein Endothelial Cells", *J. Biol. Chem.*, 1997, 272, 11994–12000.

Beal, P. A. et al., "Second Structural Motif for Recognition of DNA by Oligonucleotide–Directed Triple–Helix Formation," *Science*, 1991, 251, 1360–1363.

Beaucage, S.L. et al., "Advances in the Synthesis of Oligonucleotides by the Phosphoramidite Approach", *Tetrahedron*, 1992, 48, 2223–2311.

Berger et al., "Crystal structures of B–DNA with incorporated 2'-deoxy-2'fluoro-arabino-furanosyl thymines: implications of conformational preorganization for duplex stability," *Nucl. Acids Res.*, 1998, 26(10), 2473–2480.

Berkow et al. (eds.), *The Merck Manual of Diagnosis and Therapy*, 15th Edition, Rahway, N.J., 1987, 2263–2277.

Berkow et al. (eds.), *The Merck Manual of Diagnosis and Therapy*, 15th Edition, Rahway, N.J., 1987, 2283–2287.

Berkow et al. (eds.), *The Merck Manual of Diagnosis and Therapy*, 15th Edition, Rahway, N.J., 1987, 2286–2293.

Berkow et al. (eds.), *The Merck Manual of Diagnosis and Therapy*, 15$^{th}$ Edition, Rahway, NJ, 1987, 2301–2310.

Bernhard, E.J. et al., "Direct Evidence Linking Expression of Matrix Metalloproteinase 9 (92-kDa gelatinase/collagenase) to the metastatic phenotype in transformed rat embryo cells," *Proc. Natl. Acad. Sci. USA*, 1994, 91, 4293–4297.

Birkedal–Hansen, H. et al., "Proteolytic Remodeling of Extracellular Matrix," *Curr. Op. Cell Biol.*, 1995, 7, 728–735.

Bock, L. C. et al., "Selection of Single-Stranded DNA Molecules that Bind and Inhibit Human Thrombin,"*Nature*, 1992, 355, 564–566.

Böggemeyer, E. et al., "Borrelia Burgdorferi Upregulates the Adhesion Molecules E–selectin, P–selectin, ICAM–1 and VCAM–1 on Mouse Endothelioma Cells in vitro," *Cell Adhes. Commun.*, 1994, 2, 145–157.

Conte, M. R. "Confirmational Properties and Thermodynamics of the RNA Duplex r(CGCAAAUUUGCG)2: Comparison with the DNA Analogue d(CGCAAATTTGCG)2," *Nucl. Acids Res.*, 1997, 25(13), 2627–2634.

Cornell, W. D. et al., "A Second Generation Force Field for the Simulation of Proteins, Nucleic Acids, and Organic Molecules," *J. Am. Chem. Soc.*, 1995, 117, 5179–5197.

Cory, A.H. et al., "2'-Deoxy-2'-Methylene Derivatives of Adenosine, Guanosine, Tubercidin, Cytidine and Uridine as Inhibitors of L1210 Cell Growth in Culture," *Biochem. Pharmacol.*, 1994, 47(2), 365–371.

Cowsert, L. M. et al., "In vitro and In Vivo Activity of Antisense Inhibitors of ras: Potential for Clinical Development," *Anti–Cancer Drug Design*, 1997, 12, 359–371.

Crooke, S.T. et al., "Pharmacokinetic Properties of Several Novel Oligonucleotide Analogs in mice", *J. Pharmacol. Exp. Therapeutics*, 1996, 277, 923–937.

Crooke, S.T. et al., "Kinetic characteristics of *Escherichia coli* RNase H1: cleavage of various antisense oligonucleotide–RNA duplexes", *Biochem. J.*, 1995, 312, 599–608.

Crooke, S. T., "Progress in Antisense Therapeutics," *Medicinal Research Reviews*, 1996, 16(4), 319–344.

Damha, M.J. et al., "An improved procedure for derivatization of controlled-pore glass beads for solid-phase oligonucleotide synthesis", *Nucl. Acids Res.*, 1990, 18, 3813–3821.

Damha et al., "Hybrids of RNA and Arabinonucleic Acids (ANA and 2'F–ANA) Are Substrates of Ribonuclease H," *J. Am. Chem. Soc.*, 1998, 120, 12976–12977.

De Mesmaeker, A. et al., "Antisense Oligonucleotides",*Acc. Chem. Res.*, 1995, 28, 366–374.

Dean, N.M. et al., "Inhibition of protein kinase C–α expression in mice after systemic administration of phosphorthioate antisense oligodeoxynucleotides", *Proc. Natl. Acad. Sci.*, 1994, 91, 11762–11766.

DeLisser, H. M. et al., "Molecular and Functional Aspects of PECAM–1/CD31," *Immunol. Today*, 1994, 15(10), 490–494.

Dimock, S. et al., "An Efficient Multigram Synthesis of Monomers for the Preparation of Novel Oligonucleotides Containing Isosteric Non–Phosphorous Backbones," *Nucleosides & Nucleotides*, 1997, 16(7–9), 1629–1632.

Downward, J. et al., "The ras Superfamily of Small GTP–binding proteins," *TIBS*, 15, 1990, 469–472.

Egli, M. et al., "RNA Hydration: A Detailed Look," *Biochemistry*, 1996, 35, 8489–8494.

Englisch, U. et al., "Chemically Modified Oligonucleotides as Probes and Inhibitors",*Angew. Chem. Int. Ed. Eng.*, 1991, 30, 613–629.

Fedoroff, O. Y. et al., "Structure of a DNA: RNA Hybrid Duplex Why Rnase H Does Not Cleave Pure RNA," *J. Mol. Biol.*, 1993, 233, 509–523.

Flanagan et al., "Cellular penetration and antisense activity by a phenoxazine–substituted heptanucleotide," *Nat. Biotechnol.*, 1999, 17(1), 48–52.

Fraser, A. et al., "Synthesis and Conformational Properties of 2'-Deoxy-2'-methylthio-pyrimidine and -purine Nucleosides: Potential Antisense Applications," *J. Heterocycl. Chem.*, 1993, 30, 1277–1287.

Freier, S.M. et al., "The ups and downs of nucleic acid duplex stability: structure–stability studies on chemically–modified DNA:RNA duplexes", *Nucl. Acids Res.*, 1997, 25, 4429–4443.

Gaffney, B.L. et al., "A New Strategy for the Protection of Deoxyguanosine During Oligonucleotide Synthesis", *Tetrahedron Letts.*, 1982, 23, 2257–2260.

Gao, Y–G. et al., "Molecular Structure of a DNA Decamer Containing an Anticancer Nucleoside Arabinosylcytosine: Conformational Pereturbation by Arabinosylcytosine in B–DNA," *Biochem.*, 1991, 30(41), 9922–9931.

Gmeiner, W.H. et al., "Effect of Cytarabine on the NMR Structure of a Model Okazaki Fragment from the SV40 Genome," *Biochem.*, 1999, 38, 1166–1175.

Gonzalez, C. et al., "Structure and Dynamics of a DNA–RNA Hybrid Duplex with a Chral Phosphorothioate Moiety: NMR and Molecular Dynamics with Conventional and Time–Averaged Restraints," *Biochemistry*, 1995, 34, 4969–4982.

Gotfredsen, C.H. et al., "Novel Oligodeoxynucleotide Analogues Containing A 2'-O–Methylarabinonucleoside," *Tetra. Lett.*, 1994, 35(37), 6941–6944.

Gotfredsen, C.H. et al., "Synthesis and Properties of α– and β–Oligodeoxynurleotides Containing α– and β–1–(2–O–Methy–D–arabino–furanosyl)thymine," *Bioorg. Med. Chem.*, 1996, 4(8), 1217–1225.

Gotfredsen, C.H. et al., "Structure of a DNA Duplex Containing a Single 2'-O–Methyl–β–D–araT: Combined Use of NMR, Restrained Molecular Dynamics, and Full Relaxation Matrix Refinement," *Bioconjugate Chem.*, 1996, 7, 680–688.

Griffin, L. C. et al., "In Vivo Anticoagulant Properties of a Novel Nucleotide–Based Thrombin Inhibitor and Demonstration of Regional Anticoagulation in Extracorporeal Circuits," *Blood*, 1993, 81, 3271–3276.

Griffiths, C.E.M. et al., "Keratinocyte Intercellular Adhesion Molecule–1 (ICAM–1) Expression Preceeds Derman T Lymphocyte Infiltration in Allergic Contact Dermatitis (*Rhus dermatitis*)", *Am. J. Pathology.*, 1989, 135, 1045–1053.

Gum, R. et al., "Stimulation of 92–kDa Gelatinase B Promoter Activity by ras Is Mitogen–activated Protein Kinase Kinase 1–independent and Requires Multiple Transcription Factor Binding Sites Including Closely Spaced PEA3/ets and AP–1 Sequences," *J. Biol. Chem.*, 1996, 271(18), 10672–10680.

Guzaev A. et al., "Synthesis of C–Radiolabeled Oligonucleotides with a Novel Phosphoramidite Reagent," *Bioorg. & Med. Chem. Lett.*, 1998, 8, 1123–1126.

Hakugawa, J. et al., "The Inhibitory Effect of Anti–Adhesion Molecule Antibodies on Eosinophil Infilration in Cutaneous Late Phase Response in Balb/c Mice Sensitized with Ovalbumin (OVA)," *J. Dermatol.*, 1997, 24, 73–79.

Hansske, F. et al., "2' and 3'–Ketonucleosides and their *Arabino* and *Xylo* Reduction Products", *Tetrahedron*, 1984, 40, 125–135.

Hansske et al., "Nucleic Acid Related Compounds. 43. A Convenient Procedure for the Synthesis of 2' and 3'–Ketonucleosides," *Tetra. Lett.*, 1983, 24(15), 1589–1592.

Hegemann, L. et al., "Biochemical Pharmacology of Protein Kinase C and its Relevance for Dermatology", *Pharmacology of the Skin*, 1992, Ch. 22, CRC Press, Boca Raton, 357–368.

Himelstein, B. P. et al., "Metalloproteinases in Tumor Progression: The Contribution of MMP–9," *Invasion & Metastasis*, 1994–95, 14, 246–258.

Ho, V.C. et al., "Treatment of severe lichen planus with cyclosporine", *J. Am. Acad. Dermatol.*, 1990, 22, 64–68.

Horton, N. C. et al., "The Structure of an RNA/DNA Hybrid: A Substrate of the Ribonuclease Activity of HIV–1 Reverse Transcriptase," *J. Mol. Biol.*, 1996, 264, 521–533.

Hua, J. et al., "Inhibition of Matrix Metalloproteinase 9 Expression by a Ribozyme Blocks Metastasis in a Rat Sarcoma Model System," *Cancer Res.*, 1996, 56, 5279–5284.

Hurtenbach, U. et al., "Prednisolone Reduces Experimental Arthritis and Inflammatory Tissue Destruction in Scid Mice Infected with Borrelia Burgdorferi," *Int. J. Immunopharmac*, 1996, 18, 281–288.

Iribarren, A.M. et al., "Resistance to Degradation by Nucleases of (2'S)–2'–Deoxy–2'–C–methyloligonucleotides, Novel Potential Antisense Probes," *Antisense Res. Dev.*, 1994, 4(2), 95–98.

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.*, 1990, 55, 4693–4699.

Jaishree, T.N. et al., "Structural Influence of RNA Incorporation in DNA: Quantitative Nuclear Magnetic Resonance Refinement of d(CG)r(CG)d(CG) and d(CG)r(C)d-(TAGCG)," *Biochem.*, 1993, 32, 4903–4911.

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Katocs, A.S. et al., "Biological Testing", *Remington's Pharmaceutical Sciences*, 18th Ed., Gennaro (ed.), Mack Publishing Co., Easton, PA, 1990, Ch. 27, 484–494.

Kerr, L. D. et al., "TGF–β1 Inhibition of Transin/Stromelysin Gene Expression Is Mediated Through a Fos Binding Sequence," *Cell*, 1990, 61, 267–278.

Kerr, L. D. et al., "Growth Factors Regulate Transin Gene Expression by c–fos–Dependent and c–fos–Independent Pathways," *Science*, 1988, 242, 1424–1427.

Kois, P. et al., "Synthesis and Some Properties of Modified Oligonucleotides. 2. Oligonucleotides Containing 2'–Deoxy–2'–Fluoro–β–D–Arabinofuranosyl Pyrimidine Nucleosides," *Nucleosides Nucleotides*, 1993, 12(10), 1093–1109.

Kroschwitz, J.I., "Polynucleotides", *Concise Encyclopedia of Polymer Science and Engineering*, 1990, John Wiley & Sons, New York, 858–859.

Lane, A. N. et al., "NMR Assignments and Solution Conformation of the DNA–RNA Hybrid Duplex d(GTGAACT-T)–r(AAGUUCAC)," *Eur. J. Biochem.*, 1993, 215, 297–306.

Lesnik, E.A. et al., "Oligodeoxynucleotides Containing 2'–O–Modified Adenosine" Synthesis and Effects on Stability of DNA:RNA Duplexes, *Biochem.*, 1993, 32, 7832–7838.

Lesnik, E. A. et al., "Relative Thermodynamic Stability of DNA, RNA, and DNA: RNA Hybrid Duplexes: Relationship with Base Composition and Structure," *Biochemistry*, 1995, 34(34), 10807–10815.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*,1989, 86, 6553–6556.

Lima et al., "Binding Affinity and Specificity of *Escherichia coli* RNase H1: Impact on the Kinetics of Catalysis of Antisense Oligonucleotide—RNA Hybrids," *Biochemistry*, 1997, 36, 390–398.

Lin et al., "A Cytosine Analogue Capable of Clamp–Like Binding to a Guanine in Helical Nucleic Acids," *J. Am. Chem. Soc.*, 1998, 120, 8531–8532.

Lisby, S. et al., "Intercellular adhesion molecule–1 (ICAM–1) expression correlated to inflammation", *Br. J. Dermatol.*, 1989, 120, 479–484.

Litwin, M. et al., "Novel Cytokine–independent Induction of Endothelial Adhesion Molecules Regulated by Platelet/Endothelial Cell Adhesion Molecule (CD31),"*J. Cell Biol.*, 1997, 139(1), 219–228.

Manoharan, M. et al., "Lipidic Nucleic Acids", *Tetrahedron Letts.*, 1995, 36, 3651–3654.

Manoharan M. et al., "Oligonucleotide Conjugates: Alteration of the Pharmacokinetic Properties of Antisense Agents", *Nucleosides and Nucleotides*, 1995, 14, 969–973.

Manoharan, M. et al., "Chemical Modifications to Improve Uptake and Bioavailability of Antisense Oligonucleotides", *Annals NY Acad. Sciences*, 1992, 660, 306–309.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan M. et al., "Cholic Acid–Oligonucliotide Conjugates for Antisense Applications", *Bioorganic Med. Chem. Letts.*, 1994, 4, 1053–1060.

Martin, P., "Ein neuer Zugang zu 2'–O–Alkylribonucleosiden und Eigenschaften deren Oligonucleotide", *Helvetica Chemica Acta*, 1995, 78, 486–504.

Matsuda, A. et al., "Nucleosides and Nucleotides. 97. Synthesis of New Broad Spectrum Antineoplastic Nucleosides, 2'–Deoxy–2'–methylidenecytidine (DMDC) and Its Derivatives," *J. Med. Chem.*, 1991, 34, 812–819.

Miller, P.S. et al., "A New approach to chemotherapy based on molecular biology and nucleic acid chemistry: Matagen (masking tape for gene expression)", *Anti–Cancer Drug Des.*, 1987, 2, 117–128.

Milligan, J. F. et al., "Current Concepts in Antisense Drug Design," *J. Med. Chem.*, 1993, 36(14), 1923–1937.

Mishra, R.K. et al., "Improved leishmanicidal effect of phosphorotioate antisense oligonucleotides by LDL–medicated delivery", *Biochim. et Biophysica*, 1995, 1264, 229–237.

Monia, B.P. et al., "Sequence–specific Antitumor Activity of a Phosphorothioate Oligodeoxyribonucleotide Targeted to Human C–raf Kinase Supports an Antisense Mechanism of Action In Vivo," *Proc. Natl. Acad. Sci. USA*, 1996, 93, 15481–15483.

Newman, P. J. et al., "Perspective Series: Cell Adhesion in Vascular Biology," *Biology PECAM–1, J. Clin. Invest.*, 1997, 99(1), 3–7.

Nies, A.S. et al., "Principles of Therapeutics", *Goodman & Gilman's The Pharmacological Basis of Therapeutics*, 9th Ed., Hardman et al. (eds.), McGraw–Hill, New York, NY, 1996, Ch. 3, 43–62.

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.

Obika et al., "Preparation and Properties of 2',5'–Linked Oligonucleotide Analogues Containing 3'–O, 4'–C–Methyleneribonucleosides," *Bioorg. Med. Chem. Lett.*, 1999, 9, 515–518.

Pon, R.T., "Solid Phase Supports for Oligonucleotide Synthesis", *Methods in Molecular Biology*, vol. 20, *Protocols for Oligonucleotides and Analogs*, Agrawal, S. (ed.), Human Press, Totowa, NJ, 1993, Chapter 19, 465–496.

Regezi, J. A. et al., "Vascular Adhesion Molecules in Oral Lichen Planus," *Oral Surg. Oral Med. Oral Pathol.*, 1996, 81, 682–690.

Resmini, M. et al., "Synthesis of an Arabinonucleic Acid (tANA)," *Bioorg. Med. Chem. Lett.*, 1994, 4(16), 1909–1912.

Resmini, M. et al., "38. Nucleosides: Part LV: Efficient Synthesis of Arabinoguanosine Building Blocks," *Helv. Chim. Acta*, 1994, 77, 429–434.

Resmini et al., "9. Nucleotides: Part XXXIX: Synthesis of Arabinonucleoside Phosphoramidite Building Blocks," *Helv. Chim. Acta*, 1993, 76, 158–167.

Roberts, D. D. et al., "Neighboring Methoxy Group Effect in Solvolysis Reactions of Cyclopentyl and Cyclohexyl p–Toluenesulfonates," *J. Org. Chem.*, 1997, 62, 1857–1859.

Roberts, D. D. et al., "Neighboring–Group Study in Solvolyses of Cyclopentyl and Cyclohexyl Tosylates," *Cyclopentyl and Cyclohexyl Toslates*, 1969, 34(8), 2415–2417.

Robins, M.J. et al., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides", *J. Am. Chem. Soc.*, 1983, 105, 4059–4065.

Rosenthal et al., "Nucleosides of Branched–Chain Nitromethyl, Cyanomethyl, and Aminomethyol Sugars," *Tetra. Lett.*, 1970, 48, 4233–4235.

Ruoslahti, E., "How Cancer Spreads," *Sci. Am.*, 1996, 72–77.

Saison–Behmoaras, T. et al., "Short modified antisense oligonucleotides directed against Ha–*ras* point mutation induce selective cleavage of the mRNA and inhibit T24 cells proliferation", *EMBO J.*, 1991, 10, 1111–1118.

Sanghvi, Y.S. et al., "Concept, Discovery and Development of MMI Linkage: Story of a Novel Linkage for Antisense Constructs," *Nucleosides & Nucleotides*, 1997, 16(7–9), 907–916.

Schmit, C. et al., "The Effects of 2'– and 3'–Alkyl Substituents on Oligonucleotide Hybridization and Stability," *Bioorg. Med. Chem. Lett.*, 1994, 4(16), 1969–1974.

Schweitzer, B.I. et al., "Solution Structure of a DNA Dodecamere Containing the Anti–Neoplastic Agent Arabinosylcytosine: Combined Use of NMR, Restrained Molecular Dynamics, and Full Relaxation Matrix Refinement," *Biochem.*, 1994, 33(38), 11460–11475.

Searle, M. S. et al., "On the Stability of Nucleic Acid Structures in Solution: Enthalpy–Entropy Compensations, Internal Rotations and Reversibility," *Nucl. Acids Res.*, 1993, 21(9), 2051–2056.

Seela, F. et al., "Palindromic Octa–and Dodecanucleotides Containing 2'–Deoxytubercidin: Synthesis, Hairpin Formation, and Recognition by the Endodeoxyribonuclease *Eco*RI", *Biochemistry*, 1987, 26, 2232–2238.

Shea, R.G. et al., "Synthesis, hybridization properties and antiviral activity of lipid–oligodeoxynucleotide conjugates", *Nucl. Acids Res.*, 1990, 18, 3777–3783.

Shiohara et al., "Fixed drug Eruption: Expression of Epidermal Keratinocyte Intercellular Adhesion Molecule–1 (ICAM–1)", *Arch. Dermatol.*, 1989, 125, 1371–1376.

Stein, C.A. et al., "Oligodeoxynucleotides as Inhibitors of Gene Expression: A Review", *Cancer Res.*, 1988, 48, 2659–2668.

Stetler–Stevenson, W.G. et al., "Tumor Cell Interactions with the Extracellular Matrix During Invasion and Metastasis," *Annu. Rev. Cell Biol.*, Palade, G.E. et al. (eds.), 1993, 9, 541–573.

Svinarchuk, F.P. et al., "Inhibition of HIV proliferation in MT–4 cells by antisense oligonucleotide conjugated to lipophilic groups", *Biochimie*, 1993, 79, 49–54.

Swayze, E. E. et al., "The Synthesis of N,N'–O–Trisubstituted Hydroxylamines via a Mild Reductive Alkylation Procedure: An Improved Synthesis of the MMI Backbone," *Synlett*, 1997, 859–861.

Swayze, E. E. et al., "The Synthesis of the Sixteen Possible 2'–O–Methyl MMI Dimer Phosphoramidites: Building Blocks for the Synthesis of Novel Antisense Oligonucleotides," *Nucleosides & Nucleotides*, 1997, 16(7–9), 971–972.

U.S. Congress, Office of Technology Assessment, "The State–of–the–art in Genetic Screening", *Genetic Monitoring and Screening in the Workplace*, OTA–BA–455, U.S. Government Printing Office, Washington, D.C., 1990, Ch. 5, 75–99.

Uhlmann, E. et al., "Antisense Oligonucleotides: A New Therapeutic Principle", *Chem. Reviews*, 1990, 90, 543–584.

Wagner, D. et al., "Preparation and Synthesis Utility of Some Organotin Derivatives of Nucleosides", *J. Org. Chem.*, 1974, 39, 24–30.

Wagner, R. W. et al., "Antisense Gene Inhibition by Oligonucleotides Containing C–5 Propyne Pyrimidines," *Science*, 1993, 260, 1510–1513.

Wahlestedt, C. et al., "Modulation of Anxiety and Neuropeptide Y–Y1 Receptors by Antisense Oligodeoxynucleotides", *Science*, 1993, 259, 528–531.

Wahlestedt, C. et al., "Antisense oligodeoxynucleotides to NMDA–R1 receptor channel protect cortical neurons from excitotoxicity and reduce focal ischaemic infarctions", *Nature*, 1993, 363, 260–263.

Wilds, C.J. et al., "Duplex Recognition by Oligonucleotides Containing 2'–Deoxy–2'–fluoro–D–arabinose and 2'–Deoxy–2'–fluoro–D–ribose. Intermolecular 2'–OH–Phosphate Contacts versus Sugar Puckering in the Stabilization of Triple–Helical Complexes," *Bioconjugate Chem.*, 1999, 10, 299–305.

Wolfe, S., "The Gauche Effect. Some Stereochemical Consequences of Adjacent Electron Pairs and Polar Bonds," *Accounts of Chemical Research*, 1972, 5, 102–110.

Young, S. L. et al., "Triple Helix Formation Inhibits Transcription Elongation In Vitro," *Proc. Natl. Acad. Sci. USA*, 1991, 88, 10023–10026.

Zhang, H. et al., "Conformational Perturbation of the Anticancer Nucleoside Arabinosylcytosine on Z–DNA: Molecular Structure of $(araC-dG)_3$ at 1.3 Å Resolution," *Biopolymers*, 1992, 32, 1559–1569.

Ausubel, F.M. et al., et al., in *Current Protocols in Molecular Biology*, John Wiley, New York, 1989.

Cohen in *Oligonucleotides: Antisense Inhibitors of Gene Expression*, CRC Press, Inc., Boca Raton, FL, 1989.

Sambrook, J. et al., *Molecular Cloning: A Laboratory Manual*, Cold Spring Harbor Labortory Press, 1989.

Sanger et al., *Principles of Nucleic Acid Structure*, Springer–Verlag, New York, NY, 1984.

Nishizaki, et al., *Biochemistry*, 1996, 35(13), 4016–4025.

\* cited by examiner

INCREASES IN VIVO STABILITY

IN MOUSE LIVER AFTER 24h

IN MOUSE KIDNEY AFTER 24h

A 11061 (P=S)

A

B 17179 3'−MOE, 2'−5' P=S at 5' end

B

C 17180 2'−5' P=S at each end

C

D 17181 P=S Core 2'−5' P=O at each end

D

OLIGONUCLEOTIDES HAVING A-DNA FORM AND B-DNA FORM CONFORMATIONAL GEOMETRY

CROSS-REFERENCE TO RELATED APPLICATIONS

This application is a continuation of patent application Ser. No. 09/303,586, filed May 3, 1999 now U.S. Pat. No. 6,369,209, which is hereby incorporated by reference in its entirety.

FIELD OF THE INVENTION

The present invention relates to oligonucleotides that have both A-form and B-form conformational geometry and methods of using such oligonucleotides. The oligonucleotides of the invention are useful in therapeutic and investigative purposes. More specifically, the present invention is directed to oligonucleotides having particular modifications that will increase affinity and nuclease resistance while concurrently serving as substrates for RNase H when bound to a target RNA strand.

BACKGROUND OF THE INVENTION

It is well known that most of the bodily states in mammals, including most disease states, are affected by proteins. Classical therapeutic modes have generally focused on interactions with such proteins in an effort to moderate their disease-causing or disease-potentiating functions. However, recently, attempts have been made to moderate the actual production of such proteins by interactions with molecules that direct their synthesis, such as intracellular RNA. By interfering with the production of proteins, maximum therapeutic effect and minimal side effects may be realized. It is the general object of such therapeutic approaches to interfere with or otherwise modulate gene expression leading to undesired protein formation.

One method for inhibiting specific gene expression is the use of oligonucleotides. Oligonucleotides are now accepted as therapeutic agents. A first such oligonucleotide has been approved for human therapeutic use by the FDA and is available in commercial marketplace.

Oligonucleotides are known to hybridize to single-stranded DNA or RNA molecules. Hybridization is the sequence-specific base pair hydrogen bonding of nucleobases of the oligonucleotide to the nucleobases of the target DNA or RNA molecule. Such nucleobase pairs are said to be complementary to one another. The concept of inhibiting gene expression through the use of sequence-specific binding of oligonucleotides to target RNA sequences, also known as antisense inhibition, has been demonstrated in a variety of systems, including living cells (for example see: Wagner et al., Science (1993) 260: 1510–1513; Milligan et al., *J. Med. Chem.,* (1993) 36:1923–37; Uhlmann et al., *Chem. Reviews,* (1990) 90:543–584; Stein et al., *Cancer Res.,* (1988) 48:2659–2668).

The events that provide the disruption of the nucleic acid function by antisense oligonucleotides (Cohen in *Oligonucleotides: Antisense Inhibitors of Gene Expression,* (1989) CRC Press, Inc., Boca Raton, Fla.) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides: Miller, P. S. and Ts'O, P. O. P. (1987) *Anti-Cancer Drug Design,* 2:117–128, and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are probably the most prominent example of an antisense agent that operates by this type of antisense terminating event.

Oligonucleotides may also bind to duplex nucleic acids to form triplex complexes in a sequence specific manner via Hoogsteen base pairing (Beal et al., *Science,* (1991) 251:1360–1363; Young et al., *Proc. Natl. Acad. Sci.* (1991) 88:10023–10026). Both antisense and triple helix therapeutic strategies are directed towards nucleic acid sequences that are involved in or responsible for establishing or maintaining disease conditions. Such target nucleic acid sequences may be found in the genomes of pathogenic organisms including bacteria, yeasts, fungi, protozoa, parasites, viruses, or may be endogenous in nature. By hybridizing to and modifying the expression of a gene important for the establishment, maintenance or elimination of a disease condition, the corresponding condition may be cured, prevented or ameliorated.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides may also be of therapeutic value when they bind to non-nucleic acid biomolecules such as intracellular or extracellular polypeptides, proteins, or enzymes. Such oligonucleotides are often referred to as 'aptamers' and they typically bind to and interfere with the function of protein targets (Griffin, et al., *Blood,* (1993), 81:3271–3276; Bock, et al., *Nature,* (1992) 355: 564–566).

Oligonucleotides and their analogs have been developed and used for diagnostic purposes, therapeutic applications and as research reagents. For use as therapeutics, oligonucleotides must be transported across cell membranes or be taken up by cells, and appropriately hybridize to target DNA or RNA. These critical functions depend on the initial stability of the oligonucleotides toward nuclease degradation. A serious deficiency of unmodified oligonucleotides which affects their hybridization potential with target DNA or RNA for therapeutic purposes is the enzymatic degradation of administered oligonucleotides by a variety of intracellular and extracellular ubiquitous nucleolytic enzymes referred to as nucleases. For oligonucleotides to be useful as therapeutics or diagnostics, the oligonucleotides should demonstrate enhanced binding affinity to complementary target nucleic acids, and preferably be reasonably stable to nucleases and resist degradation. For a non-cellular use such as a research reagent, oligonucleotides need not necessarily possess nuclease stability.

A number of chemical modifications have been introduced into oligonucleotides to increase their binding affinity to target DNA or RNA and resist nuclease degradation.

Modifications have been made to the ribose phosphate backbone to increase the resistance to nucleases. These modifications include use of linkages such as methyl phosphonates, phosphorothioates and phosphorodithioates, and the use of modified sugar moieties such as 2'-O-alkyl ribose. Other oligonucleotide modifications include those made to modulate uptake and cellular distribution. A number of modifications that dramatically alter the nature of the internucleotide linkage have also been reported in the literature. These include non-phosphorus linkages, peptide nucleic acids (PNA's) and 2'-5' linkages. Another modification to oligonucleotides, usually for diagnostic and research applications, is labeling with non-isotopic labels, e.g., fluorescein, biotin, digoxigenin, alkaline phosphatase, or other reporter molecules.

A variety of modified phosphorus-containing linkages have been studied as replacements for the natural, readily cleaved phosphodiester linkage in oligonucleotides. In general, most of them (such as the phosphorothioate, phosphoramidates, phosphonates and phosphorodithioates) result in oligonucleotides with reduced binding to complementary targets and decreased hybrid stability. At least one dozen phosphorothioate oligonucleotides and derivatives are presently being used as antisense agents in human clinical trials for the treatment of various disease states. The antisense drug Vitravine™, for use to treat cytomegalovirus (CMV) retinitis in humans, has been approved by regulatory agencies and is comedically marketed.

The structure and stability of chemically modified nucleic acids is of great importance to the design of antisense oligonucleotides. Over the last ten years, a variety of synthetic modifications have been proposed to increase nuclease resistance, or to enhance the affinity of the antisense strand for its target mRNA (Crooke et al., Med. Res. Rev., 1996, 16,319–344; De Mesmaeker et al., Acc. Chem. Res., 1995, 28, 366–374).

RNA exists in what has been termed "A Form" geometry, while DNA exists in "B Form" geometry. In general, RNA:RNA duplexes are more stable, or have higher melting temperatures (Tm) than DNA:DNA duplexes (Sanger et al., Principles of Nucleic Acid Structure, 1984, Springer-Verlag; New York, N.Y.; Lesnik et al., Biochemistry, 1995, 34, 10807–10815; Conte et al., Nucleic Acids Res., 1997,25, 2627–2634). The increased stability of RNA has been attributed to several structural features, most notably the improved base stacking interactions that result from an A-form geometry (Searle et al., Nucleic Acids Res., 1993, 21, 2051–2056). The presence of a hydroxyl group in the 2'-pentofuranosyl (i.e., 2'-sugar) position in RNA is believed to bias the sugar toward a C3' endo pucker (also known as a Northern pucker), which causes the duplex to favor the A-form geometry. On the other hand, 2'-deoxy nucleic acids (those having 2'-deoxy-erythro-pentofuranosyl nucleotides) prefer a C2' endo sugar pucker (also known as Southern pucker), which is thought to impart a less stable B-form geometry (Sanger, W. (1984) Principles of Nucleic Acid Structure, Springer-Verlag, New York, N.Y.). In addition, the 2' hydroxyl groups of RNA can form a network of water mediated hydrogen bonds that help stabilize the RNA duplex (Egli et al., Biochemistry, 1996, 35, 8489–8494).

DNA:RNA hybrid duplexes are usually less stable than pure RNA:RNA duplexes, and depending on their sequence may be either more or less stable than DNA:DNA duplexes (Searle et al., Nucleic Acids Res., 1993, 21, 2051–2056). The structure of a hybrid duplex is intermediate between A- and B-form geometries, which may result in poor stacking interactions (Lane et al., Eur. J. Biochem., 1993, 215, 297–306; Fedoroff et al., J. Mol. Biol., 1993, 233, 509–523; Gonzalez et al., Biochemistry, 1995, 34, 4969–4982; Horton et al., J. Mol. Biol., 1996, 264, 521–533). The stability of a DNA:RNA hybrid is central to antisense therapies as the mechanism requires the binding of a modified DNA strand to a mRNA strand. To effectively inhibit the mRNA, the antisense DNA should have a very high binding affinity with the mRNA. Otherwise the desired interaction between the DNA and target mRNA strand will occur infrequently, thereby decreasing the efficacy of the antisense oligonucleotide.

One synthetic 2'-modification that imparts increased nuclease resistance and a very high binding affinity to nucleotides is the 2'-methoxyethoxy (MOE, 2'-OCH$_2$CH$_2$OCH$_3$) side chain (Baker et al., J. Biol. Chem., 1997, 272, 11944–12000; Freier et al., Nucleic Acids Res., 1997, 25, 4429–4443). One of the immediate advantages of the MOE substitution is the improvement in binding affinity, which is greater than many similar 2' modifications such as O-methyl, O-propyl, and O-aminopropyl (Freier and Altmann, Nucleic Acids Research, (1997) 25:4429–4443). 2'-O-Methoxyethyl-substituted compounds also have been shown to be antisense inhibitors of gene expression with promising features for in vivo use (Martin, P., Helv. Chim. Acta, 1995, 78, 486–504; Altmann et al., Chimia, 1996, 50, 168–176; Altmann et al., Biochem. Soc. Trans., 1996, 24, 630–637; and Altmann et al., Nucleosides Nucleotides, 1997, 16, 917–926). Such compounds typically display improved RNA affinity and higher nuclease resistance relative to DNA. Chimeric oligonucleotides with 2'-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

Recently Damha et. al., published two paper describing certain oligonucleotides that utilized arabino-pentofuranosyl nucleotides as building blocks (Damha et. al., J.A.C.S., 1998, 120, 12976–12977 and Damha et. al., Bioconjugate Chem., 1999, 10, 299–305). The arabino-pentofuranosyl oligonucleotides, i.e., arabinonucleic acids, described by Damha et. al., utilized either arabinose or 2'-deoxy-2'-fluoro arabinose as the sugar unit of their respective nucleotides. In one of the two arabinonucleic acids described, all of the nucleotides of the nucleic acid were arabinose and in the other, all of the nucleotides were 2'-deoxy-2'-fluoro arabinose. In both of these nucleic acids, the nucleotides were joined via phosphodiester linkages. These authors were able to show that the 2'-fluoro arabino-containing oligonucleotides when bound to RNA activated cleavage of the RNA by E. coli and HIV-RT RNase H. The authors further noted that while the two arabinonucleic acids they described were more stable to serum and cellular nucleases than DNA they were less stable than normal phosphorothioate deoxyoligonucleotides.

Although the known modifications to oligonucleotides have contributed to the development of oligonuclotides for various uses, including use in diagnostics, therapeutics and as research reagents, there still exists a need in the art for further oligonucleotides having enhanced hybrid binding affinity and/or increased nuclease resistance and that can take advantage of the RNase H termination mechanism.

SUMMARY OF THE INVENTION

In one aspect, the present invention is directed to oligonucleotides having multiple properties. One of these properties is the ability to form a double stranded structure with an RNA and elicit RNase H cleavage of the RNA. Further properties of the oligonucleotides include having improved binding affinity and nuclease resistance. The oligonucleotides of the invention comprise oligonucleotide formed from a plurality of nucleotides. A first portion of the nucleotides are joined together in a contiguous sequence with each nucleotide of this portion selected as a nucleotide that has B-form conformational geometry when joined in a contiguous sequence with other nucleotides. Included in this first portion of nucleotides are ribonucleotides or arabino nucleotides. The oligonucleotides include a further portion of nucleotides that are joined together in at least one contiguous sequence. Each of these further nucleotides are selected as ribonucleotides that have A-form conformational geometry when joined in a contiguous sequence.

In preferred embodiments of the invention, each of the nucleotides of the first portion of nucleotides, independently, are selected to be 2'-SCH$_3$ ribonucleotides, 2'-NH$_2$ ribonucleotides, 2'-NH(C$_1$–C$_2$ alkyl) ribonucleotides, 2'-N(C$_1$–C$_2$ alkyl)$_2$ ribonucleotides, 2'-CF$_3$ ribonucleotides, 2'=CH$_2$ ribonucleotides, 2'=CHF ribonucleotides, 2'=CF$_2$ ribonucleotides, 2'-CH$_3$ ribonucleotides, 2'-C$_2$H$_5$ ribonucleotides, 2'-CH=CH$_2$ ribonucleotides or 2'-C≡CH ribonucleotides. These are joined together in a contiguous sequence by phosphate, phosphorothioate, phosphorodithioate or boranophosphate linkages.

In a further preferred embodiment of the invention, each of the nucleotides of said further portion of nucleotides, independently, are selected to be 2'-fluoro nucleotides or nucleotides having a 2'-substituent having the formula I or II:

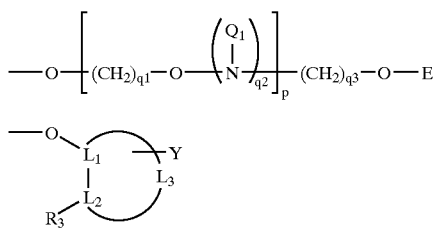

wherein

E is C$_1$–C$_{10}$ alkyl, N(Q$_1$)(Q$_2$) or N=C(Q$_1$)(Q$_2$);

each Q$_1$ and Q$_2$ is, independently, H, C$_1$–C$_{10}$ alkyl, dialkylaminoalkyl, a nitrogen protecting group, a tethered or untethered conjugate group, a linker to a solid support, or Q$_1$ and Q$_2$, together, are joined in a nitrogen protecting group or a ring structure that can include at least one additional heteroatom selected from N and O;

R$_3$ is OX, SX, or N(X)$_2$;

each X is, independently, H, C$_1$–C$_8$ alkyl, C$_1$–C$_8$ haloalkyl, C(=NH)N(H)Z, C(=O)N(H)Z or OC(=O)N(H)Z;

Z is H or C$_1$–C$_8$ alkyl;

L$_1$, L$_2$ and L$_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(Q$_1$)(Q$_2$), O(Q$_1$), halo, S(Q$_1$), or CN;

each q$_1$ is, independently, from 2 to 10;

each q$_2$ is, independently, 0 or 1;

m is 0, 1 or 2;

p is from 1 to 10; and q$_3$ is from 1 to 10 with the proviso that when p is 0, q$_3$ is greater than 1.

A more preferred group for use as the further portion of nucleotides are 2'-F ribonucleotides, 2'-O—(C$_1$–C$_6$ alkyl) ribonucleotides, or 2'-O—(C$_1$–C$_6$ substituted alkyl) ribonucleotides wherein the substitution is C$_1$–C$_6$ ether, C$_1$–C$_6$ thioether, amino, amino(C$_1$–C$_6$ alkyl) or amino(C$_1$–C$_6$ alkyl)$_2$. These nucleotides are joined together in sequence by 3'–5' phosphodiester, 2'–5' phosphodiester, phosphorothioate, Sp phosphorothioate, Rp phosphorothioate, phosphorodithioate, 3'-deoxy-3'-amino phosphoroamidate, 3'-methylenephosphonate, methylene (methylimino), dimethylhydazino, amide 3 (i.e., (3')—CH$_2$—NH—C(O)—(5')), amide 4 (i.e., (3')—CH$_2$—C(O)—NH—(5')) or boranophosphate linkages.

In one preferred embodiment of the invention, at least two of the nucleotides of the further portion of nucleotides are joined together in a contiguous sequence that is position 3' to the contiguous sequence of the first portion of nucleotides. In an additional preferred embodiment of the invention, at least two of the further portion of nucleotides are joined together in a continuous sequence that is position 5' to the continuous sequence of the first portion of nucleotides.

In a further preferred embodiment of the invention, at least two of the nucleotides of the further portion of nucleotides are joined together in a continuous sequence that is position 3' to the continuous sequence of the first portion of nucleotides and at least two of the further portion of nucleotides are joined together in a continuous sequence that is position 5' to the continuous sequence of the first portion of nucleotides.

A first preferred group of nucleotides for use as the first portion of nucleotides include 2'-SCH$_3$ ribonucleotides, 2'-NH$_2$ ribonucleotides, 2'-NH(C C$_2$ alkyl) ribonucleotides, 2'-N(C$_1$–C$_2$ alkyl)$_2$ ribonucleotides, 2'=CH$_2$ ribonucleotides, 2'-CH$_3$ ribonucleotides, 2'-C$_2$H$_5$ ribonucleotides, 2'-CH=CH$_2$ ribonucleotides and 2'-C≡CH ribonucleotides. A more preferred group include 2'-SCH$_3$ ribonucleotides, 2'-NH$_2$ ribonucleotides, 2'-NH (C$_1$–C$_2$ alkyl) ribonucleotides, 2'-N(C$_1$–C$_2$ alkyl)$_2$ ribonucleotides and 2'-CH$_3$ ribonucleotides. A further preferred group include 2'-SCH$_3$ ribonucleotides, 2'-NH$_2$ ribonucleotides and 2'-CH$_3$ ribonucleotides. Particularly preferred are is 2'-SCH$_3$ ribonucleotides.

A further group of nucleotides that are preferred of use as the nucleotides of the first portion of the oligonucleotides of the inventions are 2'-CN arabino nucleotides, 2'-F arabino nucleotides, 2'-Cl arabino nucleotides, 2'-Br arabino nucleotides, 2'-N$_3$ arabino nucleotides, 2'-OH arabino nucleotides, 2'-O—CH$_3$ arabino nucleotides and 2'-dehydro-2'-CH$_3$ arabino nucleotides. A more preferred group include 2'-F arabino nucleotides, 2'-OH arabino nucleotides and 2'-O—CH$_3$ arabino nucleotides. A further preferred group include 2'-F arabino nucleotides and 2'-OH arabino nucleotides. Particularly preferred are 2'-F arabino nucleotides.

Particularly preferred oligonucleotides of the invention include selecting the nucleotides of the first portion of nucleotides to be 2'-SCH$_3$ ribonucleotides, 2'-NH$_2$ ribonucleotides, 2'-NH(C$_1$–C$_2$ alkyl) ribonucleotides, 2'-N (C$_1$–C$_2$ alkyl)$_2$ ribonucleotides, 2'-CH$_3$ ribonucleotides, 2'-CH=CH$_2$ ribonucleotides or 2'-C≡CH ribonucleotides and selecting the nucleotides of the further portion of nucleotides to be 2'-F ribonucleotides, 2'-O—(C$_1$–C$_6$ alkyl) ribonucleotides or 2'-O—(C$_1$–C$_6$ substituted alkyl) ribonucleotides wherein the substitution is C$_1$–C$_6$ ether, C$_1$–C$_6$ thioether, amino, amino(C$_1$–C$_6$ alkyl) or amino(C$_1$–C$_6$ alkyl)$_2$.

Further preferred oligonucleotides of the invention include selecting the nucleotides of said first portion of nucleotides to be 2'-CN arabino nucleotides, 2'-F arabino nucleotides, 2'-Cl arabino nucleotides, 2'-Br arabino nucleotides, 2'-N$_3$ arabino nucleotides, 2'-OH arabino nucleotides, 2'-O—CH$_3$ arabino nucleotides or 2'-dehydro-2'-CH$_3$ arabino nucleotides and selecting the nucleotides of the further portion of nucleotides to be 2'-F ribonucleotides, 2'-O—(C$_1$–C$_6$ alkyl) ribonucleotides or 2'-O—(C$_1$–C$_6$ substituted alkyl) ribonucleotides wherein the substitution is C$_1$–C$_6$ ether, C$_1$–C$_6$ thioether, amino, amino(C$_1$–C$_6$ alkyl) or amino(C$_1$–C$_6$ alkyl)$_2$.

Particularly preferred are oligonucleotide of the invention where each nucleotide of the first portion of nucleotides is a 2'-F arabino nucleotides or a 2'-OH arabino nucleotides and each nucleotide of the further portion of nucleotides is a 2'-O—(C$_1$–C$_6$ substituted alkyl) ribonucleotide wherein the substitution is C$_1$–C$_6$ ether, C$_1$–C$_6$ thioether, amino, amino (C$_1$–C$_6$ alkyl) or amino(C$_1$–C$_6$ alkyl)$_2$.

In further preferred oligonucleotides of the invention the further portion of the plurality of nucleotides comprise at least two nucleotides joined together in a contiguous sequence that is position at the 3' terminus end of the oligonucleotide. In an additional preferred oligonucleotide of the invention the further portion of said plurality of nucleotides comprise at least two nucleotides joined together in a contiguous sequence that is position at the 5' terminus end of the oligonucleotide. In even further preferred oligonucleotides of the invention the further portion of the plurality of nucleotides comprise at least two nucleotides joined together in a contiguous sequence that is position at the 3' terminus end of the oligonucleotide and at least two nucleotides joined together in a contiguous sequence that is position at the 5' terminus end of the oligonucleotide. Preferred linkages for joining these nucleotides together in an oligonucleotide of the invention include 2'–5' phosphodiester linkages, 3'-methylenephosphonate linkages, Sp phosphorothioate linkages, methylene(methylimino)linkages, dimethyhydrazino linkages, 3'-deoxy-3'-amino phosphoroamidate linkages, amide 3 linkages or amide 4 linkages. Particularly preferred joining linkages are 2'–5' phosphodiester linkages, 3'-methylenephosphonate linkages, Sp phosphorothioate linkages or methylene(methylimino) linkages.

In further preferred oligonucleotides of the invention, nucleotides for use in the further portion of nucleotides comprises 2'-alkylamino substituted nucleotides located at the 3' terminus, the 5' terminus or both the 3' and 5' terminus of the oligonucleotide. Particularly preferred are 2'-O-alkylamines such as 2'-O-ethylamine and 2'-O-propylamine.

Further oligonucleotides of the invention comprise oligonucleotides made up of a plurality of linked nucleotides at least two of which comprise nucleotides that are not 2'-deoxy-erythro-pentofuranosyl nucleotides and that have a C2' endo type pucker or an O4' endo type pucker and that are joined together in a contiguous sequence and other nucleotides comprising nucleotides that have a C3' endo type pucker. Preferred are oligonucleotides having the C3' endo type pucker nucleotides joined together in a contiguous sequence that is positioned 3' to the contiguous sequence of the nucleotides having the C2' endo type pucker or O4' endo type pucker. Further preferred oligonucleotides are oligonucleotides wherein the nucleotides having the C3' endo type pucker are joined together in a contiguous sequence that is positioned 5' to the contiguous sequence of having the C2' endo type pucker or O4' endo type pucker. Additional preferred oligonucleotide are oligonucleotides where a portion of the nucleotides having the C3' endo type pucker are joined together in a contiguous sequence that is positioned 3' to the contiguous sequence of nucleotides having the C2' endo type pucker or O4' endo type pucker and a further portion of nucleotides having the C3' endo type pucker are joined together in a contiguous sequence that is positioned 5' to the contiguous sequence of nucleotides having the C2' endo type pucker or O4' endo type pucker.

DESCRIPTION OF PREFERRED EMBODIMENTS

Figure 1:
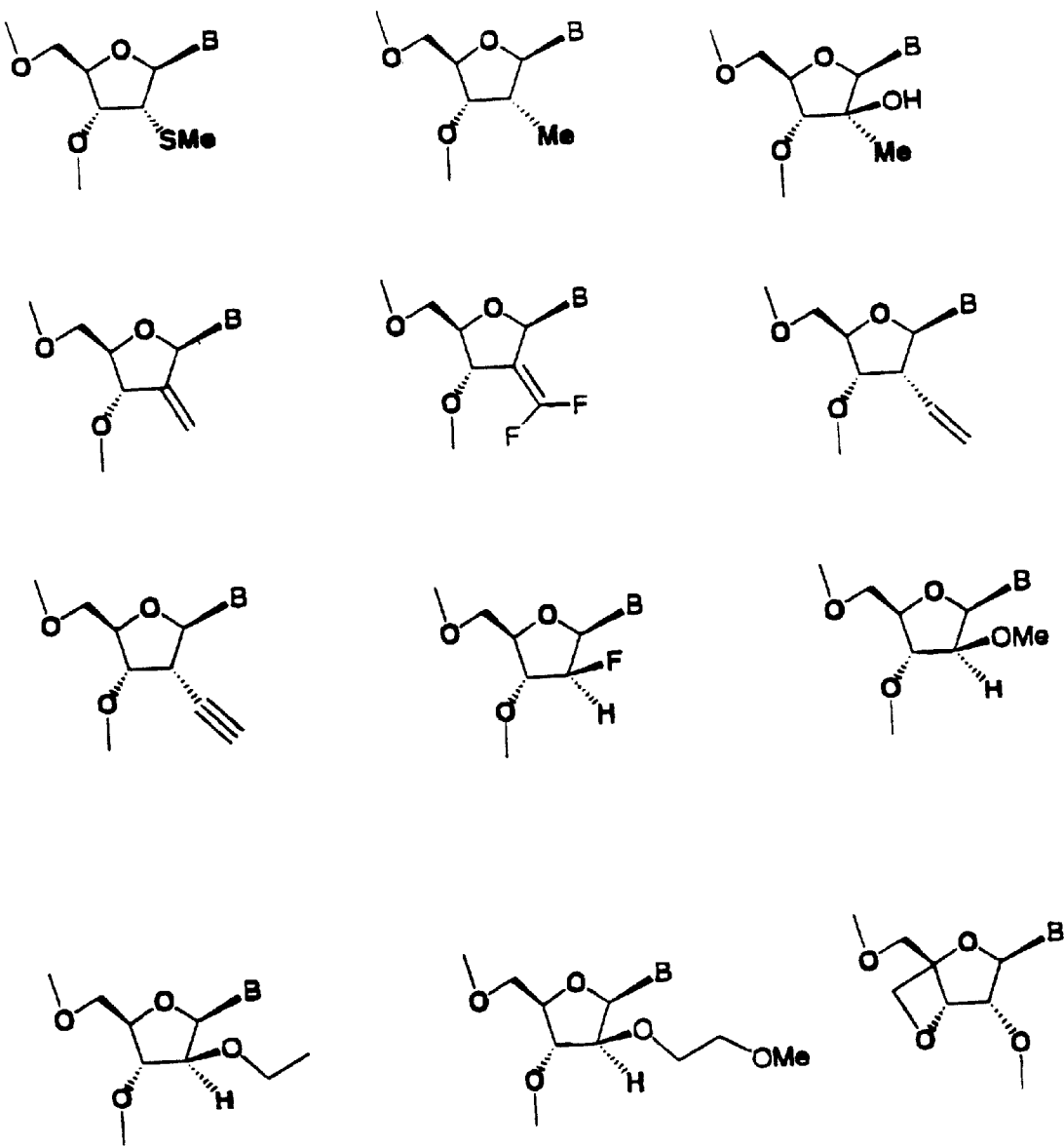
FIG. 1 illustrates a preferred group of nucleotide fragments for use in the B-form portion (the C2' endo/O4' endo portion) of oligonucleotides of the invention.
Figure 2:
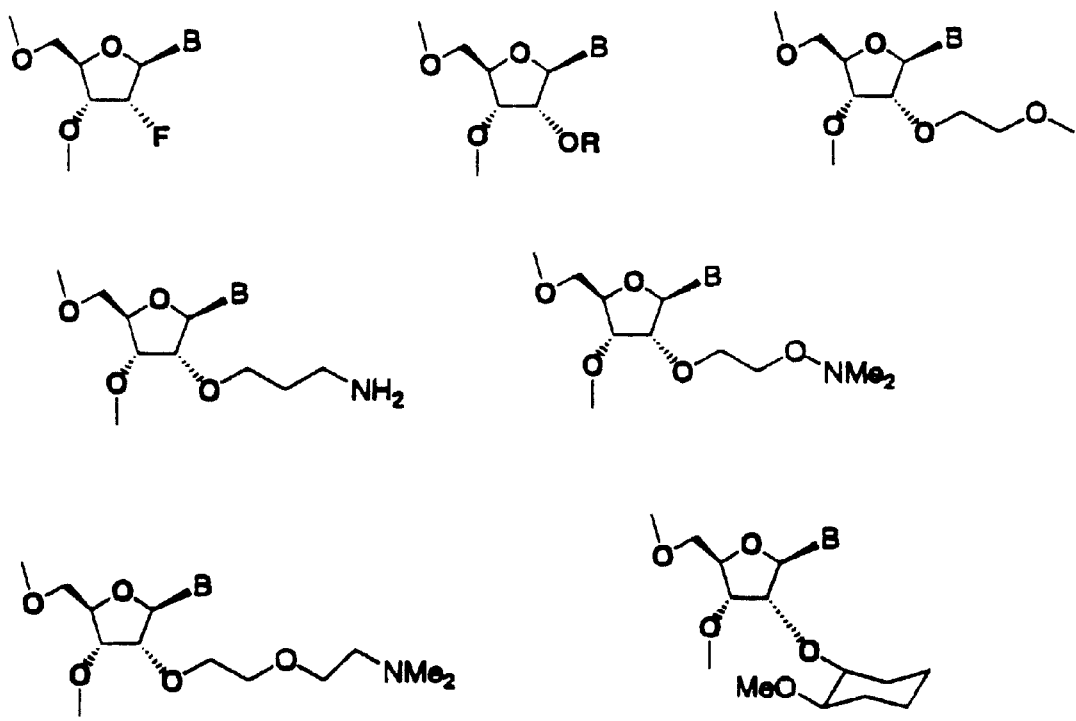
FIG. 2 illustrates a preferred group of nucleotide fragments for use in the A-form portion (the C3'endo portion) of oligonucleotides of the invention.
Figure 3:
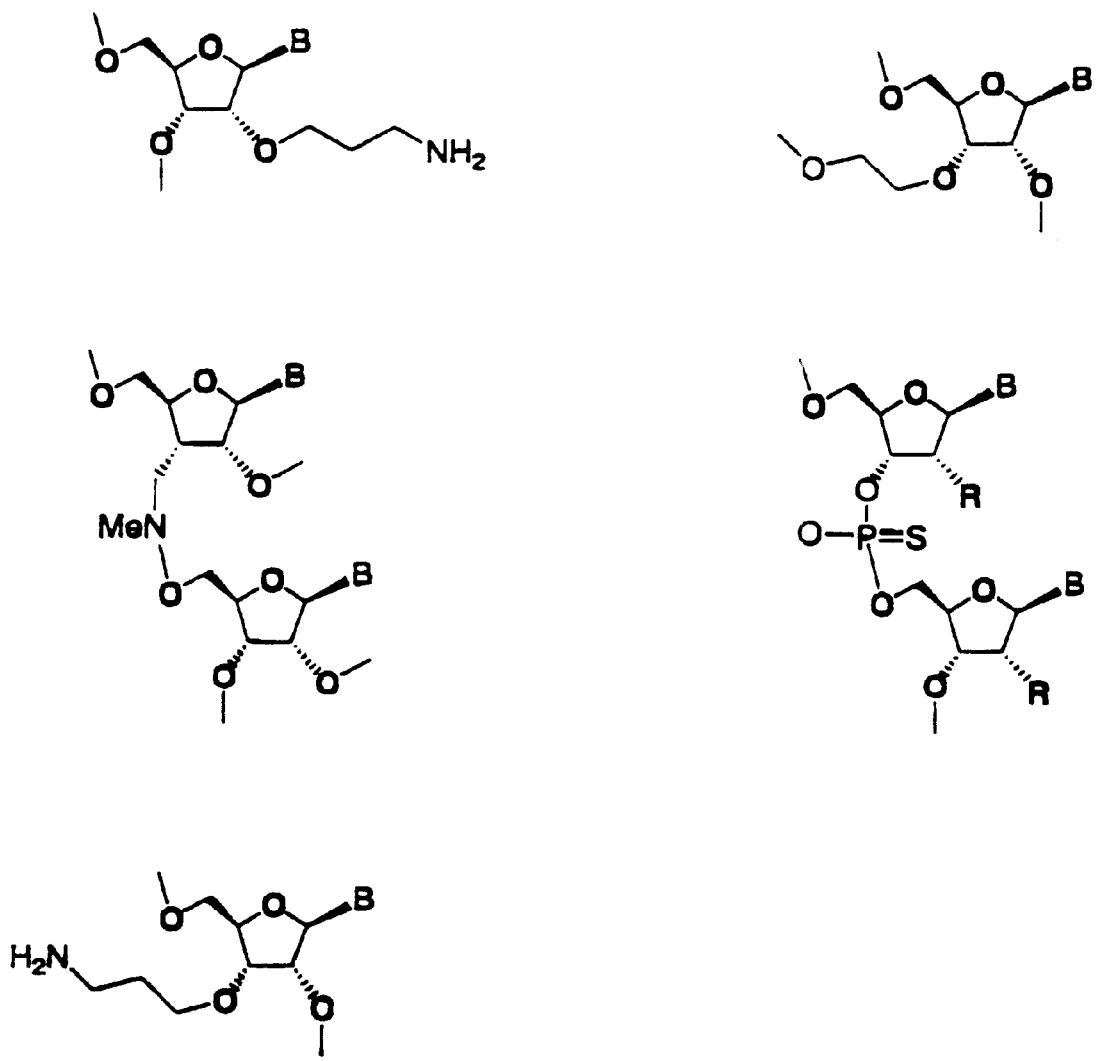
FIG. 3 illustrates a preferred group of nucleotide fragments for use in A-form portions at the 3' terminus of oligonucleotides of the invention.

In one aspect, the present invention is directed to novel oligonucleotides that have certain desirable properties that contribute to increases in binding affinity and/or nuclease resistance, coupled with the ability to serve as substrates for RNase H.

The oligonucleotide of the invention are formed from a plurality of nucleotides that are joined together via internucleotide linkages. While joined together as a unit in the oligonucleotide, the individual nucleotides of oligonucleotides are of several types. Each of these types contribute unique properties to the oligonucleotide. A first type of nucleotides are joined together in a continuous sequence that forms a first portion of the oligonucleotide. The remaining nucleotides are of at least one further type and are located in one or more remaining portions or locations within the oligonucleotide. Thus, the oligonucleotides of the invention include a nucleotide portion that contributes one set of attributes and a further portion (or portions) that contributes another set of attributes.

One attribute that is desirable is eliciting RNase H activity. To elicit RNase H activity, a portion of the oligonucleotides of the invention is selected to have B-form like conformational geometry. The nucleotides for this B-form portion are selected to specifically include ribo-pentofuranosyl and arabino-pentofuranosyl nucleotides. 2'-Deoxy-erythro-pentfuranosyl nucleotides also have B-form geometry and elicit RNase H activity. While not specifically excluded, if 2'-deoxy-erythro-pentfuranosyl nucleotides are included in the B-form portion of an oligonucleotide of the invention, such 2'-deoxy-erythro-pentfuranosyl nucleotides preferably does not constitute the totality of the nucleotides of that B-form portion of the oligonucleotide, but should be used in conjunction with ribonucleotides or an arabino nucleotides. As used herein, B-form geometry is inclusive of both C2'-endo and O4'-endo pucker, and the ribo and arabino nucleotides selected for inclusion in the oligonucleotide B-form portion are selected to be those nucleotides having C2'-endo conformation or those nucleotides having O4'-endo conformation. This is consistent with Berger, et. al., *Nucleic Acids Research*, 1998, 26, 2473–2480, who pointed out that in considering the furanose conformations in which nucleosides and nucleotides reside, B-form consideration should also be given to a O4'-endo pucker contribution.

A-form nucleotides are nucleotides that exhibit C3'-endo pucker, also known as north, or northern, pucker. In addition to the B-form nucleotides noted above, the A-form nucleotides can be C3'-endo pucker nucleotides or can be nucleotides that are located at the 3' terminus, at the 5' terminus, or at both the 3' and the 5' terminus of the oligonucleotide. Alternatively, A-form nucleotides can exist both in a C3'-endo pucker and be located at the ends, or termini, of the oligonucleotide. In selecting nucleotides that have C3'-endo pucker or in selecting nucleotides to reside at the 3' or 5' ends of the oligonucleotide, consideration is given to binding affinity and nuclease resistance properties that such nucleotides need to impart to the resulting the oligonucleotide.

Nucleotides selected to reside at the 3' or 5' termini of oligonucleotides of the invention are selected to impart nuclease resistance to the oligonucleotide. This nuclease resistance can also be achieved via several mechanisms, including modifications of the sugar portions of the nucleotide units of the oligonucleotides, modification of the internucleotide linkages or both modification of the sugar and the internucleotide linkage.

A particularly useful group of nucleotides for use in increasing nuclease resistance at the termini of oligonucleotides are those having 2'-O-alkylamino groups thereon. The amino groups of such nucleotides can be groups that are protonated at physiological pH. These include amines, monoalkyl substituted amines, dialkyl substituted amines and heterocyclic amines such as imidazole. Particularly useful are the lower alkyl amines including 2'-O-ethylamine and 2'-O-propylamine. Such O-alkylamines can also be included on the 3' position of the 3' terminus nucleotide. Thus the 3' terminus nucleotide could include both a 2' and a 3'-O-alkylamino substituent.

In selecting for nuclease resistance, it is important not to detract from binding affinity. Certain phosphorus based linkage have been shown to increase nuclease resistance. The above described phosphorothioate linkage increase nuclease resistance, however, it also causes loss of binding affinity. Thus, generally for use in this invention, if phosphorothioate internucleotide linkage are used, other modification will be made to nucleotide units that increase binding affinity to compensate for the decreased affinity contribute by the phosphorothioate linkages.

Other phosphorus based linkages having increase nuclease resistance that do not detract from binding affinity include 3'-methylene phosphonates and 3'-deoxy-3'-amino-phosphoroamidate linkages. A further class of linkages that contribute nuclease resistance but do not detract from binding affinity are non-phosphate in nature. Preferred among these are methylene(methylimino) linkages, dimethylhydraxino linkages, and amine 3 and amide 4 linkages as described (Freier and Altmann, *Nucleic Acid Research*, 1997, 25, 4429–4443).

There are a number of potential items to consider when designing oligonucleotides having improved binding affinities. It appears that one effective approach to constructing modified oligonucleotides with very high RNA binding affinity is the combination of two or more different types of modifications, each of which contributes favorably to various factors that might be important for binding affinity.

Freier and Altmann, *Nucleic Acids Research*, (1997) 25:4429–4443, recently published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and $T_m$. Sugar modifications studied included substitutions on the 2'-position of the sugar, 3'-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Numerous backbone modifications were also investigated including backbones bearing phosphorus, backbones that did not bear a phosphorus atom, and backbones that were neutral.

Four general approaches might be used to improve hybridization of oligonucleotides to RNA targets. These include: preorganization of the sugars and phosphates of the oligodeoxynucleotide strand into conformations favorable for hybrid formation, improving stacking of nucleobases by the addition of polarizable groups to the heterocycle bases of the nucleotides of the oligonucleotide, increasing the number of H-bonds available for A-U pairing, and neutralization of backbone charge to facilitate removing undesirable repulsive interactions. We have found that by utilizing the first of these, preorganization of the sugars and phosphates of the oligodeoxynucleotide strand into conformations favorable for hybrid formation, to be a preferred method to achieve improve binding affinity. It can further be used in combination with the other three approaches.

Sugars in DNA:RNA hybrid duplexes frequently adopt a C3' endo conformation. Thus modifications that shift the conformational equilibrium of the sugar moieties in the single strand toward this conformation should preorganize the antisense strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

Representative 2'-substituent groups amenable to the present invention that give A-form conformational properties to the nucleotides include 2'-O-alkyl, 2'-O-substituted alkyl and 2'-fluoro substituent groups. Preferred for the substituent groups are various alkyl and aryl ethers and thioethers, amines and monoalkyl and dialkyl substituted amines. A particular preferred group include those having the formula I or II:

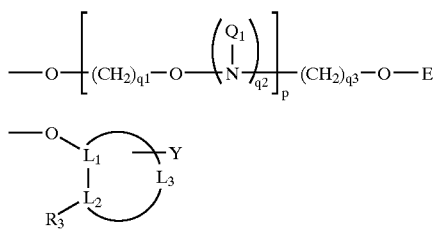

wherein
E is $C_1$–$C_{10}$ alkyl, $N(Q_1)(Q_2)$ or $N=C(Q_1)(Q_2)$;
each $Q_1$ and $Q_2$ is, independently, H, $C_1$–$C_{10}$ alkyl, dialkylaminoalkyl, a nitrogen protecting group, a tethered or untethered conjugate group, a linker to a solid support, or $Q_1$ and $Q_2$, together, are joined in a nitrogen protecting group or a ring structure that can include at least one additional heteroatom selected from N and O;
$R_3$ is OX, SX, or $N(X)_2$;
each X is, independently, H, $C_1$–$C_8$ alkyl, $C_1$–$C_8$ haloalkyl, $C(=NH)N(H)Z$, $C(=O)N(H)Z$ or $OC(=O)N(H)Z$;
Z is H or $C_1$–$C_8$ alkyl;
$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;
Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $O(Q_1)$, halo, $S(Q_1)$, or CN;
each $q_1$ is, independently, from 2 to 10;
each $q_2$ is, independently, 0 or 1;
m is 0, 1 or 2;
p is from 1 to 10; and
$q_3$ is from 1 to 10 with the proviso that when p is 0, $q_3$ is greater than 1.

The above 2'-substituents confer a 3'-endo pucker to the sugar where they are incorporated. This pucker conformation further assists in increasing the $T_m$ of the oligonucleotide with its target.

The high binding affinity resulting from 2' substitution has been partially attributed to the 2' substitution causing a C3' endo sugar pucker which in turn may give the oligomer a favorable A-form like geometry. This is a reasonable hypothesis since substitution at the 2' position by a variety of electronegative groups (such as fluoro and O-alkyl chains) has been demonstrated to cause C3' endo sugar puckering (De Mesmaeker et al., Acc. Chem. Res., 1995, 28, 366–374; Lesnik et al., Biochemistry, 1993, 32, 7832–7838).

In addition, for 2'-substituents containing an ethylene glycol motif, a gauche interaction between the oxygen atoms around the O—C—C—O torsion of the side chain may have a stabilizing effect on the duplex (Freier et al., Nucleic Acids Research, (1997) 25:4429–4442). Such gauche interactions have been observed experimentally for a number of years (Wolfe et al., Acc. Chem. Res., 1972,5,102; Abe et al., J. Am. Chem. Soc., 1976,98,468). This gauche effect may result in a configuration of the side chain that is favorable for duplex formation. The exact nature of this stabilizing configuration has not yet been explained. While we do not want to be bound by theory, it may be that holding the O—C—C—O torsion in a single gauche configuration, rather than a more random distribution seen in an alkyl side chain, provides an entropic advantage for duplex formation.

To better understand the higher RNA affinity of 2'-O-methoxyethyl substituted RNA and to examine the conformational properties of the 2'-O-methoxyethyl substituent, a self-complementary dodecamer oligonucleotide 2'-O-MOE r(CGCGAAUUCGCG) SEQ ID NO: 1 was synthesized, crystallized and its structure at a resolution of 1.7 Angstrom was determined. The crystallization conditions used were 2 mM oligonucleotide, 50 mM Na Hepes pH 6.2–7.5, 10.50 mM $MgCl_2$, 15% PEG 400. The crystal data showed: space group C2, cell constants a=41.2 Å, b=34.4 Å, c=46.6 Å, β=92.4°. The resolution was 1.7 Å at −170° C. The current R=factor was 20% ($R_{free}$ 26%).

This crystal structure is believed to be the first crystal structure of a fully modified RNA oligonucleotide analogue. The duplex adopts an overall A-form conformation and all modified sugars display C3'-endo pucker. In most of the 2'-O-substituents, the torsion angle around the A'-B' bond, as depicted in Structure II below, of the ethylene glycol linker has a gauche conformation. For 2'-O-MOE, A' and B' of Structure II below are methylene moieties of the ethyl portion of the MOE and R' is the methoxy portion.

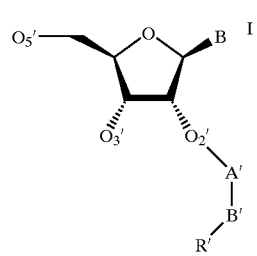

II

In the crystal, the 2'-O-MOE RNA duplex adopts a general orientation such that the crystallographic 2-fold rotation axis does not coincide with the molecular 2-fold rotation axis. The duplex adopts the expected A-type geometry and all of the 24 2'-O-MOE substituents were visible in the electron density maps at full resolution. The electron density maps as well as the temperature factors of substituent atoms indicate flexibility of the 2'-O-MOE substituent in some cases.

Most of the 2'-O-MOE substituents display a gauche conformation around the C—C bond of the ethyl linker. However, in two cases, a trans conformation around the C—C bond is observed. The lattice interactions in the crystal include packing of duplexes against each other via their minor grooves. Therefore, for some residues, the conformation of the 2'-O-substituent is affected by contacts to an adjacent duplex. In general, variations in the conformation of the substituents (e.g. g⁺ or g⁻ around the C—C bonds) create a range of interactions between substituents, both inter-strand, across the minor groove, and intra-strand. At one location, atoms of substituents from two residues are in van der Waals contact across the minor groove. Similarly, a close contact occurs between atoms of substituents from two adjacent intra-strand residues.

Previously determined crystal structures of A-DNA duplexes were for those that incorporated isolated 2'-O-methyl T residues. In the crystal structure noted above for the 2'-O-MOE substituents, a conserved hydration pattern has been observed for the 2'-O-MOE residues. A single water molecule is seen located between O2', O3' and the methoxy oxygen atom of the substituent, forming contacts to all three of between 2.9 and 3.4 A. In addition, oxygen atoms of substituents are involved in several other hydrogen bonding contacts. For example, the methoxy oxygen atom of a particular 2'-O-substituent forms a hydrogen bond to N3 of an adenosine from the opposite strand via a bridging water molecule.

In several cases a water molecule is trapped between the oxygen atoms O2', O3' and OC' of modified nucleosides. 2'-O-MOE substituents with trans conformation around the C—C bond of the ethylene glycol linker are associated with close contacts between OC' and N2 of a guanosine from the opposite strand, and, water-mediated, between OC' and N3(G). When combined with the available thermodynamic data for duplexes containing 2'-O-MOE modified strands, this crystal structure allows for further detailed structure-stability analysis of other antisense modifications.

In extending the crystallographic structure studies, molecular modeling experiments were performed to study further enhanced binding affinity of oligonucleotides having 2'-O-modifications of the invention. The computer simulations were conducted on compounds of SEQ ID NO: 1, above, having 2'-O-modifications of the invention located at each of the nucleoside of the oligonucleotide. The simulations were performed with the oligonucleotide in aqueous solution using the AMBER force field method (Cornell et al., *J. Am. Chem. Soc.,* 1995,117,5179–5197)(modeling software package from UCSF, San Francisco, Calif.). The calculations were performed on an Indigo2 SGI machine (Silicon Graphics, Mountain View, Calif.).

Further 2'-O-modifications of the inventions include those having a ring structure that incorporates a two atom portion corresponding to the A' and B' atoms of Structure II. The ring structure is attached at the 2' position of a sugar moiety of one or more nucleosides that are incorporated into an oligonucleotide. The 2'-oxygen of the nucleoside links to a carbon atom corresponding to the A' atom of Structure II. These ring structures can be aliphatic, unsaturated aliphatic, aromatic or heterocyclic. A further atom of the ring (corresponding to the B' atom of Structure II), bears a further oxygen atom, or a sulfur or nitrogen atom. This oxygen, sulfur or nitrogen atom is bonded to one or more hydrogen atoms, alkyl moieties, or haloalkyl moieties, or is part of a further chemical moiety such as a ureido, carbamate, amide or amidine moiety. The remainder of the ring structure restricts rotation about the bond joining these two ring atoms. This assists in positioning the "further oxygen, sulfur or nitrogen atom" (part of the R position as described above) such that the further atom can be located in close proximity to the 3'-oxygen atom (O3') of the nucleoside.

The ring structure can be further modified with a group useful for modifying the hydrophilic and hydrophobic properties of the ring to which it is attached and thus the properties of an oligonucleotide that includes the 2'-O-modifications of the invention. Further groups can be selected as groups capable of assuming a charged structure, e.g. an amine. This is particularly useful in modifying the overall charge of an oligonucleotide that includes a 2'-O-modifications of the invention. When an oligonucleotide is linked by charged phosphate groups, e.g. phosphorothioate or phosphodiester linkages, location of a counter ion on the 2'-O-modification, e.g. an amine functionality, locally naturalizes the charge in the local environment of the nucleotide bearing the 2'-O-modification. Such neutralization of charge will modulate uptake, cell localization and other pharmacokinetic and pharmacodynamic effects of the oligonucleotide.

Preferred ring structures of the invention for inclusion as a 2'-O modification include cyclohexyl, cyclopentyl and phenyl rings as well as heterocyclic rings having spacial footprints similar to cyclohexyl, cyclopentyl and phenyl rings. Particularly preferred 2'-O-substituent groups of the invention are listed below including an abbreviation for each:

2'-O-(trans 2-methoxy cyclohexyl)—2'-O-(TMCHL)
2'-O-(trans 2-methoxy cyclopentyl)—2'-O-(TMCPL)
2'-O-(trans 2-ureido cyclohexyl)—2'-O-(TUCHL)
2'-O-(trans 2-methoxyphenyl)—2'-O-(2 MP)

Structural details for duplexes incorporating such 2-O-substituents were analyzed using the described AMBER force field program on the Indigo2 SGI machine. The simulated structure maintained a stable A-form geometry throughout the duration of the simulation. The presence of the 2' substitutions locked the sugars in the C3'-endo conformation.

The simulation for the TMCHL modification revealed that the 2'-O-(TMCHL) side chains have a direct interaction with water molecules solvating the duplex. The oxygen atoms in the 2'-O-(TMCHL) side chain are capable of forming a water-mediated interaction with the 3' oxygen of the phosphate backbone. The presence of the two oxygen atoms in the 2'-O-(TMCHL) side chain gives rise to favorable gauche interactions. The barrier for rotation around the O—C—C—O torsion is made even larger by this novel modification. The preferential preorganization in an A-type geometry increases the binding affinity of the 2'-O-(TMCHL) to the target RNA. The locked side chain conformation in the 2'-O-(TMCHL) group created a more favorable pocket for binding water molecules. The presence of these water molecules played a key role in holding the side chains in the preferable gauche conformation. While not wishing to be bound by theory, the bulk of the substituent, the diequatorial orientation of the substituents in the cyclohexane ring, the water of hydration and the potential for trapping of metal ions in the conformation generated will additionally contribute to improved binding affinity and nuclease resistance of oligonucleotides incorporating nucleosides having this 2'-O-modification.

As described for the TMCHL modification above, identical computer simulations of the 2'-O-(TMCPL), the 2'-O-(2 MP) and 2'-O-(TUCHL) modified oligonucleotides in aqueous solution also illustrate that stable A-form geometry will be maintained throughout the duration of the simulation. The presence of the 2' substitution will lock the sugars in the C3'-endo conformation and the side chains will have direct interaction with water molecules solvating the duplex. The oxygen atoms in the respective side chains are capable of forming a water-mediated interaction with the 3' oxygen of the phosphate backbone. The presence of the two oxygen atoms in the respective side chains give rise to the favorable gauche interactions. The barrier for rotation around the respective O—C—C—O torsions will be made even larger by respective modification. The preferential preorganization in A-type geometry will increase the binding affinity of the respective 2'-O-modified oligonucleotides to the target RNA. The locked side chain conformation in the respective modifications will create a more favorable pocket for binding water molecules. The presence of these water molecules plays a key role in holding the side chains in the preferable gauche conformation. The bulk of the substituent, the diequatorial orientation of the substituents in their respective rings, the water of hydration and the potential trapping of metal ions in the conformation generated will all contribute to improved binding affinity and nuclease resistance of oligonucleotides incorporating nucleosides having these respective 2'-O-modification.

Preferred for use as the B-form nucleotides for eliciting RNase H are ribonucleotides having 2'-deoxy-2'-S-methyl, 2'-deoxy-2'-methyl, 2'-deoxy-2'-amino, 2'-deoxy-2'-mono or dialkyl substituted amino, 2'-deoxy-2'-fluoromethyl, 2'-deoxy-2'-difluoromethyl, 2'-deoxy-2'-trifluoromethyl, 2'-deoxy-2'-methylene, 2'-deoxy-2'-fluoromethylene, 2'-deoxy-2'-difluoromethylene, 2'-deoxy-2'-ethyl, 2'-deoxy-2'-ethylene and 2'-deoxy-2'-acetylene. These nucleotides can alternately be described as 2'-SCH$_3$ ribonucleotide, 2'-CH$_3$ ribonucleotide, 2'-NH$_2$ ribonucleotide 2'-NH(C$_1$–C$_2$ alkyl) ribonucleotide, 2'-N(C$_1$–C$_2$ alkyl)$_2$ ribonucleotide, 2'-CH$_2$F ribonucleotide, 2'-CHF$_2$ ribonucleotide, 2'-CF$_3$ ribonucleotide, 2'=CH$_2$ ribonucleotide, 2'=CHF ribonucleotide, 2'=CF$_2$ ribonucleotide, 2'-C$_2$H$_5$ ribonucleotide, 2'-CH=CH$_2$ ribonucleotide, 2'-C—CH ribonucleotide. A further useful ribonucleotide is one having a ring located on the ribose ring in a cage-like structure including 3',O,4'-C-methyleneribonucleotides. Such cage-like structures will physically fix the ribose ring in the desired conformation.

Additionally, preferred for use as the B-form nucleotides for eliciting RNase H are arabino nucleotides having 2'-deoxy-2'-cyano, 2'-deoxy-2'-fluoro, 2'-deoxy-2'-chloro, 2'-deoxy-2'-bromo, 2'-deoxy-2'-azido, 2'-methoxy and the unmodified arabino nucleotide (that includes a 2'-OH projecting upwards towards the base of the nucleotide). These arabino nucleotides can alternately be described as 2'-CN arabino nucleotide, 2'-F arabino nucleotide, 2'-Cl arabino nucleotide, 2'-Br arabino nucleotide, 2'-N$_3$ arabino nucleotide, 2'-O—CH$_3$ arabino nucleotide and arabino nucleotide.

Such nucleotides are linked together via phosphorothioate, phosphorodithioate, boranophosphate or phosphodiester linkages, particularly preferred is the phosphorothioate linkage.

Illustrative of the B-form nucleotides for use in the invention is a 2'-S-methyl (2'-SMe) nucleotide that resides in C2' endo conformation. It can be compared to 2'-O-methyl (2'-OMe)nucleotides that resides in a C3' endo conformation. Particularly suitable for use in comparing these two nucleotides are molecular dynamic investigations using a SGI [Silicon Graphics, Mountain View, Calif.] computer and the AMBER [UCSF, San Francisco, Calif.] modeling software package for computer simulations.

Ribose conformations in C2'-modified nucleosides containing S-methyl groups were examined. To understand the influence of 2'-O-methyl and 2'-S-methyl groups on the conformation of nucleosides, we evaluated the relative energies of the 2'-O— and 2'-S-methylguanosine, along with normal deoxyguanosine and riboguanosine, starting from both C2'-endo and C3'-endo conformations using ab initio quantum mechanical calculations. All the structures were fully optimized at HF/6–31G* level and single point energies with electron-correlation were obtained at the MP2/6–31G*//HF/6–31G* level. As shown in Table 1, the C2'-endo conformation of deoxyguanosine is estimated to be 0.6 kcal/mol more stable than the C3'-endo conformation in the gas-phase. The conformational preference of the C2'-endo over the C3'-endo conformation appears to be less dependent upon electron correlation as revealed by the MP2/6–31G*//HF/6–31G* values which also predict the same difference in energy. The opposite trend is noted for riboguanosine. At the HF/6–31G* and MP2/6–31G*//HF/6–3 1G* levels, the C3'-endo form of riboguanosine is shown to be about 0.65 and 1.41 kcal/mol more stable than the C2'endo form, respectively.

TABLE 1

Relative energies* of the C3'-endo and C2'-endo conformations of representative nucleosides.

|  | HF/6-31G | MP2/6-31-G | CONTINUUM MODEL | AMBER |
| --- | --- | --- | --- | --- |
| dG | 0.60 | 0.56 | 0.88 | 0.65 |
| rG | −0.65 | −1.41 | −0.28 | −2.09 |
| 2'-O-MeG | −0.89 | −1.79 | −0.36 | −0.86 |
| 2'-S-MeG | 2.55 | 1.41 | 3.16 | 2.43 |

*energies are in kcal/mol relative to the C2'-endo conformation

Table 1 also includes the relative energies of 2'-O-methylguanosine and 2'-S-methylguanosine in C2'-endo and C3'-endo conformation. This data indicates the electronic nature of C2'-substitution has a significant impact on the relative stability of these conformations. Substitution of the 2'-O-methyl group increases the preference for the C3'-endo conformation (when compared to riboguanosine) by about 0.4 kcal/mol at both the HF/6–31G* and MP2/6–31G*//HF/6–31G* levels. In contrast, the 2'-S-methyl group reverses the trend. The C2'-endo conformation is favored by about 2.6 kcal/mol at the HF/6–31G* level, while the same difference is reduced to 1.41 kcal/mol at the MP2/6–31G*//HF/6–31G* level. For comparison, and also to evaluate the accuracy of the molecular mechanical force-field parameters used for the 2'-O-methyl and 2'-S-methyl substituted nucleosides, we have calculated the gas phase energies of the nucleosides. The results reported in Table 1 indicate that the calculated relative energies of these nucleosides compare qualitatively well with the ab initio calculations.

Additional calculations were also performed to gauge the effect of solvation on the relative stability of nucleoside conformations. The estimated solvation effect using HF/6–31G* geometries confirms that the relative energetic preference of the four nucleosides in the gas-phase is maintained in the aqueous phase as well (Table 1). Solvation effects were also examined using molecular dynamics simulations of the nucleosides in explicit water. From these trajectories, one can observe the predominance of C2'-endo conformation for deoxyriboguanosine and 2'-S-methylriboguanosine while riboguanosine and 2'-O-methylriboguanosine prefer the C3'-endo conformation. These results are in much accord with the available NMR results on 2'-S-methylribonucleosides. NMR studies of sugar puckering equilibrium using vicinal spin-coupling constants have indicated that the conformation of the sugar ring in 2'-S-methylpyrimidine nucleosides show an average of >75% S-character, whereas the corresponding purine analogs exhibit an average of >90% S-pucker [Fraser, A., Wheeler, P., Cook, P. D. and Sanghvi, Y. S., *J. Heterocycl. Chem.*, 1993, 30, 1277–1287]. It was observed that the 2'-S-methyl substitution in deoxynucleoside confers more conformational rigidity to the sugar conformation when compared with deoxyribonucleosides.

Structural features of DNA:RNA, OMe_DNA:RNA and SMe_DNA:RNA hybrids were also observed. The average RMS deviation of the DNA:RNA structure from the starting hybrid coordinates indicate the structure is stabilized over the length of the simulation with an approximate average RMS deviation of 1.0 Å. This deviation is due, in part, to inherent differences in averaged structures (i.e. the starting conformation) and structures at thermal equilibrium. The changes in sugar pucker conformation for three of the central base pairs of this hybrid are in good agreement with the observations made in previous NMR studies. The sugars in the RNA strand maintain very stable geometries in the C3'-endo conformation with ring pucker values near 0°. In contrast, the sugars of the DNA strand show significant variability.

The average RMS deviation of the OMe_DNA:RNA is approximately 1.2 Å from the starting A-form conformation; while the SMe_DNA:RNA shows a slightly higher deviation (approximately 1.8 Å) from the starting hybrid conformation. The SMe_DNA strand also shows a greater variance in RMS deviation, suggesting the S-methyl group may induce some structural fluctuations. The sugar puckers of the RNA complements maintain C3'-endo puckering throughout the simulation. As expected from the nucleoside calculations, however, significant differences are noted in the puckering of the OMe_DNA and SMe_DNA strands, with the former adopting C3'-endo, and the latter, C1'-exo/C2'-endo conformations.

An analysis of the helicoidal parameters for all three hybrid structures has also been performed to further characterize the duplex conformation. Three of the more important axis-basepair parameters that distinguish the different forms of the duplexes, X-displacement, propeller twist, and inclination, are reported in Table 2. Usually, an X-displacement near zero represents a B-form duplex; while a negative displacement, which is a direct measure of deviation of the helix from the helical axis, makes the structure appear more A-like in conformation. In A-form duplexes, these values typically vary from −4 Å to −5 Å. In comparing these values for all three hybrids, the SMe_DNA:RNA hybrid shows the most deviation from the A-form value, the OMe_DNA:RNA shows the least, and the DNA:RNA is intermediate. A similar trend is also evident when comparing the inclination and propeller twist values with ideal A-form parameters. These results are further supported by an analysis of the backbone and glycosidic torsion angles of the hybrid structures. Glycosidic angles (X) of A-form geometries, for example, are typically near −159° while B form values are near −102°. These angles are found to be −162°, −133°, and −108° for the OMe_DNA, DNA, and SMe_DNA strands, respectively. All RNA complements adopt an X angle close to −160°. In addition, "crankshaft" transitions were also noted in the backbone torsions of the central UpU steps of the RNA strand in the SMe_DNA:RNA and DNA;RNA hybrids. Such transitions suggest some local conformational changes may occur to relieve a less favorable global conformation. Taken overall, the results indicate the amount of A-character decreases as OMe_DNA:RNA>DNA:RNA>SMe_DNA:RNA, with the latter two adopting more intermediate conformations when compared to A- and B-form geometries.

TABLE 2

Average helical parameters derived from the last 500 ps of simulation time. (canonical A-and B-form values are given for comparison)

| Helicoidal Parameter | B-DNA (x-ray) | B-DNA (fibre) | A-DNA (fibre) | DNA:RNA | OMe_DNA:RNA | SMe_DNA:RNA |
|---|---|---|---|---|---|---|
| X-disp | 1.2 | 0.0 | −5.3 | −4.5 | −5.4 | −3.5 |
| Inclination | −2.3 | 1.5 | 20.7 | 11.6 | 15.1 | 0.7 |
| Propeller | −16.4 | −13.3 | −7.5 | −12.7 | −15.8 | −10.3 |

Stability of C2'-modified DNA:RNA hybrids was determined. Although the overall stability of the DNA:RNA hybrids depends on several factors including sequence-dependencies and the purine content in the DNA or RNA strands DNA:RNA hybrids are usually less stable than RNA:RNA duplexes and, in some cases, even less stable than DNA:DNA duplexes. Available experimental data attributes the relatively lowered stability of DNA:RNA hybrids largely to its intermediate conformational nature between DNA:DNA (B-family) and RNA:RNA (A-family) duplexes. The overall thermodynamic stability of nucleic acid duplexes may originate from several factors including the conformation of backbone, base-pairing and stacking interactions. While it is difficult to ascertain the individual thermodynamic contributions to the overall stabilization of the duplex, it is reasonable to argue that the major factors that promote increased stability of hybrid duplexes are better stacking interactions (electrostatic π-π_interactions) and more favorable groove dimensions for hydration. The C2'-S-methyl substitution has been shown to destabilize the hybrid duplex. The notable differences in the rise values among the three hybrids may offer some explanation. While the 2'-S-methyl group has a strong influence on decreasing the base-stacking through high rise values (~3.2 Å), the 2'-O-methyl group makes the overall structure more compact with a rise value that is equal to that of A-form duplexes (~2.6 Å). Despite its overall A-like structural features, the SMe_DNA:RNA hybrid structure possesses an average rise value of 3.2 Å which is quite close to that of B-family duplexes. In fact, some local base-steps (CG steps) may be observed to have unusually high rise values (as high as 4.5 Å). Thus, the greater destabilization of 2'-S-methyl substituted DNA:RNA hybrids may be partly attributed to poor stacking interactions.

It has been postulated that RNase H binds to the minor groove of RNA:DNA hybrid complexes, requiring an intermediate minor groove width between ideal A- and B-form geometries to optimize interactions between the sugar phosphate backbone atoms and RNase H. A close inspection of the averaged structures for the hybrid duplexes using computer simulations reveals significant variation in the minor groove width dimensions as shown in Table 3. Whereas the O-methyl substitution leads to a slight expansion of the minor groove width when compared to the standard DNA:RNA complex, the S-methyl substitution leads to a general contraction (approximately 0.9 Å). These changes are most likely due to the preferred sugar puckering noted for the antisense strands which induce either A- or B-like single strand conformations. In addition to minor groove variations, the results also point to potential differences in the steric makeup of the minor groove. The O-methyl group points into the minor groove while the S-methyl is directed away towards the major groove. Essentially, the S-methyl group has flipped through the bases into the major groove as a consequence of C2'-endo puckering.

TABLE 3

Minor groove widths averaged over the last 500 ps of simulation time

| Phosphate Distance | DNA: RNA | OMe_DNA: RNA | SMe_DNA: RNA | DNA: RNA (B-form) | RNA: RNA (A-form) |
|---|---|---|---|---|---|
| P5–P20 | 15.27 | 16.82 | 13.73 | 14.19 | 17.32 |
| P6–P19 | 15.52 | 16.79 | 15.73 | 12.66 | 17.12 |
| P7–P18 | 15.19 | 16.40 | 14.08 | 11.10 | 16.60 |
| P8–P17 | 15.07 | 16.12 | 14.00 | 10.98 | 16.14 |
| P9–P16 | 15.29 | 16.25 | 14.98 | 11.65 | 16.93 |
| P10–P15 | 15.37 | 16.57 | 13.92 | 14.05 | 17.69 |

In addition to the modifications described above, the nucleotides of the oligonucleotides of the invention can have a variety of other modification so long as these other modifications do not significantly detract from the properties described above. Thus, for nucleotides that are incorporated into oligonucleotides of the invention, these nucleotides can have sugar portions that correspond to naturally-occurring sugars or modified sugars. Representative modified sugars include carbocyclic or acyclic sugars, sugars having substituent groups at their 2' position, sugars having substituent groups at their 3' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such oligonucleotides are best described as being structurally distinguishable from, yet functionally interchangeable with, naturally occurring or synthetic wild type oligonucleotides. All such oligonucleotides are comprehended by this invention so long as they function effectively to mimic the structure of a desired RNA or DNA strand. A class of representative base modifications include tricyclic cytosine analog, termed "G clamp" (Lin, et al., *J. Am. Chem. Soc.* 1998,120,8531). This analog makes four hydrogen bonds to a complementary guanine (G) within a helix by simultaneously recognizing the Watson-Crick and Hoogsteen faces of the targeted G. This G clamp modification when incorporated into phosphorothioate oligonucleotides, dramatically enhances antisense potencies in cell culture. The oligonucleotides of the invention also can include phenoxazine-substituted bases of the type disclosed by Flanagan, et al., *Nat. Biotechnol.* 1999, 17(1), 48–52.

Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995,36, 3651), a palmityl moiety (Mishra et al., *Biochim. Biophys. Acta,* 1995,1264,229), or an octadecylamine or hexylamino-carbonyl-oxycholesterol moiety (Crooke et al., *J. Pharmacol. Exp. Ther.,* 1996, 277, 923).

As used herein, the term "alkyl" includes but is not limited to straight chain, branch chain, and cyclic unsaturated hydrocarbon groups including but not limited to methyl, ethyl, and isopropyl groups. Alkyl groups of the present invention may be substituted. Representative alkyl substituents are disclosed in U.S. Pat. No. 5,212,295, at column 12, lines 41–50, hereby incorporated by reference in its entirety.

Alkenyl groups according to the invention are to straight chain, branch chain, and cyclic hydrocarbon groups containing at least one carbon—carbon double bond, and alkynyl groups are to straight chain, branch chain, and cyclic hydrocarbon groups containing at least one carbon—carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

In general, the term "hetero" denotes an atom other than carbon, preferably but not exclusively N, O, or S. Accordingly, the term "heterocyclic ring" denotes a carbon-based ring system having one or more heteroatoms (i.e., non-carbon atoms). Preferred heterocyclic rings include, for example but not limited to imidazole, pyrrolidine, 1,3-dioxane, piperazine, morpholine rings. As used herein, the term "heterocyclic ring" also denotes a ring system having one or more double bonds, and one or more heteroatoms. Preferred heterocyclic rings include, for example but not limited to the pyrrolidino ring.

Oligonucleotides according to the present invention that are hybridizable to a target nucleic acid preferably comprise from about 5 to about 50 nucleosides. It is more preferred that such compounds comprise from about 8 to about 30 nucleosides, with 15 to 25 nucleosides being particularly preferred. As used herein, a target nucleic acid is any nucleic acid that can hybridize with a complementary nucleic acid-like compound. Further in the context of this invention, "hybridization" shall mean hydrogen bonding, which may be Watson-Crick, Hoogsteen or reversed Hoogsteen hydrogen bonding between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

The oligonucleotides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

Some representative therapeutic indications and other uses for the compounds of the invention are as follows:

One therapeutic indication of particular interest is psoriasis. Psoriasis is a common chronic and recurrent disease characterized by dry, well-circumscribed, silvery, scaling papules and plaques of various sizes. The disease varies in severity from a few lesions to widespread dermatosis with disabling arthritis or exfoliation. The ultimate cause of psoriasis is not known, but the thick scaling that occurs is probably due to increased epidermal cell proliferation (*The Merck Manual of Diagnosis and Therapy*, 15th Ed., pp.2283–2285, Berkow et al., eds., Rahway, N.J., 1987). Inhibitors of Protein Kinase C (PKC) have been shown to have both antiproliferative and anti-inflammatory effects in vitro. Some antipsoriasis drugs, such as cyclosporin A and anthralin, have been shown to inhibit PKC, and inhibition of PKC has been suggested as a therapeutic approach to the treatment of psoriasis (Hegemann, L. and G. Mahrle, *Pharmacology of the Skin*, H. Mukhtar, ed., pp. 357–368, CRC Press, Boca Raton, Fla., 1992). Antisense compounds targeted to Protein Kinase C (PKC) proteins are described in U.S. Pat. Nos. 5,620,963 to Cook et al. and 5,681,747 to Boggs et al.

Another type of therapeutic indication of interest is inflammatory disorders of the skin. These occur in a variety of forms including, for example, lichen planus, toxic epidermal necrolyis (TEN), ertyhema multiforme and the like (*The Merck Manual of Diagnosis and Therapy*, 15th Ed., pp. 2286–2292, Berkow et al., eds., Rahway, N.J., 1987). Expression of ICAM-1 has been associated with a variety of inflammatory skin disorders such as allergic contact dermatitis, fixed drug eruption, lichen planus and psoriasis (Ho et al., *J. Am. Acad. Dermatol.*, 1990, 22, 64; Griffiths et al., *Am. J. Pathology*, 1989,135,1045; Lisby et al., *Br. J. Dermatol.*, 1989,120,479; Shiohara et al., *Arch. Dermatol.*, 1989, 125, 1371; Regezi et al., *Oral Surg. Oral Med. Oral Pathol.*, 1996, 81, 682). Moreover, intraperitoneal administration of a monoclonal antibody to ICAM-1 decreases ovalbumin-induced eosinophil infiltration into skin in mice (Hakugawa et al., *J. Dermatol.*, 1997, 24, 73). Antisense compounds targeted to ICAM-1 are described in U.S. Pat. Nos. 5,514,788 and 5,591,623, and co-pending U.S. patent application Ser. Nos. 09/009,490 now U.S. Pat. No. 6,400, 391 and 09/062,416 now U.S. Pat. No. 6,111,084, Jan. 20, 1998 and Apr. 17, 1998, respectively, all to Bennett et al.

Other antisense targets for skin inflammatory disorders are VCAM-1 and PECAM-1. Intraperitoneal administration of a monoclonal antibody to VCAM-1 decreases ovalbumin-induced eosinophil infiltration into the skin of mice (Hakugawa et al., *J. Dermatol.*, 1997, 24, 73). Antisense compounds targeted to VCAM-1 are described in U.S. Pat. Nos. 5,514,788 and 5,591,623. PECAM-1 proteins are glycoproteins which are expressed on the surfaces of a variety of cell types (for reviews, see Newman, *J. Clin. Invest.*, 1997, 99, 3 and DeLisser et al., *Immunol. Today*, 1994, 15, 490). In addition to directly participating in cell—cell interactions, PECAM-1 apparently also regulates the activity and/or expression of other molecules involved in cellular interactions (Litwin et al., *J. Cell Biol.*, 1997, 139, 219) and is thus a key mediator of several cell:cell interactions. Antisense compounds targeted to PECAM-1 are described in co-pending U.S. patent application Ser. No. 09/044,506 now U.S. Pat. No. 5,955,443, filed Mar. 19, 1998, by Bennett et al.

Another type of therapeutic indication of interest for oligonucleotides encompasses a variety of cancers of the skin. Representative skin cancers include benign tumors (warts, moles and the like) and malignant tumors such as, for example, basal cell carcinoma, squamous cell carcinoma, malignant melanoma, Paget's disease, Kaposi's sarcoma and the like (*The Merci Manual of Diagnosis and Therapy,*

15th Ed., pp.2301–2310, Berkow et al., eds., Rahway, N.J., 1987). A number of molecular targets involved in tumorigenesis, maintenance of the hyperproliferative state and metastasis are targeted to prevent or inhibit skin cancers, or to prevent their spread to other tissues.

The ras oncogenes are guanine-binding proteins that have been implicated in cancer by, e.g., the fact that activated ras oncogenes have been found in about 30% of human tumors generally; this figure approached 100% in carcinomas of the exocrine pancreas (for a review, see Downward, *Trends in Biol. Sci.,* 1990, 15,469). Antisense compounds targeted to H-ras and K-ras are described in U.S. Pat. Nos. 5,582,972 to Lima et al., 5,582,986 to Monia et al. and 5,661,134 to Cook et al., and in published PCT application WO 94/08003.

Protein Kinase C (PKC) proteins have also been implicated in tumorigenesis. Antisense compounds targeted to Protein Kinase C (PKC) proteins are described in U.S. Pat. Nos. 5,620,963 to Cook et al. and 5,681,747 to Boggs et al. Also of interest are AP-1 subunits and JNK proteins, particularly in regard to their roles in tumorigenesis and metastasis. The process of metastasis involves a sequence of events wherein (1) a cancer cell detaches from its extracellular matrices, (2) the detached cancer cell migrates to another portion of an animal's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.,* 1996,275, 72). However, many human tumors have elevated levels of activity of one or more matrix metalloproteinases (MMPs) (Stetler-Stevenson et al., *Annu. Rev. Cell Biol.,* 1993, 9,541; Bernhard et al., *Proc. Natl. Acad. Sci. (U.S.A.),* 1994, 91, 4293. The MMPs are a family of enzymes which have the ability to degrade components of the extracellular matrix (Birkedal-Hansen, *Current Op. Biol.,* 1995, 7, 728). In particular, one member of this family, matrix metalloproteinase-9 (MMP-9), is often found to be expressed only in tumors and other diseased tissues (Himelstein et al., *Invasion & Metastasis,* 1994, 14, 246).

Several studies have shown that regulation of the MMP-9 gene may be controlled by the AP-1 transcription factor (Kerr et al., *Science,* 1988, 242, 1242; Kerr et al., *Cell,* 1990, 61, 267; Gum et al., *J. Biol. Chem.,* 1996, 271, 10672; Hua et al., *Cancer Res.,* 1996, 56, 5279). Inhibition of AP-1 function has been shown to attenuate MMP-9 expression (U.S. patent application Ser. No. 08/837,201 now U.S. Pat. No. 5,985,558). AP-1 is a heterodimeric protein having two subunits, the gene products of fos and jun. Antisense compounds targeted to c-fos and c-jun are described in co-pending U.S. patent application Ser. No. 08/837,201 now U.S. Pat. No. 5,985,558, filed Mar. 14, 1997, by Dean et al.

Furthermore, AP-1 is itself activated in certain circumstances by phosphorylation of the Jun subunit at an amino-terminal position by Jun N-terminal kinases (JNKs). Thus, inhibition of one or more JNKs is expected to result in decreased AP-1 activity and, consequentially, reduced MMP expression. Antisense compounds targeted to JNKs are described in co-pending U.S. patent application Ser. No. 08/910,629 now U.S. Pat. No. 5,877,309, filed Aug. 13, 1997, by Dean et al.

Infectious diseases of the skin are caused by viral, bacterial or fungal agents. In the case of Lyme disease, the tick borne causative agent thereof, the spirochete *Borrelia burgdorferi,* up-regulates the expression of ICAM-1, VCAM-1 and ELAM-1 on endothelial cells in vitro (Boggemeyer et al., *Cell Adhes. Comm.,* 1994, 2, 145).

Furthermore, it has been proposed that the mediation of the disease by the anti-inflammatory agent prednisolone is due in part to mediation of this up-regulation of adhesion molecules (Hurtenbach et al., *Int. J. Immunopharmac.,* 1996, 18, 281). Thus, potential targets for therapeutic mediation (or prevention) of Lyme disease include ICAM-1, VCAM-1 and ELAM-1 (supra).

Other infectious disease of the skin which are tractable to treatment using the compositions and methods of the invention include disorders resulting from infection by bacterial, viral or fungal agents (*The Merck Manual of Diagnosis and Therapy,* 15th Ed., pp. 2263–2277, Berkow et al., eds., Rahway, N.J., 1987). With regards to infections of the skin caused by fungal agents, U.S. Pat. No. 5,691,461 provides antisense compounds for inhibiting the growth of *Candida albicans.*

With regards to infections of the skin caused by viral agents, U.S. Pat. Nos. 5,166,195, 5,523,389 and 5,591,600 provide oligonucleotide inhibitors of Human Immunodeficiency Virus (HIV). U.S. Pat. No. 5,004,810 provides oligomers capable of hybridizing to herpes simplex virus Vmw65 mRNA and inhibiting its replication. U.S. Pat. Nos. 5,194,428 and 5,580,767 provide antisense compounds having antiviral activity against influenza virus. U.S. Pat. No. 4,806,463 provides antisense compounds and methods using them to inhibit HTLV-III replication. U.S. Pat. Nos. 4,689,320, 5,442,049, 5,591,720 and 5,607,923 are directed to antisense compounds as antiviral agents specific to cytomegalovirus (CMV). U.S. Pat. No. 5,242,906 provides antisense compounds useful in the treatment of latent Epstein-Barr virus (EBV) infections. U.S. Pat. Nos. 5,248,670, 5,514,577 and 5,658,891 provide antisense compounds useful in the treatment of herpes virus infections. U.S. Pat. Nos. 5,457,189 and 5,681,944 provide antisense compounds useful in the treatment of papilloma virus infections. The antisense compounds disclosed in these patents, which are herein incorporated by reference, may be used with the compositions of the invention to effect prophylactic, palliative or therapeutic relief from diseases caused or exacerbated by the indicated pathogenic agents.

Antisense oligonucleotides employed in the compositions of the present invention may also be used to determine the nature, function and potential relationship of various genetic components of the body to disease or body states in animals. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences,* 1994, 15, 250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. Antisense oligonucleotides have been systemically administered to rats in order to study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., *Nature,* 1993, 363:260; Dean et al., *Proc. Natl. Acad. Sci. U.S.A.,* 1994, 91:11762; and Wahlestedt et al., *Science,* 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.,* 1994,15:250). By providing compositions and methods for the simple non-parenteral delivery of oligonucleotides and other nucleic acids, the present invention overcomes these and other shortcomings.

The administration of therapeutic or pharmaceutical compositions comprising the oligonucleotides of the invention is believed to be within the skill of those in the art. In general, a patient in need of therapy or prophylaxis is administered a composition comprising a compound of the invention, commonly in a pharmaceutically acceptable carrier, in doses ranging from 0.01 ug to 100 g per kg of body weight depending on the age of the patient and the severity of the disorder or disease state being treated. Dosing is dependent on severity and responsiveness of the disease state to be treated, with the course of treatment lasting from several days to several months, or until a cure is effected or a diminution or prevention of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual antisense compounds, and can generally be estimated based on $EC_{50}s$ found to be effective in in vitro and in vivo animal models.

In the context of the invention, the term "treatment regimen" is meant to encompass therapeutic, palliative and prophylactic modalities of administration of one or more compositions of the invention. A particular treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the composition may either be increased in the event the patient does not respond significantly to current dosage levels, or the dose may be decreased if an alleviation of the symptoms of the disorder or disease state is observed, or if the disorder or disease state has been ablated.

An optimal dosing schedule is used to deliver a therapeutically effective amount of the oligonucleotide of the invention. The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs may vary, determination of optimal ranges for effective amounts of pharmaceutical compositions is within the skill of the art. Human doses can be extrapolated from animal studies (Katocs et al., Chapter 27 In: *Remington's Pharmaceutical Sciences,* 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: *Goodman & Gilman's The Pharmacological Basis of Therapeutics,* 9th Ed., Hardman et al., eds., McGraw-Hill, New York, N.Y., 1996).

Following successful treatment, it may be desirable to have the patient undergo maintenance therapy to prevent the recurrence of the disease state, wherein the bioactive agent is administered in maintenance doses, ranging from 0.01 ug to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 ug to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

Prophylactic modalities for high risk individuals are also encompassed by the invention. As used herein, the term "high risk individual" is meant to refer to an individual for whom it has been determined, via, e.g., individual or family history or genetic testing, that there is a significantly higher than normal probability of being susceptible to the onset or recurrence of a disease or disorder. For example, a subject animal could have a personal and/or family medical history that includes frequent occurrences of a particular disease or disorder. As another example, a subject animal could have had such a susceptibility determined by genetic screening according to techniques known in the art (see, e.g., U.S. Congress, Office of Technology Assessment, Chapter 5 In: *Genetic Monitoring and Screening in the Workplace,* OTA-BA-455, U.S. Government Printing Office, Washington, D.C., 1990, pages 75–99). As part of a treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compared to the effect observed when a second pharmaceutical composition lacking the active agent is administered to a similarly situated individual.

For therapeutic use the oligonucleotide analog is administered to an animal suffering from a disease modulated by some protein. It is preferred to administer to patients suspected of suffering from such a disease an amount of oligonucleotide analog that is effective to reduce the symptomology of that disease. One skilled in the art can determine optimum dosages and treatment schedules for such treatment regimens.

For use in diseases modulated by protein that portion of DNA or RNA which codes for the protein whose formation or activity is to be modulated is targeted. The targeting portion of the composition to be employed is, thus, selected to be complementary to the preselected portion of DNA or RNA, that is to be an antisense oligonucleotide for that portion.

It is generally preferred to administer the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

This invention is also directed to methods for the selective binding of RNA for research and diagnostic purposes wherein it is useful to effect strand cleavage utilizing enzymatic RNase H cleavage while concurrently effecting modulation of binding affinity and or nuclease resistance. Such selective is accomplished by interacting such RNA or DNA with compositions of the invention which are resistant to degradative nucleases and which hybridize more strongly and with greater fidelity than known oligonucleotides or oligonucleotide analogs.

Oligonucleotides according to the invention can be assembled in solution or through solid-phase reactions, for example, on a suitable DNA synthesizer utilizing nucleosides, phosphoramidites and derivatized controlled pore glass (CPG) according to the invention and/or standard nucleotide precursors. In addition to nucleosides that include a novel modification of the inventions other nucleoside within an oligonucleotide may be further modified with other modifications at the 2' position. Precursor nucleoside and nucleotide precursors used to form such additional modification may carry substituents either at the 2' or 3' positions. Such precursors may be synthesized according to the present invention by reacting appropriately protected nucleosides bearing at least one free 2' or 3' hydroxyl group with an appropriate alkylating agent such as, but not limited to, alkoxyalkyl halides, alkoxylalkylsulfonates, hydroxyalkyl halides, hydroxyalkyl sulfonates, aminoalkyl halides, aminoalkyl sulfonates, phthalimidoalkyl halides, phthalimidoalkyl sulfonates, alkylaminoalkyl halides, alkylaminoalkyl sulfonates, dialkylaminoalkyl halides, dialkylaminoalkylsulfonates, dialkylaminooxyalkyl halides, dialkylaminooxyalkyl sulfonates and suitably protected versions of the same. Preferred halides used for alkylating reactions include chloride, bromide, fluoride and iodide. Preferred sulfonate leaving groups used for alkylating reactions include, but are not limited to, benzenesulfonate, methylsulfonate, tosylate, p-bromobenzenesulfonate, triflate, trifluoroethylsulfonate, and (2,4-dinitroanilino) benzenesulfonate.

Suitably protected nucleosides can be assembled into oligonucleotides according to known techniques. See, for example, Beaucage et al., *Tetrahedron*, 1992, 48, 2223.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands. The structure-stability relationships of a large number of nucleic acid modifications have been reviewed (Freier and Altmann, *Nucl. Acids Research*, 1997, 25, 4429–443).

The relative binding ability of the oligonucleotides of the present invention was determined using protocols as described in the literature (Freier and Altmann, *Nucl. Acids Research*, 1997, 25, 4429–443). Typically absorbance versus temperature curves were determined using samples containing 4 uM oligonucleotide in 100 mM Na+, 10 mM phosphate, 0.1 mM EDTA, and 4 uM complementary, length matched RNA.

The in vivo stability of oligonucleotides is an important factor to consider in the development of oligonucleotide therapeutics. Resistance of oligonucleotides to degradation by nucleases, phosphodiesterases and other enzymes is therefore determined. Typical in vivo assessment of stability of the oligonucleotides of the present invention is performed by administering a single dose of 5 mg/kg of oligonucleotide in phosphate buffered saline to BALB/c mice. Blood collected at specific time intervals post-administration is analyzed by HPLC or capillary gel electrophoresis (CGE) to determine the amount of oligonucleotide remaining intact in circulation and the nature the of the degradation products.

Heterocyclic bases amenable to the present invention include both naturally and non-naturally occurring nucleobases and heterocycles. A representative list includes adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further heterocyclic bases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch, et al., *Angewandte Chemie, International Edition* 1991, 30, 613.

Additional objects, advantages, and novel features of this invention will become apparent to those skilled in the art upon examination of the following examples, which are not intended to be limiting. All oligonucleotide sequences are listed in a standard 5' to 3' order from left to right.

EXAMPLE 1

5'-O-DMT-2'-O-(2-methoxyethyl)-5-methyl uridine and 5'-O-DMT-3'-O-(2-methoxyethyl)$_5$-methyl Uridine 2',3'-O-dibutylstannylene 5-methyl uridine (345 g) (prepared as per: Wagner et al., *J. Org. Chem.*, 1974, 39, 24) was alkylated with 2-methoxyethyl bromide (196 g) in the presence of tetrabutylammonium iodide (235 g) in DMF (3 L) at 70° C. to give a mixture of 2'-O— and 3'-O-(2-methoxyethyl)-5-methyl uridine (150 g) in nearly 1:1 ratio of isomers. The mixture was treated with DMT chloride (110 g, DMT-Cl) in pyridine (1 L) to give a mixture of the 5'-O-DMT-nucleosides. After the standard work-up the isomers were separated by silica gel column chromatography. The 2'-isomer eluted first, followed by the 3'-isomer.

EXAMPLE 2

5'-O-DMT-3'-O-(2-methoxyethyl)-5-methyl-uridine-2'-O-(2-cyanoethyl-N,N-diisopropyl) Phosphoramidite 5'-O-DMT-3'-O-(2-methoxyethyl)-5-methyluridine (5 g, 0.008 mol) was dissolved in $CH_2Cl_2$ (30 mL) and to this solution, under argon, diisopropylaminotetrazolide (0.415 g) and 2-cyanoethoxy-N,N-diisopropyl phosphoramidite (3.9 mL) were added. The reaction was stirred overnight. The solvent was evaporated and the residue was applied to silica column and eluted with ethyl acetate to give 3.75 g title compound.

EXAMPLE 3

5'-O-DMT-3'-O-(2-methoxyethyl)-N$^4$-benzoyl-5-methyl-cytidine

5'-O-DMT-3'-O-(2-methoxyethyl)-5-methyl uridine (15 g) was treated with 150 mL anhydrous pyridine and 4.5 mL of acetic anhydride under argon and stirred overnight. Pyridine was evaporated and the residue was partitioned between 200 mL of saturated NaHCO$_3$ solution and 200 mL of ethylacetate. The organic layer was dried (anhydrous MgSO$_4$) and evaporated to give 16 g of 2'-acetoxy-5'-O-(DMT)-3'-O-(2-methoxyethyl)-5-methyl uridine.

To an ice-cold solution of triazole (19.9 g) in triethylamine (50 mL) and acetonitrile (150 mL), with mechanical stirring, 9 mL of POCl$_3$ was added dropwise. After the addition, the ice bath was removed and the mixture stirred for 30 min. The 2'-acetoxy-5'-O-(DMT)-3'-O-(2-methoxyethyl)-5-methyl uridine (16 g in 50 mL CH$_3$CN) was added dropwise to the above solution with the receiving flask kept at ice bath temperatures. After 2 hrs, TLC indicated a faster moving nucleoside, C-4-triazole-derivative. The reaction flask was evaporated and the nucleoside was partitioned between ethylacetate (500 mL) and NaHCO$_3$ (500 mL). The organic layer was washed with saturated NaCl solution, dried (anhydrous NgSO$_4$) and evaporated to give 15 g of C-4-triazole nucleoside. This compound was then dissolved in 2:1 mixture of NH$_4$OH/dioxane (100 mL:200 mL) and stirred overnight. TLC indicated disappearance of the starting material. The solution was evaporated and dissolved in methanol to crystallize out 9.6 g of 5'-O-(DMT)-3'-O-(2-methoxyethyl)$_5$-methyl cytidine.

5'-O-DMT-3'-O-(2-methoxyethyl)-5-methyl cytidine (9.6 g, 0.015 mol) was dissolved in 50 mL of DMF and treated with 7.37 g of benzoic anhydride. After 24 hrs of stirring, DMF was evaporated and the residue was loaded on silica column and eluted with 1:1 hexane:ethylacetate to give the desired nucleoside.

EXAMPLE 4

5'-O-DMT-3'-O-(2-methoxyethyl)-N$^4$-benzoyl-5-methyl-cytidine-2'-O-(2-cyanoethyl-N,N-diisopropyl) Phosphoramidite 5'-O-DMT-3'-O-(2-methoxyethyl)-N$^4$-benzoyl-5-methyl-cytidine-2'-O-(2-cyanoethyl-N,N-diisopropyl) phosphoramidite was obtained from the above nucleoside using the phosphitylation protocol described for the corresponding 5-methyl-uridine derivative.

EXAMPLE 5

N$^6$-Benzoyl-5'-O-(DMT)-3'-O-(2-methoxyethyl) Adenosine

A solution of adenosine (42.74 g, 0.16 mol) in dry dimethyl formamide (800 mL) at 5° C. was treated with sodium hydride (8.24 g, 60% in oil prewashed thrice with hexanes, 0.21 mol). After stirring for 30 min, 2-methoxyethyl bromide (0.16 mol) was added over 20 min. The reaction was stirred at 5° C. for 8 h, then filtered through Celite. The filtrate was concentrated under reduced pressure followed by coevaporation with toluene (2×100 mL). The residue was adsorbed on silica gel (100 g) and chromatographed (800 g, chloroform-methanol 9:14:1). Selected fractions were concentrated under reduced pressure and the residue was a mixture of 2'-O-(2-(methoxyethyl) adenosine and 3'-O-(2-methoxyethyl) adenosine in the ratio of 4:1.

The above mixture (0.056 mol) in pyridine (100 mL) was evaporated under reduced pressure to dryness. The residue was redissolved in pyridine (560 mL) and cooled in an ice water bath. Trimethylsilyl chloride (36.4 mL, 0.291 mol) was added and the reaction was stirred at 5° C. for 30 min. Benzoyl chloride (33.6 mL, 0.291 mol) was added and the reaction was allowed to warm to 25° C. for 2 h and then cooled to 5° C. The reaction was diluted with cold water (112 mL) and after stirring for 15 min, concentrated ammonium hydroxide (112 Ml) was added. After 30 min, the reaction was concentrated under reduced pressure (below 30° C.) followed by coevaporation with toluene (2×100 mL). The residue was dissolved in ethyl acetate-methanol (400 mL, 9:1) and the undesired silyl by-products were removed by filtration. The filtrate was concentrated under reduced pressure and then chromatographed on silica gel (800 g, chloroform-methanol 9:1). Selected fractions were combined, concentrated under reduced pressure and dried at 25° C./0.2 mmHg for 2 h to give pure N$^6$-Benzoyl-2'-O-(2-methoxyethyl) adenosine and pure N$^6$-Benzoyl-3'-O-(2-methoxyethyl) adenosine.

A solution of N$^6$-Benzoyl-3'-O-(2-methoxyethyl) adenosine (11.0 g, 0.285 mol) in pyridine (100 mL) was evaporated under reduced pressure to an oil. The residue was redissolved in dry pyridine (300 mL) and DMT-Cl (10.9 g, 95%, 0.31 mol) was added. The mixture was stirred at 25° C. for 16 h and then poured onto a solution of sodium bicarbonate (20 g) in ice water (500 mL). The product was extracted with ethyl acetate (2×150 mL). The organic layer was washed with brine (50 mL), dried over sodium sulfate (powdered) and evaporated under reduced pressure (below 40 C). The residue was chromatographed on silica gel (400 g, ethyl acetate-acetonitrile-triethylamine 99:1:195:5:1). Selected fractions were combined, concentrated under reduced pressure and dried at 25° C./0.2 mmHg to give 16.8 g (73%) of the title compound as a foam. The TLC was homogenous.

EXAMPLE 6

[N$^6$-Benzoyl-5'-O-(DMT)-3'-O-(2-methoxyethyl) adenosin-2'-O-(2-cyanoethyl-N,N-diisopropyl) Phosphoramidite The title compound was prepared in the same manner as the 5-methyl-cytidine and 5-methyluridine analogs of Examples 2 and 4 by starting with the title compound of Example 5. Purification using ethyl acetate-hexanes-triethylamine 59:40:1 as the chromatography eluent gave 67% yield of the title compound as a solid foam. The TLC was homogenous. $^3$P-NMR (CDCl$_3$, H$_3$PO$_4$ std.) δ 147.89; 148.36 (diastereomers).

EXAMPLE 7

5'-O-(DMT)—N$^2$-isobutyryl-3'-O-(2-methoxyethyl) Guanosine

A. 2,6-Diaminopurine Riboside

To a 2 L stainless steel Parr bomb was added guanosine hydrate (100 g, 0.35 mol, Aldrich), hexamethyl) disilazane (320 mL, 1.52 mol, 4.4 eq.), trimethyl) silyl trifluoromethanesulfonate (8.2 mL), and toluene (350 mL). The bomb was sealed and partially submerged in an oil bath (170° C.; internal T 150° C., 150 psi) for 5 days. The bomb was cooled in a dry ice/acetone bath and opened. The contents were transferred with methanol (300 mL) to a flask and the solvent was evaporated under reduced pressure. Aqueous methanol (50%,1.2 L) was added. The resulting brown suspension was heated to reflux for 5 h. The suspension was concentrated under reduced pressure to one half volume in order to remove most of the methanol. Water (600 mL) was added and the solution was heated to reflux, treated with charcoal (5 g) and hot filtered through Celite. The solution was allowed to cool to 25° C. The resulting precipitate was collected, washed with water (200 mL) and dried at 90° C./0.2 mmHg for 5 h to give a constant weight of 87.4 g (89%) of tan, crystalline solid; mp 247° C. (shrinks), 255° C. (dec, lit. (1) mp 250–252° C.); TLC homogenous (Rf 0.50, isopropanol-ammonium hydroxide-water 16:3:1); PMR (DMSO), δ 5.73 (d, 2,2-NH$_2$), 5.78 (s, 1, H-1), 6.83 (br s, 2,6-NH$_2$).

B. 2'-O-(2-methoxyethyl)-2,6-diaminopurine Riboside and 3'-O-(2-methoxyethyl)-2,6-diaminopurine Riboside To a solution of 2,6-diaminopurine riboside (10.0 g, 0.035 mol) in dry dimethyl formamide (350 mL) at 0° C. under an argon atmosphere was added sodium hydride (60% in oil, 1.6 g, 0.04 mol). After 30 min., 2-methoxyethyl bromide (0.44 mol) was added in one portion and the reaction was stirred at 25° C. for 16 h. Methanol (10 mL) was added and the mixture was concentrated under reduced pressure to an oil (20 g). The crude product, containing a ratio of 4:1 of the 2'/3' isomers, was chromatographed on silica gel (500 g, chloroform-methanol 4:1). The appropriate fractions were combined and concentrated under reduced pressure to a semi-solid (12 g). This was triturated with methanol (50 mL) to give a white, hygroscopic solid. The solid was dried at 40° C./0.2 mmHg for 6 h to give a pure 2' product and the pure 3' isomer, which were confirmed by NMR.

C. 3'-O-2-(methoxyethyl)guanosine

With rapid stirring, 3'-O-(2-methoxyethyl)-2,6-diaminopurine riboside (0.078 mol) was dissolved in monobasic sodium phosphate buffer (0.1 M, 525 mL, pH 7.3–7.4) at 25° C. Adenosine deaminase (Sigma type II, 1 unit/mg, 350 mg) was added and the reaction was stirred at 25° C. for 60 h. The mixture was cooled to 5° C. and filtered. The solid was washed with water (2×25 mL) and dried at 60° C./0.2 mmHg for 5 h to give 10.7 g of first crop material. A second crop was obtained by concentrating the mother liquors under reduced pressure to 125 mL, cooling to 5° C., collecting the solid, washing with cold water (2×20 mL) and drying as above to give 6.7 g of additional material for a total of 15.4 g (31% from guanosine hydrate) of light tan solid; TLC purity 97%.

D. N$^2$-Isobutyryl-3'-O-2-(methoxyethyl)guanosine

To a solution of 3'-O-2-(methoxyethyl)guanosine (18.1 g, 0.0613 mol) in pyridine (300 mL) was added trimethyl silyl chloride (50.4 mL, 0.46 mol). The reaction was stirred at 25° C. for 16 h. Isobutyryl chloride (33.2 mL, 0.316 mol) was added and the reaction was stirred for 4 h at 25° C. The reaction was diluted with water (25 mL). After stirring for 30 min, ammonium hydroxide (concentrated, 45 mL) was added until pH 6 was reached. The mixture was stirred in a water bath for 30 min and then evaporated under reduced pressure to an oil. The oil was suspended in a mixture of ethyl acetate (600 mL) and water (100 mL) until a solution formed. The solution was allowed to stand for 17 h at 25° C. The resulting precipitate was collected, washed with ethyl acetate (2×50 mL) and dried at 60° C./0.2 mmHg for 5 h to give 16.1 g (85%) of tan solid; TLC purity 98%.

E. 5'-O-(DMT)—N$^2$-isobutyryl-3'-O-(2-methoxyethyl) Guanosine

A solution of N$^2$-Isobutyryl-3'-O-2-(methoxyethyl) guanosine (0.051 mol) in pyridine (150 mL) was evaporated under reduced pressure to dryness. The residue was redissolved in pyridine (300 mL) and cooled to 10–15° C. DMT-Cl (27.2 g, 95%, 0.080 mol) was added and the reaction was stirred at 25° C. for 16 h. The reaction was evaporated under reduced pressure to an oil, dissolved in a minimum of methylene chloride and applied on a silica gel column (500 g). The product was eluted with a gradient of methylene chloride-triethylamine (99:1) to methylene chloride-methanol-triethylamine (99:1:1). Selected fractions were combined, concentrated under reduced pressure and dried at 40° C./0.2 mmHg for 2 h to afford 15 g (15.5% from guanosine hydrate) of tan foam; TLC purity 98%.

EXAMPLE 8

[5'-O-(DMT)—N$^2$-isobutyryl-3'-O-(2-methoxyethyl) Guanosin-2'-O-(2-cyanoethyl-N,N-diisopropyl) Phosphoramidite The protected nucleoside from Example 7 (0.0486 mol) was placed in a dry 1 L round bottom flask containing a Teflon stir-bar. The flask was purged with argon. Anhydrous methylene chloride (400 mL) was cannulated into the flask to dissolve the nucleoside. Previously vacuum dried N,N-diisopropylaminohydrotetrazolide (3.0 g, 0.0174 mol) was added under argon. With stirring, bis-N,N-diisopropyl-aminocyanoethylphosphoramidite (18.8 g, 0.0689 mol) was added via syringe over 1 min (no exotherm noted). The reaction was stirred under argon at 25° C. for 16 h. After verifying the completion of the reaction by TLC, the reaction was transferred to a separatory funnel (1 L). The reaction flask was rinsed with methylene chloride (2×50 mL). The combined organic layer was washed with saturated aq. sodium bicarbonate (200 mL) and then brine (200 mL). The organic layer was dried over sodium sulfate (50 g, powdered) for 2 h. The solution was filtered and concentrated under reduced pressure to a viscous oil. The resulting phosphoramidite was purified by silica gel flash chromatography (800 g, ethyl acetate-triethylamine 99:1). Selected fractions were combined, concentrated under reduced pressure, and dried at 25 C./0.2 mmHg for 16 h to give 18.0 g (46%, 3% from guanosine hydrate) of solid foam TLC homogenous. $^3$P-NMR (CDCl$_3$, H$_3$PO$_4$ std.) δ 147.96; 148.20 (diastereomers).

EXAMPLE 9

5'-O-DMT-3'-O-(2-methoxyethyl)-5-methyl-uridine-2'-O-succinate

5'-O-DMT-3'-O-(2-methoxyethyl)-thymidine was first succinylated on the 2'-position. Thymidine nucleoside (4 mmol) was reacted with 10.2 mL dichloroethane, 615 mg (6.14 mmol) succinic anhydride, 570 μL (4.09 mmol) triethylamine, and 251 mg (2.05 mmol) 4-dimethylaminopyridine. The reactants were vortexed until dissolved and placed in heating block at 55° C. for approximately 30 minutes. Completeness of reaction checked by thin layer chromatography (TLC). The reaction mixture was washed three times with cold 10% citric acid followed by three washes with water. The organic phase was removed and dried under sodium sulfate. Succinylated nucleoside was dried under P$_2$O$_5$ overnight in vacuum oven.

EXAMPLE 10

5'-O-DMT-3'-O-methoxyethyl-5-methyl-uridine-2'-O-succinoyl Linked LCA CPG

5'-O-DMT-3'-O-(2-methoxyethyl)-2'-O-succinyl-thymidine was coupled to controlled pore glass (CPG). 1.09 g (1.52 mmol) of the succinate were dried overnight in a vacuum oven along with 4-dimethylaminopyridine (DMAP), 2,2'-dithiobis (5-nitro-pyridine) (dTNP), triphenylphosphine (TPP), and pre-acid washed CPG (controlled pore glass). After about 24 hours, DMAP (1.52 mmol, 186 mg) and acetonitrile (13.7 mL) were added to the succinate. The mixture was stirred under an atmosphere of argon using a magnetic stirrer. In a separate flask, dTNP (1.52 mmol, 472 mg) was dissolved in acetonitrile (9.6 mL) and dichloromethane (4.1 mL) under argon. This reaction mixture was then added to the succinate. In another separate flask, TPP (1.52 mmol, 399 mg) was dissolved in acetonitrile (37 mL) under argon. This mixture was then added to the succinate/DMAP/dTNP reaction mixture. Finally, 12.23 g pre-acid washed LCA CPG (loading=115.2 μmol/g) was added to the main reaction mixture, vortexed shortly and placed on shaker for approximately 3 hours. The mixture was removed from the shaker after 3 hours and the loading was checked. A small sample of CPG was washed with copious amounts of acetonitrile, dichloromethane, and then with ether. The initial loading was found to be 63 µmol/g (3.9 mg of CPG was cleaved with trichloroacetic acid, the absorption of released trityl cation was read at 503 nm on a spectrophotometer to determine the loading.) The whole CPG sample was then washed as described above and dried under $P_2O_5$ overnight in vacuum oven. The following day, the CPG was capped with 25 mL CAP A (tetrahydrofuran/acetic anhydride) and 25 mL CAP B (tetrahydrofuran/pyridine/1-methylimidazole) for approximately 3 hours on shaker. Filtered and washed with dichloromethane and ether. The CPG was dried under $P_2O_5$ overnight in vacuum oven. After drying, 12.25 g of CPG was isolated with a final loading of 90 µmol/g.

EXAMPLE 11

3'-O-Methoxyethyl-5-methyl-N-benzoyl-cytidine-2'-O-succinate

5'-O-DMT-3'-O-(2-methoxy) ethyl-N-benzoyl-cytidine was first succinylated on the 2'-position. Cytidine nucleoside (4 mmol) was reacted with 10.2 mL dichloroethane, 615 mg (6.14 mmol) succinic anhydride, 570 µL (4.09 mmol) triethylamine, and 251 mg (2.05 mmol) 4-dimethylaminopyridine. The reactants were vortexed until dissolved and placed in a heating block at 55° C. for approximately 30 minutes. Completeness of reaction was checked by thin layer chromatography (TLC). The reaction mixture was washed three times with cold 10% citric acid followed by three washes with water. The organic phase was removed and dried under sodium sulfate. The succinylated nucleoside was dried under $P_2O_5$ overnight in vacuum oven.

EXAMPLE 12

5'-O-DMT-3'-O-methoxyethyl-5-methyl-N-benzoyl-cytidine-2'-O-succinoyl Linked LCA CPG 5'-O-DMT-3'-O-(2-methoxyethyl)-2'-O-succinyl-$N^4$-benzoyl cytidine was coupled to controlled pore glass (CPG). 1.05 g (1.30 mmol) of the succinate were dried overnight in a vacuum oven along with 4-dimethylaminopyridine (DMAP), 2,2'-dithiobis (5-nitro-pyridine) (dTNP), triphenylphosphine (TPP), and pre-acid washed CPG (controlled pore glass). The following day, DMAP (1.30 mmol, 159 mg) and acetonitrile (11.7 mL) were added to the succinate. The mixture was "mixed" by a magnetic stirrer under argon. In a separate flask, dTNP (1.30 mmol, 400 mg) was dissolved in acetonitrile (8.2 mL) and dichloromethane (3.5 mL) under argon. This reaction mixture was then added to the succinate. In another separate flask, TPP (1.30 mmol, 338 mg) was dissolved in acetonitrile (11.7 mL) under argon. This mixture was then added to the succinate/DMAP/dTNP reaction mixture. Finally, 10.46 g pre-acid washed LCA CPG (loading=115.2 µmol/g) were added to the main reaction mixture, vortexed shortly and placed on shaker for approximately 2 hours. A portion was removed from shaker after 2 hours and the loading was checked. A small sample of CPG was washed with copious amounts of acetonitrile, dichloromethane, and then with ether. The initial loading was found to be 46 µmol/g. (3.4 mg of CPG were cleaved with trichloroacetic acid). The absorption of released trityl cation was read at 503 nm on a spectrophotometer to determine the loading. The whole CPG sample was then washed as described above and dried under $P_2O_5$ overnight in vacuum oven. The following day, the CPG was capped with 25 mL CAP A (tetrahydrofuran/acetic anhydride) and 25 mL CAP B (tetrahydrofuran/pyridine/1-methyl imidazole) for approximately 3 hours on a shaker. The material was filtered and washed with dichloromethane and ether. The CPG was dried under $P_2O_5$ overnight in vacuum oven. After drying, 10.77 g of CPG was isolated with a final loading of 63 µmol/g.

EXAMPLE 13

5'-O-DMT-3'-O-methoxyethyl-N-6-benzoyl-adenosine-2'-O-succinate

5'-O-DMT-3'-O-(2-methoxyethyl)-$N^6$-benzoyl adenosine was first succinylated on the 2'-position. 3.0 g (4.09 mmol) of the adenosine nucleoside were reacted with 10.2 mL dichloroethane, 615 mg (6.14 mmol) succinic anhydride, 570 µL (4.09 mmol) triethylamine, and 251 mg (2.05 mmol) 4-dimethylaminopyridine. The reactants were vortexed until dissolved and placed in heating block at 55° C. for approximately 30 minutes. Completeness of reaction was checked by thin layer chromatography (TLC). The reaction mixture was washed three times with cold 10% citric acid followed by three washes with water. The organic phase was removed and dried under sodium sulfate. Succinylated nucleoside was dried under $P_2O_5$ overnight in vacuum oven.

EXAMPLE 14

5'-O-DMT-3'-O-(2-methoxyethyl)-N-6-benzoyl-adenosine-2'-O-succinoyl Linked LCA CPG Following succinylation, 5'-O-DMT-3'-O-(2-methoxyethyl)-2'-O-succinyl-$N^6$-benzoyl adenosine was coupled to controlled pore glass (CPG). 3.41 g (4.10 mmol) of the succinate were dried overnight in a vacuum oven along with 4-dimethylaminopyridine (DMAP), 2,2'-dithiobis (5-nitro-pyridine) (dTNP), triphenylphosphine (TPP), and pre-acid washed CPG (controlled pore glass). The following day, DMAP (4.10 mmol, 501 mg) and acetonitrile (37 mL) were added to the succinate. The mixture was "mixed" by a magnetic stirrer under argon. In a separate flask, dTNP (4.10 mmol, 1.27 g) was dissolved in acetonitrile (26 mL) and dichloromethane (11 mL) under argon. This reaction mixture was then added to the succinate. In another separate flask, TPP (4.10 mmol, 1.08 g) was dissolved in acetonitrile (37 mL) under argon. This mixture was then added to the succinate/DMAP/dTNP reaction mixture. Finally, 33 g pre-acid washed LCA CPG (loading=115.2 µmol/g) were added to the main reaction mixture, vortexed shortly and placed on shaker for approximately 20 hours. Removed from shaker after 20 hours and the loading was checked. A small sample of CPG was washed with copious amounts of acetonitrile, dichloromethane, and then with ether. The initial loading was found to be 49 µmol/g. (2.9 mg of CPG were cleaved with trichloroacetic acid). The absorption of released trityl cation was read at 503 nm on a spectrophotometer to determine the loading. The whole CPG sample was then washed as described above and dried under $P_2O_5$ overnight in vacuum oven. The following day, the CPG was capped with 50 mL CAP A (tetrahydrofuran/ acetic anhydride) and 50 mL CAP B (tetrahydrofuran/ pyridine/1-methylimidazole) for approximately 1 hour on the shaker. The material was filtered and washed with dichloromethane and ether. The CPG was dried under $P_2O_5$ overnight in vacuum oven. After drying, 33.00 g of CPG was obtained with a final loading of 66 µmol/g.

EXAMPLE 15

5'-O-DMT-3'-O-(2-methoxyethyl)-N-$^2$-isobutyryl-guanosine-2'-O-succinate

5'-O-DMT-3'-O-(2-methoxyethy)1-$N^2$-isobutyryl guanosine was succinylated on the 2'-sugar position. 3.0 g (4.20 mmol) of the guanosine nucleoside were reacted with 10.5 mL dichloroethane, 631 mg (6.30 mmol) succinic anhydride, 585 1L (4.20 mmol) triethylamine, and 257 mg (2.10 mmol) 4-dimethylaminopyridine. The reactants were vortexed until dissolved and placed in heating block at 55° C. for approximately 30 minutes. Completeness of reaction checked by thin layer chromatography (TLC). The reaction mixture was washed three times with cold 10% citric acid followed by three washes with water. The organic phase was removed and dried under sodium sulfate. The succinylated nucleoside was dried under $P_2O_5$ overnight in vacuum oven.

EXAMPLE 16

5'-O-DMT-3'-O-methoxyethyl-N-2-isobutyryl-guanosine-2'-O-succinoyl Linked LCA CPG Following succinylation, 5'-O-DMT-3'-O-(2-methoxyethyl)-2'-O-succinyl-N-2-benzoyl guanosine was coupled to controlled pore glass (CPG). 3.42 g (4.20 mmol) of the succinate were dried overnight in a vacuum oven along with 4-dimethylaminopyridine (DMAP), 2,2'-dithiobis (5-nitro-pyridine) (dTNP), triphenylphosphine (TPP), and pre-acid washed CPG (controlled pore glass). The following day, DMAP (4.20 mmol, 513 mg) and acetonitrile (37.5 mL) were added to the succinate. The mixture was "mixed" by a magnetic stirrer under argon. In a separate flask, dTNP (4.20 mmol, 1.43 g) was dissolved in acetonitrile (26 mL) and dichloromethane (11 mL) under argon. This reaction mixture was then added to the succinate. In another separate flask, TPP (4.20 mmol, 1.10 g) was dissolved in acetonitrile (37.5 mL) under argon. This mixture was then added to the succinate/DMAP/dTNP reaction mixture. Finally, 33.75 g pre-acid washed LCA CPG (loading= 115.2 µmol/g) were added to the main reaction mixture, vortexed shortly and placed on shaker for approximately 20 hours. Removed from shaker after 20 hours and the loading was checked. A small sample of CPG was washed with copious amounts of acetonitrile, dichloromethane, and then with ether. The initial loading was found to be 64 µmol/g. (3.4 mg of CPG were cleaved with trichloroacetic acid). The absorption of released trityl cation was read at 503 nm on a spectrophotometer to determine the loading. The CPG was then washed as described above and dried under $P_2O_5$ overnight in vacuum oven. The following day, the CPG was capped with 50 mL CAP A (tetrahydrofuran/acetic anhydride) and 50 mL CAP B (tetrahydrofuran/pyridine/1-methylimidazole) for approximately 1 hour on a shaker. The material was filtered and washed with dichloromethane and ether. The CPG was dried under $P_2O_5$ overnight in vacuum oven. After drying, 33.75 g. of CPG was isolated with a final loading of 72 µmol/g.

EXAMPLE 17

5'-O-DMT-3'-O-[hexyl-(6-phthalimido)]-uridine

2',3'-O-Dibutyl stannylene-uridine was synthesized according to the procedure of Wagner et. al., *J. Org. Chem.*, 1974, 39, 24. This compound was dried over $P_2O_5$ under vacuum for 12 hours. To a solution of this compound (29 g, 42.1 mmol) in 200 mL of anhydrous DMF were added (16.8 g, 55 mmol) of 6-bromohexyl phthalimide and 4.5 g of sodium iodide and the mixture was heated at 130° C. for 16 hours under argon. The reaction mixture was evaporated, co-evaporated once with toluene and the gummy tar residue was applied on a silica column (500 g). The column was washed with 2 L of EtOAc followed by eluting with 10% methanol (MeOH):90% EtOAc. The product, 2'- and 3'-isomers of O-hexyl-6-N-phthalimido uridine, eluted as an inseparable mixture ($R_f$=0.64 in 10% MeOH in EtOAc). By $^{13}C$ NMR, the isomeric ration was about 55% of the 2' isomer and about 45% of the 3' isomer. The combined yield was 9.2 g (46.2%). This mixture was dried under vacuum and re-evaporated twice with pyridine. It was dissolved in 150 mL anhydrous pyridine and treated with 7.5 g of DMT-Cl (22.13 mmol) and 500 mg of dimethylaminopyridine (DMAP). After 2 hours, thin layer chromatography (TLC; 6:4 EtOAc:Hexane) indicated complete disappearance of the starting material and a good separation between 2' and 3' isomers ($R_f$=0.29 for the 2' isomer and 0.12 for the 3' isomer). The reaction mixture was quenched by the addition of 5 mL of $CH_3OH$ and evaporated under reduced pressure. The residue was dissolved in 300 mL $CH_2Cl_2$, washed successively with saturated $NaHCO_3$ followed by saturated NaCl solution. It was dried over $Mg_2SO_4$ and evaporated to give 15 g of a brown foam which was purified on a silica gel (500 g) to give 6.5 g of the 2'-isomer and 3.5 g of the 3' isomer.

EXAMPLE 18

5'-O-DMT-3'-O-[hexyl-(6-phthalimido)]-uridine-2'-O-(2-cyanoethyl-N,N,-diisopropyl) Phosphoramidite 5'-DMT-3'-O-[hexyl-(6-phthalimido)]uridine (2 g, 2.6 mmol) was dissolved in 20 mL anhydrous $CH_2Cl_2$. To this solution diisopropylaminotetrazolide (0.2 g, 1.16 mmol) and 2.0 mL 2-cyanoethyl-N,N,N',N'-tetraisopropyl phosphoramidite (6.3 mmol) were added with stirred overnight. TLC (1:1 EtOAc/hexane) showed complete disappearance of starting material. The reaction mixture was transferred with $CH_2Cl_2$ and washed with saturated $NaHCO_3$ (100 mL), followed by saturated NaCl solution. The organic layer was dried over anhydrous $Na_2SO_4$ and evaporated to yield 3.8 g of a crude product, which was purified in a silica column (200 g) using 1:1 hexane/EtOAc to give 1.9 g (1.95 mmol, 74% yield) of the desired phosphoramidite.

EXAMPLE 19

Preparation of 5'-O-DMT-3'-O-[hexyl-(6-phthalimido)]-uridine-2'-O-succinoyl-aminopropyl CPG Succinylated and capped aminopropyl controlled pore glass (CPG; 500 Å pore diameter, aminopropyl CPG, 1.0 grams prepared according to Damha et. al., *Nucl. Acids Res.* 1990, 18, 3813.) was added to 12 mL anhydrous pyridine in a 100 mL round-bottom flask. 1-(3-Dimethylaminopropyl)-3-ethyl-carbodiimide (DEC; 0.38 grams, 2.0 mmol)], triethylamine (TEA; 100 µl, distilled over $CaH_2$), dimethylaminopyridine (DMAP; 0.012 grams, 0.1 mmol) and nucleoside 5'-O-DMT-3'-O-[hexyl-(6-phthalimido)]uridine (0.6 grams, 0.77 mmol) were added under argon and the mixture shaken mechanically for 2 hours. Additional nucleoside (0.20 grams) was added and the mixture shaken for 24 hours. The CPG was filtered off and washed successively with dichloromethane, triethylamine, and dichloromethane. The CPG was then dried under vacuum, suspended in 10 mL piperidine and shaken 15 minutes. The CPG was filtered off, washed thoroughly with dichloromethane and again dried under vacuum. The extent of loading (determined by spectrophotometric assay of DMT cation in 0.3 M p-toluenesulfonic acid at 498 nm) was approximately 28 µmol/g. The 5'-O-(DMT)-3'-O-[hexyl-(6-phthalimido]uridine-2'-O-succinyl-aminopropyl controlled pore glass was used to synthesize the oligomers in an ABI 380B DNA synthesizer using phosphoramidite chemistry standard conditions. A four base oligomer 5'-GACU*-3' was used to confirm the structure of 3'-O-hexylamine tether introduced into the oligonucleotide by NMR. As expected a multiplet signal was observed between 1.0–1.8 ppm in $^1H$ NMR.

EXAMPLE 20
5'-O-DMT-3'-O-[hexylamino]-uridine

5'-O-(DMT)-3'-O-[hexyl-(6-phthalimido)] uridine (4.5 grams, 5.8 mmol) is dissolved in 200 mL methanol in a 500 mL flask. Hydrazine (1 ml, 31 mmol) is added to the stirring reaction mixture. The mixture is heated to 60–65° C. in an oil bath and refluxed 14 hours. The solvent is evaporated in vacuo and the residue is dissolved in dichloromethane (250 mL) and extracted twice with an equal volume $NH_4OH$. The organic layer is evaporated to yield the crude product which NMR indicates is not completely pure. $R_f$=0 in 100% ethyl acetate. The product is used in subsequent reactions without further purification.

EXAMPLE 21
3'-O-[Propyl-(3-phthalimido)]-adenosine

To a solution of adenosine (20.0 g, 75 mmol) in dry dimethylformamide (550 ml) at 5° C. was added sodium hydride (60% oil, 4.5 g, 112 mmol). After one hour, N-(3-bromopropyl)phthalimide (23.6 g, 86 mmol) was added and the temperature was raised to 30° C. and held for 16 hours. Ice is added and the solution evaporated in vacuo to a gum. The gum was partitioned between water and ethyl acetate (4×300 mL). The organic phase was separated, dried, and evaporated in vacuo and the resultant gum chromatographed on silica gel (95/5 $CH_2Cl_2$/MeOH) to give a white solid (5.7 g) of the 2'-O-(propylphthalimide)adenosine. Thee fractions containing the 3'-O-(propylphthalimide)adenosine were chromatographed a second time on silica gel using the same solvent system.

Crystallization of the 2'-O-(propylphthalimide)adenosine fractions from methanol gave a crystalline solid, m.p. 123–124C. $^1$H NMR (400 MHZ: DMSO-$d_6$) δ 1.70 (m, 2H, $CH_2$), 3.4–3.7 (m, 6H, C5., $CH_2$, $OCH_2$, Phth $CH_2$), 3.95 (q, 1H, $C_4.H$), 4.30 (q, 1H, $C_5.H$), 4.46 (t, 1H, $C_2.H$), 5.15 (d, 1H, $C_3.OH$), 5.41 (t, 1H, C5.0H), 5.95 (d, 1H, $C_1.H$) 7.35 (s, 2H, $NH_2$), 7.8 (brs, 4H, Ar), 8.08 (s, 1H, $C_2H$) and 8.37 (s, 1H, $C_8H$). Anal. Calcd. $C_{21}H_{22}N_6O_6$: C, 55.03; H, 4.88; N, 18.49. Found: C, 55.38; H, 4.85; N, 18.46.

Crystallization of the 3'-O-(propylphthalimide)adenosine fractions from $H_2O$ afforded an analytical sample, m.p. 178–179C. $^1$H NMR (400 MHZ: DMSO-$d_6$) δ 5.86 (d, 1H, H-1').

EXAMPLE 22
3'-O-[Propyl-(3-phthalimido)]-N-6-benzoyl-adenosine

3'-O-(3-propylphthalimide)adenosine is treated with benzoyl chloride in a manner similar to the procedure of Gaffney, et al., *Tetrahedron Lett.* 1982, 23, 2257. Purification of crude material by chromatography on silica gel (ethyl acetate-methanol) gives the title compound.

EXAMPLE 23
3'-O-[Propyl-(3-phthalimido)]-5'-O-DMT-N-6-benzoyl-adenosine

To a solution of 3'-O-(propyl-3-phthalimide)-$N^6$-benzoyladenosine (4.0 g) in pyridine (250 ml) is added DMT-Cl (3.3 g). The reaction is stirred for 16 hours. The reaction is added to ice/water/ethyl acetate, the organic layer separated, dried, and concentrated in vacuo and the resultant gum chromatographed on silica gel (ethyl acetate-methanol triethylamine) to give the title compound.

EXAMPLE 24
3'-O-[Propyl-(3-phthalimido)]-5'-O-DMT-N-6-Benzoyl-adenosine-2'-O-(2-cyanoethyl-N,N-diisopropyl) Phosphoramidite 3'-O-(Propyl-3-phthalimide)-5'-O-DMT-$N^6$-benzoyladenosine is treated with (β-cyanoethoxy)chloro-N,N-diisopropyl)aminophosphane in a manner similar to the procedure of Seela, et al., *Biochemistry* 1987,26, 2233. Chromatography on silica gel (EtOAc/hexane) gives the title compound as a white foam.

EXAMPLE 25
3'-O-(Aminopropyl)-adenosine

A solution of 3'-O-(propyl-3-phthalimide)adenosine (8.8 g, 19 mmol), 95% ethanol (400 mL) and hydrazine (10 mL, 32 mmol) is stirred for 16 hrs at room temperature. The reaction mixture is filtered and filtrate concentrated in vacuo. Water (150 mL) is added and acidified with acetic acid to pH 5.0. The aqueous solution is extracted with EtOAc (2×30 mL) and the aqueous phase is concentrated in vacuo to afford the title compound as a HOAc salt.

EXAMPLE 26
3'-O-[3-(N-trifluoroacetamido)propyl]-adenosine

A solution of 3'-O-(propylamino)adenosine in methanol (50 mL) and triethylamine (15 mL, 108 mmol) is treated with ethyl trifluoroacetate (18 mL, 151 mmol). The reaction is stirred for 16 hrs and then concentrated in vacuo and the resultant gum chromatographed on silica gel (9/1, EtOAc/MeOH) to give the title compound.

EXAMPLE 27
N6-Dibenzoyl-3'-O-[3-(N-trifluoroacetamido)propyl]-adenosine

3'-O-[3-(N-trifluoroacetamido)propyl]adenosine is treated as per Example 22 using a Jones modification wherein tetrabutylammonium fluoride is utilized in place of ammonia hydroxide in the work up. The crude product is purified using silica gel chromatography (EtOAc/MeOH 1/1) to give the title compound.

EXAMPLE 28
N6-Dibenzoyl-5'-O-DMT-3'-O-[3-(N-trifluoroacetamido)propyl]-adenosine DMT-Cl (3.6 g, 10.0 mmol) is added to a solution of $N^6$-(dibenzoyl)-3'-O-[3-(N-trifluoroacetamido)propyl]adenosine in pyridine (100 mL) at room temperature and stirred for 16 hrs. The solution is concentrated in vacuo and chromatographed on silica gel (EtOAc/TEA 99/1) to give the title compound.

EXAMPLE 29
N6-Dibenzoyl-5'-O-DMT-3'-O-[3-(N-trifluoroacetamido)propyl]-adenosine-2'-O-(2-cyanoethyl-N,N-diisopropyl)phosphoramidite A solution of $N^6$-(dibenzoyl)-5'-O-(DMT)-3'-O-[3-(N-trifluoroacetamido)propyl]-adenosine in dry $CH_2Cl_2$ is treated with bis-N,N-diisopropylamino cyanoethyl phosphite (1.1 eqiv) and N,N-diisopropylaminotetrazolide (catalytic amount) at room temperature for 16 hrs. The reaction is concentrated in vacuo and chromatographed on silica gel (EtOAc/hexane/TEA 6/4/1) to give the title compound.

EXAMPLE 30
3'-O-(butylphthalimido)-adenosine

The title compound is prepared as per Example 21, using N-(4-bromobutyl)phthalimide in place of the 1-bromopropane. Chromatography on silica gel (EtOAC-MeOH) gives the title compound. $^1$H NMR (200 MHZ, DMSO-d$_6$) δ 5.88 (d, 1H, C$_1$.H).

EXAMPLE 31
N6-Benzoyl-3'-O-(butylphthalimido)-adenosine

Benzoylation of 3'-O-(butylphthalimide)adenosine as per Example 22 gives the title compound.

EXAMPLE 32
N6-Benzoyl-5'-O-DMT-3'-O-(butylphthalimido)-adenosine

The title compound is prepared from 3'-O-(butylphthalimide)-N$^6$-benzoyladenosine as per Example 22.

EXAMPLE 33
N6-Benzoyl-5'-O-DMT-3'-O-(butylphthalimido)-Adenosine-2'-O-(2-cyanoethyl-N,N-diisopropyl) phosphoramidite The title compound is prepared from 3'-O-(butylphthalimide)-5'-O-DMT-N$^6$-benzoyladenosine as per Example 24.

EXAMPLE 34
3'-O-(Pentylphthalimido)-adenosine

The title compound is prepared as per Example 21, using N-(5-bromopentyl)phthalimide. The crude material from the extraction is chromatographed on silica gel using CHCl$_3$/MeOH (95/5) to give a mixture of the 2' and 3' isomers. The 2' isomer is recrystallized from EtOH/MeOH 8/2. The mother liquor is rechromatographed on silica gel to afford the 3' isomer.

2'-O-(Pentylphthalimido)adenosine: M.P. 159–160° C. Anal. Calcd. for C$_{23}$H$_{24}$N$_6$O$_5$: C, 57.26; H, 5.43; N, 17.42. Found: C, 57.03; H, 5.46; N, 17.33. 3'-O-(Pentylphthalimido)-adenosine: $^1$H NMR (DMSO-d$_6$) δ 5.87 (d, 1H, H-1').

EXAMPLE 35
N6-Benzoyl-3'-O-(pentylphthalimido)-adenosine

Benzoylation of 3'-O-(pentylphthalimido)adenosine is achieved as per the procedure of Example 22 to give the title compound.

EXAMPLE 36
N6-Benzoyl-5'-O-DMT-3'-O-(pentylphthalimido)-adenosine

The title compound is prepared from 3'-O-(pentylphthalimide)-N$^6$-benzoyladenosine as per the procedure of Example 23. Chromatography on silica gel (ethylacetate, hexane, triethylamine), gives the title compound.

EXAMPLE 37
N6-Benzoyl-5'-O-DMT-3'-O-(pentylphthalimido)-adenosine-2'-O-(2-cyanoethyl-N,N-diisopropyl) Phosphoramidite The title compound is prepared from 3'-O-(pentylphthalimide)-5'-O-(DMT)—N$^6$-benzoyladenosine as per the procedure of Example 24 to give the title compound.

EXAMPLE 38
3'-O-(Propylphthalimido)uridine

A solution of uridine-tin complex(48.2 g, 115 mmol)in dry DMF (150 ml) and N-(3-bromopropyl)phthalimide (46 g, 172 mmol) was heated at 130° C. for 6 hrs. The crude product was chromatographed directly on silica gel CHCl$_3$/MeOH 95/5. The isomer ratio of the purified mixture was 2'/3' 81/19. The 2' isomer was recovered by crystallization from MeOH. The filtrate was rechromatographed on silica gel using CHCl$_3$CHCl$_3$/MeOH (95/5) gave the 3' isomer as a foam.

2'-O-(Propylphthalimide)uridine: Analytical sample recrystallized from MeOH, m.p. 165.5–166.5C, $^1$H NMR (200 MHZ, DMSO-d$_6$) δ 1.87 (m, 2H, CH$_2$), 3.49–3.65 (m, 4H, C$_2$,H), 3.80–3.90 (m, 2H, C$_3$.H$_1$C$_4$.H), 4.09 (m, 1H, C$_2$.H), 5.07 (d, 1 h, C$_3$.OH), 5.16 (m, 1H, C$_5$.OH), 5.64 (d, 1H, CH=), 7.84 (d, 1H, C$_1$.H), 7.92 (bs, 4H, Ar), 7.95 (d, 1H, CH=) and 11.33 (s, 1H, ArNH). Anal. C$_{20}$H$_{21}$N$_3$H$_8$, Calcd. C, 55.69; H, 4.91;, N, 9.74. Found, C, 55.75; H, 5.12; N, 10.01. 3'-O-(Propylphthalimide)uridine: $^1$H NMR (DMSO-d$_6$) δ 5.74 (d, 1H, H-1').

EXAMPLE 39
3'-O-(Aminopropyl)-uridine

The title compound is prepared as per the procedure of Example 25.

EXAMPLE 40
3'-O-[3-(N-trifluoroacetamido)propyl]-uridine

3'-O-(Propylamino)uridine is treated as per the procedure of Example 26 to give the title compound.

EXAMPLE 41
5'-O-DMT-3'-O-[3-(N-trifluoroacetamido)propyl]-uridine

3'-O-[3-(N-trifluoroacetamido)propyl]uridine is treated as per the procedure of Example 28 to give the title compound.

EXAMPLE 42
5'-O-DMT-3'-O-[3-(N-trifluoroacetamido)propyl]-uridine-2'-O-(2-cyanoethyl-N,N-diisopropyl) Phosphoramidite 5'-O-(DMT)-3'-O-[3-(N-trifluoroacetamido)propyl]uridine is treated as per the procedure of Example 29 to give the title compound.

EXAMPLE 43
3'-O-(Propylphthalimido)-cytidine

The title compounds were prepared as per the procedure of Example 21. 2'-O-(propylphthalimide)cytidine: $^1$H NMR (200 MHZ, DMSO-d$_6$) δ 5.82 (d, 1H, C$_1$.H).

3'-O-(propylphthalimide)cytidine: $^1$H NMR (200 MHZ, DMSO-d$_6$) δ 5.72 (d, 1H, C$_1$.H).

EXAMPLE 44
3'-O-(Aminopropyl)-cytidine

3'-O-(Propylphthalimide)cytidine is treated as per the procedure of Example 25 to give the title compound.

EXAMPLE 45
3'-O-[3-(N-trifluoroacetamido)propyl]-cytidine

3'-O-(Propylamino)cytidine is treated as per the procedure of Example 26 to give the title compound.

EXAMPLE 46
N4-Benzoyl-3'-O-[3-(N-trifluoroacetamido)propyl]-cytidine

3'-O-[3-(N-trifluoroacetamido)propyl]cytidine is treated as per the procedure of Example 27 to give the title compound.

EXAMPLE 47

N4-Benzoyl-5'-O-DMT-3'-O-[3-(N-trifluoroacetamido) propyl]-cytidine $N^4$-(Benzoyl)-3'-O-[3-(N-trifluoroacetamido)propyl] cytidine is treated as per the procedure of Example 28 to give the title compound.

minute coupling step). All novel amidites were also coupled four times per cycle but the coupling time was increased to approximately 20 minutes (delivering 480 μL of amidite). Oxidation times remained the same but the delivery of oxidizing agent increased to approximately 1.88 mL per cycle. Oligonucleotides were cleaved and deprotected in 5 mL 28.0–30% NH$_4$OH at 55° C., for approximately 16 hours.

TABLE I

3'-O-(2-methoxyethyl) containing 2'-5' linked oligonucleotides.

| SEQ ID NO. # | (ISIS)# | Sequence (5'-3')[1] | Backbone | Chemistry |
|---|---|---|---|---|
| 4 | (17176) | ATG-CAT-TCT-GCC-CCC-AAG-GA* | P=S | 3'-O-MOE |
| 5 | (17177) | ATG-CAT-TCT-GCC-CCC-AAG-G*A* | P=S | 3'-O-MOE |
| 6 | (17178) | ATG-CAT-TCT-GCC-CCC-AAG$_O$-G*$_O$A* | P=S/P=O | 3'-O-MOE |
| 7 | (17179) | A*TG-CAT-TCT-GCC-CCC-AAG-GA* | P=S | 3'-O-MOE |
| 8 | (17180) | A*TG-CAT-TCT-GCC-CCC-AAG-G*A* | P=S | 3'-O-MOE |
| 9 | (17181) | A*$_O$TG-CAT-TCT-GCC-AAA-AAG$_O$-G*$_O$A* | P=S/P=O | 3'-O-MOE |
| 10 | (21415) | A*T*G-CAT-TCT-GCC-AAA-AAG-G*A* | P=S | 3'-O-MOE |
| 11 | (21416) | A*$_O$T*$_O$G-CAT-TCT-GCC-AAA-AAG$_O$-G*$_O$A* | P=S/P=O | 3'-O-MOE |
|  | (21945) | A*A*A* | P=O | 3'-O-MOE |
|  | (21663) | A*A*A*A* | P=O | 3'-O-MOE |
|  | (20389) | A*U*C*G* | P=O | 3'-O-MOE |
| 12 | (20390) | C*G*C*-G*A*A*-T*T*C*-G*C*G* | P=O | 3'-O-MOE |

[1]All nucleosides with an asterisk contain 3'-O-(2-methoxyethyl).

EXAMPLE 48

N4-Benzoyl-5'-O-DMT-3'-O-[3-(N-trifluoroacetamido) propyl]-cytidine-2'-O-(2-cyanoethyl-N,N-diisopropyl) phosphoramidite $N^4$-(Benzoyl)-5'-O-(DMT)-3'-O-[3-(N-trifluoroacetamido)propyl]cytidine is treated as per the procedure of Example 29 to give the title compound.

EXAMPLE 49

General Procedures for Oligonucleotide Synthesis

Oligonucleotides were synthesized on a Perseptive Biosystems Expedite 8901 Nucleic Acid Synthesis System. Multiple 1-μmol syntheses were performed for each oligonucleotide. Trityl groups were removed with trichloroacetic acid (975 μL over one minute) followed by an acetonitrile wash. All standard amidites (0.1M) were coupled twice per cycle (total coupling time was approximately 4 minutes). All novel amidites were dissolved in dry acetonitrile (100 mg of amidite/1 mL acetonitrile) to give approximately 0.08–0.1 M solutions. Total coupling time was approximately 6 minutes (105 μL of amidite delivered). 1-H-tetrazole in acetonitrile was used as the activating agent. Excess amidite was washed away with acetonitrile. (1S)-(+)-(10-camphorsulfonyl) oxaziridine (CSO, 1.0 g CSO/8.72 mL dry acetonitrile) was used to oxidize (4 minute wait step) phosphodiester linkages while 3H-1,2-benzodithiole-3-one-1,1-dioxide (Beaucage reagent, 3.4 g Beaucage reagent/200 mL acetonitrile) was used to oxidize (one minute wait step) phosphorothioate linkages. Unreacted functionalities were capped with a 50:50 mixture of tetrahyrdofuran/acetic anhydride and tetrahydrofuran/pyridine/1-methylimidazole. Trityl yields were followed by the trityl monitor during the duration of the synthesis. The final DMT group was left intact. The oligonucleotides were deprotected in 1 mL 28.0–30% ammonium hydroxide (NH$_4$OH) for approximately 16 hours at 55° C. Oligonucleotides were also made on a larger scale (20 μmol/synthesis). Trityl groups were removed with just over 8 mL of trichloroacetic acid. All standard amidites (0.1M) were coupled twice per cycle (13

EXAMPLE 50

General Procedure for Purification of Oligonucleotides

Following cleavage and deprotection step, the crude oligonucleotides (such as those synthesized in Example 49) were filtered from CPG using Gelman 0.45 μm nylon acrodisc syringe filters. Excess NH$_4$OH was evaporated away in a Savant AS 160 automatic speed vac. The crude yield was measured on a Hewlett Packard 8452A Diode Array Spectrophotometer at 260 nm. Crude samples were then analyzed by mass spectrometry (MS) on a Hewlett Packard electrospray mass spectrometer and by capillary gel electrophoresis (CGE) on a Beckmann P/ACE system 5000. Trityl-on oligonucleotides were purified by reverse phase preparative high performance liquid chromatography (HPLC). HPLC conditions were as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/min flow rate; Gradient: 5% B for first five minutes with linear increase in B to 60% during the next 55 minutes. Larger oligo yields from the larger 20 μmol syntheses were purified on larger HPLC columns (Waters Bondapak HC 18HA) and the flow rate was increased to 5.0 mL/min. Appropriate fractions were collected and solvent was dried down in speed vac. Oligonucleotides were detritylated in 80% acetic acid for approximately 45 minutes and lyophilized again. Free trityl and excess salt were removed by passing detritylated oligonucleotides through Sephadex G-25 (size exclusion chromatography) and collecting appropriate samples through a Pharmacia fraction collector. Solvent again evaporated away in speed vac. Purified oligonucleotides were then analyzed for purity by CGE, HPLC (flow rate: 1.5 mL/min; Waters Delta Pak C4 column, 3.9×x300 mm), and MS. The final yield was determined by spectrophotometer at 260 nm.

TABLE II

Physical characteristics of 3'-O-(2-methoxyethyl) containing 2'-5' linked oligonucleotides.

|       | Expected Mass | Observed Mass | HPLC[2] T$_R$ Purified (min.) | #Ods (260 nm) |
|-------|---------------|---------------|-------------------------------|---------------|
| 17176 | 6440.743      | 6440.300      | 23.47                         | 3006          |
| 17177 | 6514.814      | 6513.910      | 23.67                         | 3330          |
| 17178 | 6482.814      | 6480.900      | 23.06                         | 390           |
| 17179 | 6513.798      | 6513.560      | 23.20                         | 3240          |
| 17180 | 6588.879      | 6588.200      | 23.96                         | 3222          |
| 17181 | 6540.879      | 6539.930      | 23.01                         |               |
| 21415 | 6662.976      | 6662.700      | 24.18                         | 4008          |

TABLE II-continued

Physical characteristics of 3'-O-(2-methoxyethyl) containing 2'-5' linked oligonucleotides.

|       | Expected Mass | Observed Mass | HPLC[2] T$_R$ Purified (min.) | #Ods (260 nm) |
|-------|---------------|---------------|-------------------------------|---------------|
| 21416 | 6598.969      | 6597.800      | 23.01                         | 3060          |
| 21945 | 1099.924      | 1099.300      | 19.92                         | 121           |
| 21663 | 1487.324      | 1486.800      | 20.16                         | 71            |
| 20389 | 1483.000      | 1482.000      |                               | 62            |
| 20390 | 4588.000      | 4591.000      |                               | 151           |

[2]Conditions: Waters 600E with detector 991; Waters C4 column (3.9 × 300 mm); Solvent A: 50 mM TEA-Ac, pH 7.0; B: 100% acetonitrile; 1.5 mL/min. flow rate; Gradient: 5% B for first five minutes with linear increase in B to 60% during the next 55 minutes.

EXAMPLE 51
$T_m$ Studies on Modified Oligonucleotides

Oligonucleotides synthesized in Examples 49 and 50 were evaluated for their relative ability to bind to their complementary nucleic acids by measurement of their melting temperature ($T_m$). The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Selected test oligonucleotides and their complementary nucleic acids were incubated at a standard concentration of 4 μM for each oligonucleotide in buffer (100 mM NaCl, 10 mM sodium phosphate, pH 7.0, 0.1 mM EDTA). Samples were heated to 90° C. and the initial absorbance taken using a Guilford Response II Spectrophotometer (Corning). Samples were then slowly cooled to 15° C. and then the change in absorbance at 260 nm was monitored with heating during the heat denaturation procedure. The temperature was increased by 1 degree ° C./absorbance reading and the denaturation profile analyzed by taking the 1$^{st}$ derivative of the melting curve. Data was also analyzed using a two-state linear regression analysis to determine the Tm=s. The results of these tests for the some of the oligonucleotides from Examples 49 and 50 are shown in Table III below.

TABLE III

Tm Analysis of Oligonucleotides

| SEQ ID NO. # | (ISIS)# | Sequence (5'-3') | Backbone | T$_m$8 | # Mods Linkages | #2'-5' |
|---|---|---|---|---|---|---|
| 13 | (11061) | ATG-CAT-TCT-GCC-CCC-AAG-GA | P=S | 61.4 |  | 0 |
| 4 | (17176) | ATG-CAT-TCT-GCC-CCC-AAG-GA* | P=S | 61.4 | 1 | 0 |
| 5 | (17177) | ATG-CAT-TCT-GCC-CCC-AAG-G*A* | P=S | 61.3 | 2 | 1 |
| 6 | (17178) | ATG-CAT-TCT-GCC-CCC-AAG$_O$-G*$_O$A* | P=S/P=O | 61.8 | 2 | 1 |
| 7 | (17179) | A*TG-CAT-TCT-GCC-CCC-AAG-GA* | P=S | 61.1 | 2 | 1 |
| 8 | (17180) | A*TG-CAT-TCT-GCC-CCC-AAG-G*A* | P=S | 61.0 | 3 | 2 |
| 9 | (17181) | A*$_O$TG-CAT-TCT-GCC-AAA-AAG$_O$-G*$_O$A* | P=S/P=O | 61.8 | 3 | 2 |
| 10 | (21415) | A*T*G-CAT-TCT-GCC-AAA-AAG-G*A* | P=S | 61 | 4 | 3 |
| 11 | (21416) | A*$_O$T*$_O$G-CAT-TCT-GCC-AAA-AAG$_O$-G*$_O$A* | P=S/P=O | 61.7 | 4 | 3 |

EXAMPLE 52
NMR Experiments on Modified Oligonucleotides Comparison of 3',5' Versus 2',5' Internucleotide Linkages and 2'-substituents Versus 3'-Substituents by NMR The 400 MHz $^1$H spectrum of oligomer d(GAU$_2$*CT), where U$_2$*=2'-O-aminohexyluridine showed 8 signals between 7.5 and 9.0 ppm corresponding to the 8 aromatic protons. In addition, the anomeric proton of U* appears as a doublet at 5.9 ppm with J$_{1',2'}$=7.5 Hz, indicative of C2'-endo sugar puckering. The corresponding 2'–5' linked isomer shows a similar structure with J$_{1',2'}$=3.85 Hz at 5.75 ppm, indicating an RNA type sugar puckering at the novel modification site favorable for hybridization to an mRNA target. The proton spectrum of the oligomer d(GACU$_3$*), where U$_3$*=3'-O-hexylamine, showed the expected 7 aromatic proton signals between 7.5 and 9.0 ppm and the anomeric proton doublet at 5.9 ppm with J$_{1',2'}$=4.4 Hz. This suggests more of a C3'-endo puckering for the 3'-O-alkylamino compounds compared to their 2' analogs. $^{31}$P NMR of these oligonucleotides showed the expected 4 and 3 signals from the internucleotide phosphate linkages for d(GAU*CT) and d(GACU*), respectively. 3'–5' Linked vs. 2'–5' linked have different retention times in RP HPLC and hence different lipophilicities, implying potentially different extent of interactions with cell membranes.

EXAMPLE 53
Analysis of 2',5'-Linked Oligonucleotides Versus 3',5'-Linked Oligonucleotides Thermal melts were done as per standarized literature procedures. Oligonucleotide identity is as follows:

Oligonucleotide A is a normal 3'–5' linked phosphodiester oligodeoxyribonucleotide of the sequence d(GGC TGU* CTG CG) SEQ ID NO: 14 where the * indicates the attachment site of a 2'-aminolinker. Oligonucleotide B is a normal 3'–5' linked phosphodiester oligoribonucleotide of the sequence d(GGC TGU* CTG CG) SEQ ID NO: 14 where the * indicates the attachment site of a 2'-aminolinker. Each of the ribonucleotides of the oligonucleotide, except the one bearing the * substituent, are 2'-O-methyl ribonucleotides. Oligonucleotide C has 2'–5' linkage at the * position in addition to a 3'-aminolinker at this site. The remainder of the oligonucleotide is a phosphodiester oligodeoxyribonucleotide of the sequence d(GGC TGU* CTG CG) SEQ ID NO: 14. The base oligonucleotide (no 2'-aminolinker) was not included in the study.

TABLE IIIa

| OLIGONUCLEOTIDE | MODIFICATION | DNA TARGET | RNA TARGET |
|---|---|---|---|
| A | none | 52.2 | 54.1 |
|   | 2'-aminolinker | 50.9 | 55.5 |
| B | none | 51.5 | 72.3 |
|   | 2'-aminolinker | 49.8 | 69.3 |
| C | none | NA |   |
|   | 3'-aminolinker | 42.7 | 51.7 |

The 2'–5' linkages demonstrated a higher melting temperature against an RNA target compared to a DNA target.

EXAMPLE 54
Snake Venom Phosphodiesterase and Liver Homogenate Experiments on Oligonucleotide Stability The following oligonucleotides were synthesized following the procedure of Example 49.

EXAMPLE 55
3'-O-Aminopropyl Modified Oligonucleotides

Following the procedures illustrated above for the synthesis of oligonucleotides, modified 3'-amidites were used in addition to conventional amidites to prepare the oligonucleotides listed in tables VI and VII. Nucleosides used include: N6-benzoyl-3'-O-propylphthalimido-A-2'-amidite, 2'-O-propylphthaloyl-A-3'-amidite, 2'-O-methoxyethyl-thymidine-3'-amidite (RIC, Inc.), 2'-O-MOE-G-3'-amidite (RI Chemical), 2'-O-methoxyethyl-5-methylcytidine-3'-amidite, 2'-O-methoxyethyl-adenosine-3'-amidite (RI Chemical), and 5-methylcytidine-3'-amidite. 3'-propylphthalimido-A and 2'-propylphthalimido-A were used as the LCA—CPG solid support. The required amounts of the amidites were placed in dried vials, dissolved in acetonitrile (unmodified nucleosides were made into 1M solutions and modified nucleosides were 100 mg/mL), and connected to the appropriate ports on a Millipore Expedite™ Nucleic Acid Synthesis System. Solid support resin (60 mg) was used in each column for 2×1 μmole scale synthesis (2 columns for each oligo were used). The synthesis was run using the IBP-PS(1 μmole) coupling protocol for phosphorothioate backbones and CSO-8 for phosphodiesters. The trityl reports indicated normal coupling results.

After synthesis the oligonucleotides were deprotected with conc. ammonium hydroxide(aq) containing 10% of a solution of 40% methylamine (aq) at 55° C. for approximately 16 hrs. Then they were evaporated, using a Savant AS160 Automatic SpeedVac, (to remove ammonia) and filtered to remove the CPG-resin. The crude samples were analyzed by MS, HPLC, and CE. Then they were purified on a Waters 600E HPLC system with a 991 detector using a Waters C4 Prep. scale column (Alice C4 Prep.) and the

TABLE IV

Modified Oligonucleotides synthesized to evaluate stability

| SEQ ID NO. # | (ISIS)# | Sequence (5'-3') | Backbone | Chemistry |
|---|---|---|---|---|
| 15 | (22110) | TTT-TTT-TTT-TTT-TTT-T*T*T*-T* | P=O | 3'-O-MOE |
| 16 | (22111) | TTT-TTT-TTT-TTT-TTT-T#T#T#-U# | P=O | 3'-O-MOE |
| 15 | (22112) | TTT-TTT-TTT-TTT-TTT-T*T*T*-T* | P=S | 3'-O-MOE |
| 16 | (22113) | TTT-TTT-TTT-TTT-TTT-T#T#T#-U# | P=S | 3'-O-MOE |
| 15 | (22114) | TTT-TTT-TTT-TTT-TTT$_o$-T*$_o$T*$_o$T*$_o$T* | P=S/P=O | 3'-O-MOE |
| 16 | (22115) | TTT-TTT-TTT-TTT-TTT$_o$-T#$_o$T#$_o$T#$_o$-U# | P=S/P=O | 3'-O-MOE |

¹All nucleosides with an asterisk contain 3'-O-(2-methoxyethyl). All nucleosides with a # contain 2'-O-(2-methoxyethyl).

The oligonucleotides were purified following the procedure of Example 50 and analyzed for their structure.

TABLE V

Properties of Modified Oligonucleotides

| SEQ ID NO. # | (ISIS)# | #Sequence (5'-3')¹ | Expected Mass | Observed Mass | HPLC² T$_R$ Purified (min.) | #Ods (260nm) |
|---|---|---|---|---|---|---|
| 15 | (22110) | TTT-TTT-TTT-TTT-TTT-T*T*T*-T* | 6314.189 | 6315.880 | 20.39 | 174 |
| 16 | (22111) | TTT-TTT-TTT-TTT-TTT-T#T#T#-U# | 6004.777 | 5997.490 | 20.89 | 147 |
| 15 | (22112) | TTT-TTT-TTT-TTT-TTT-T*T*T*-T* | 6298.799 | 6301.730 | 25.92 | 224 |
| 16 | (22113) | TTT-TTT-TTT-TTT-TTT-T#T#T#-U# | 6288.745 | 6286.940 | 24.77 | 209 |
| 15 | (22114) | TTT-TTT-TTT-TTT-TTT$_o$-T*$_o$T*$_o$T*$_o$-T* | 6234.799 | 6237.150 | 24.84 | 196 |
| 16 | (22115) | TTT-TTT-TTT-TTT-TTT$_o$-T#$_o$T#$_o$T#$_o$-U# | 6224.745 | 6223.780 | 23.30 | 340 |

¹All nucleosides with an asterisk contain 3'-O-(2-methoxyethyl). All nucleosides with a # contain 2'-O-(2-methoxy)ethyl.
²Conditions: Waters 600E with detector 991; Waters C4 column (3.9 × 300 mm); Solvent A: 50 mM TEA-Ac, pH 7.0; B: 100% acetonitrile; 1.5 mL/min. flow rate; Gradient: 5% B for first five minutes with linear increase in B to 60% during the next 55 minutes.

following solvents: A: 50 mM TEA-Ac, pH 7.0 and B: acetonitrile utilizing the AMPREP2@ method. After purification the oligonucleotides were evaporated to dryness and then detritylated with 80% acetic acid at room temp. for approximately 30 min. Then they were evaporated.

The oligonucleotides were dissolved in conc. ammonium hydroxide and run through a column containing Sephadex G-25 using water as the solvent and a Pharmacia LKB SuperFrac fraction collector. The resulting purified oligonucleotides were evaporated and analyzed by MS, CE, and HPLC.

The CGE analysis inidcated the relative nuclease resistance of 2',5'-linked oligomers compared to ISIS 11061 (Table III, Example 51) (uniformly 2'-deoxyphosphorothioate oligonucleotide targeted to mouse c-raf). Because of the nuclease resistance of the 2',5'-linkage, coupled with the fact that 3'-methoxyethoxy substituents are present and afford further nuclease protection the oligonucleotides ISIS 17176, ISIS 17177, ISIS 17178, ISIS 17180, ISIS 17181 and ISIS 21415 were found to be more stable in plasma, while ISIS 11061 (Table III) was not. Similar observations were noted in kidney and liver tissue.

TABLE VI

Oligonucleotides bearing Aminopropyl Substituents

| SEQ ID NO. # | (ISIS)# | Sequence (5'-3')[1] | Backbone |
|---|---|---|---|
| 19 | (23185-1) | A*TG-CAT-TCT-GCC-CCC-AAG-GA* | P=S |
| 19 | (23186-1) | A*TG-CAT-TCT-GCC-CCC-AAG-GA* | P=S |
| 20 | (23187-1) | A*$_o$T$_o$G$_o$-C$_o$A$_o$T$_s$-T$_s$C$_s$T$_s$-G$_s$C$_s$C$_s$-C$_s$C$_s$C$_s$-A$_o$A$_o$G$_o$-G$_o$A* | P=S/P=O |
| 20 | (23980-1) | A*$_o$T$_o$G$_o$-C$_o$A$_s$T$_s$-T$_s$C$_s$T$_s$-G$_s$C$_s$C$_s$-C$_s$C$_s$C$_s$-A$_o$A$_o$G$_o$-G$_o$A* | P=S/P=O |
| 19 | (23981-1) | A*-TG-CAT-TCT-GCC-CCC-AAG-GA* | P=S |
| 19 | (23982-1) | A*TG-CAT-TCT-GCC-CCC-AAG-GA* | P=S |

[1]All underlined nucleosides bear a 2'-O-methoxyethyl substituent; internucleotide linkages in PS/PO oligonucleotides are indicated by subscript >s= and >o= notations respectively; A* = 3'-aminopropyl-A; A* = 2'-aminopropyl-A; C = 5-methyl-C

TABLE VII

Aminopropyl Modified Oligonucleotides

| ISIS # | Expected Mass (g/mol) | Observed Mass (g/mol) | HPLC Retention Time (min) | CE Retention Time (min) | Crude Yield (Ods) | Final Yield (Ods) |
|---|---|---|---|---|---|---|
| 23185-1 | 6612.065 | 6610.5 | 23.19 | 5.98 | 948 | 478 |
| 23186-1 | 7204.697 | 7203.1 | 24.99 | 6.18 | 1075 | 379 |
| 23187-1 | 7076.697 | 7072.33 | 23.36 | 7.56 | 838 | 546 |
| 23980-1 | 7076.697 | 7102.31 | 23.42 | 7.16 | 984 | 373 |
| 23981-1 | 7204.697 | 7230.14 | 25.36 | 7.18 | 1170 | 526 |
| 23982-1 | 6612.065 | 6635.71 | 23.47 | 7.31 | 1083 | 463 |

EXAMPLE 56
In Vivo Stability of Modified Oligonucleotides

The in vivo stability of selected modified oligonucleotides synthesized in Examples 49 and 55 was determined in BALB/c mice. Following a single i.v. administration of 5 mg/kg of oligonucleotide, blood samples were drawn at various time intervals and analyzed by CGE. For each oligonucleotide tested, 9 male BALB/c mice (Charles River, Wilmington, Mass.) weighing about 25 g were used. Following a one week acclimatization the mice received a single tail-vein injection of oligonucleotide (5 mg/kg) administered in phosphate buffered saline (PBS), pH 7.0. One retro-orbital bleed (either at 0.25, 0.5, 2 or 4 h post-dose) and a terminal bleed (either 1, 3, 8, or 24 h post-dose) were collected from each group. The terminal bleed (approximately 0.6–0.8 mL) was collected by cardiac puncture following ketamine/xylazine anasthesia. The blood was transferred to an EDTA-coated collection tube and centrifuged to obtain plasma. At termination, the liver and kidneys were collected from each mouse. Plasma and tissue homogenates were used for analysis to determine intact oligonucleotide content by CGE. All samples were immediately frozen on dry ice after collection and stored at −80 C. until analysis.

Figure 4:
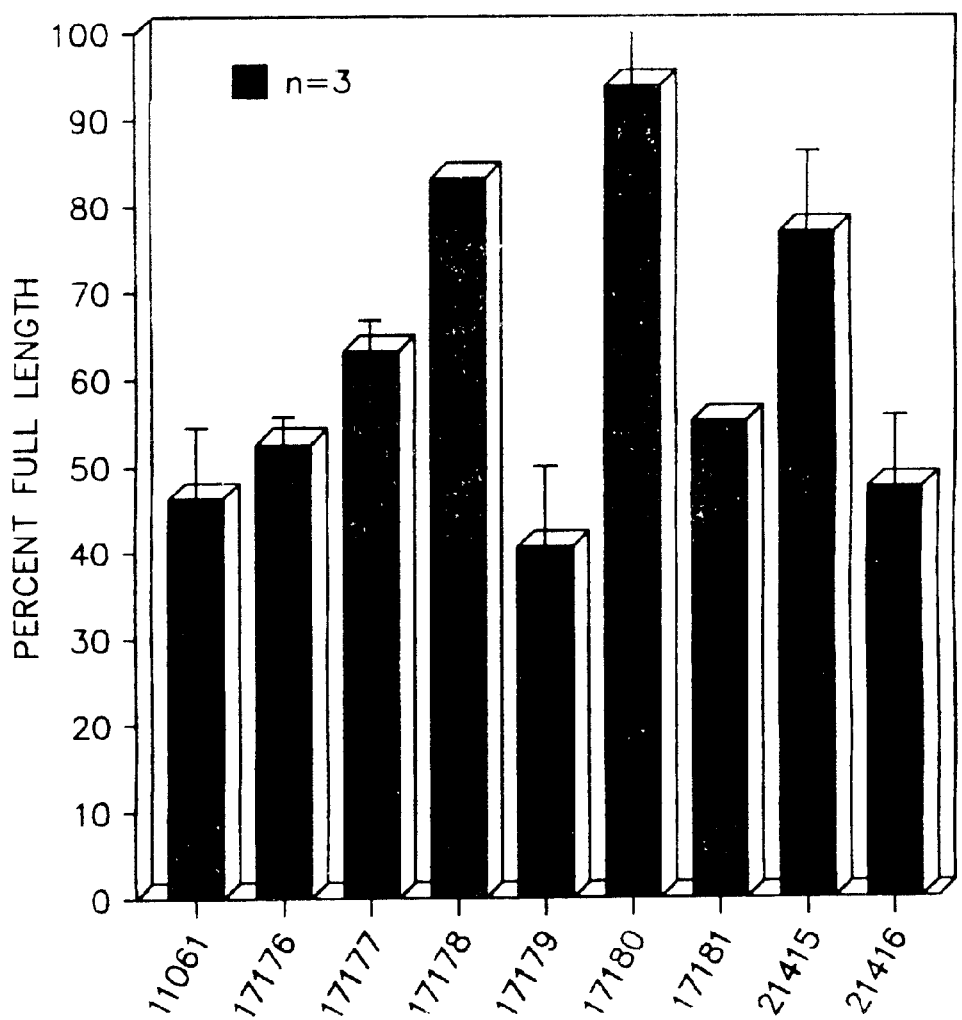
FIG. 4 is a plot of the percentage of full length oligonucleotide remaining intact in plasma one hour following administration of an i.v. bolus of 5 mg/kg oligonucleotide.

This implies that 2',5'-linkages with 3'-methoxyethoxy substituents offer excellent nuclease resistance in plasma, kidney and liver against 5'-exonucleases and 3'-exonucleases. Thus oligonucleotides with longer durations of action can be designed by incorporating both the 2',5'-linkage and 3'-methoxyethoxy motifs into their structure. It was also observed that 2',5'-phosphorothioate linkages are more stable than 2',5'-phosphodiester linkages. A plot of the percentage of full length oligonucleotide remaining intact in plasma one hour following administration of an i.v. bolus of 5 mg/kg oligonucleotide is shown in FIG. 4.

Figure 5:
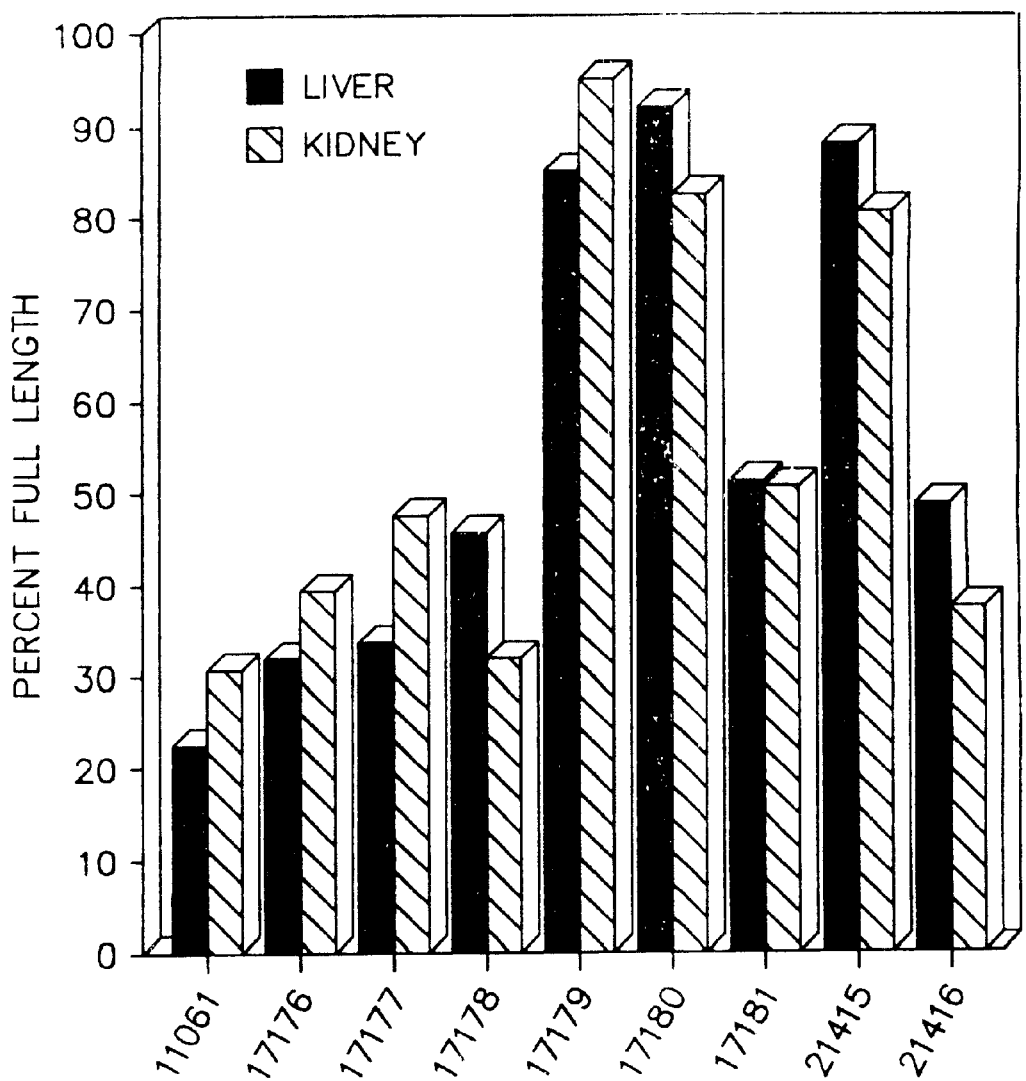
FIG. 5 is a plot of the percentage of full length oligonucleotide remaining intact in tissue 24 hours following administration of an i.v. bolus of 5 mg/kg oligonucleotide.

A plot of the percentage of full length oligonucleotide remaining intact in tissue 24 hours following administration of an i. v. bolus of 5 mg/kg oligonucleotide is shown in FIG. 5.

Figure 6:
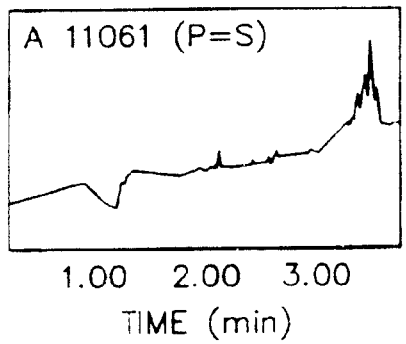
FIG. 6 shows CGE traces of test oligonucleotides and a standard phosphorothioate oligonucleotide in both mouse liver samples and mouse kidney samples after 24 hours.
Figure 6:
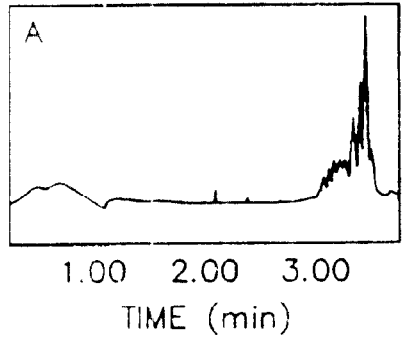
Figure 6:
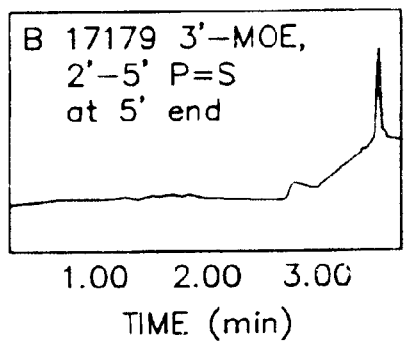
Figure 6:
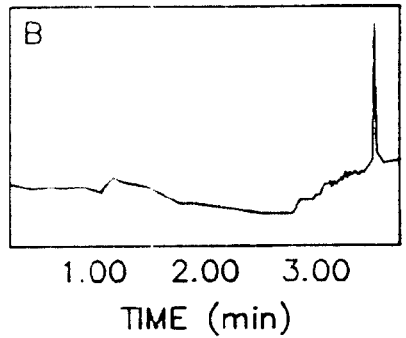
Figure 6:
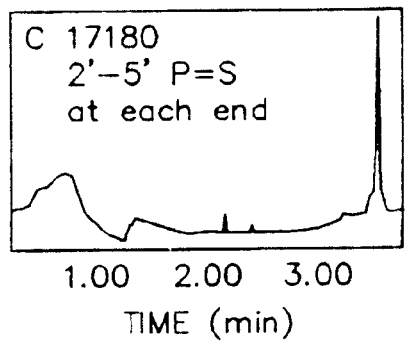
Figure 6:
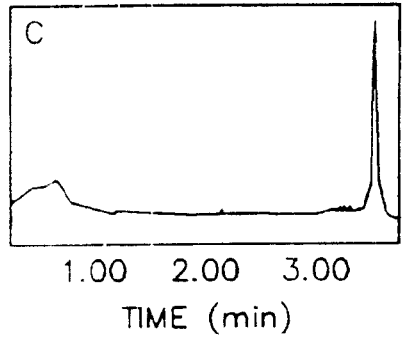
Figure 6:
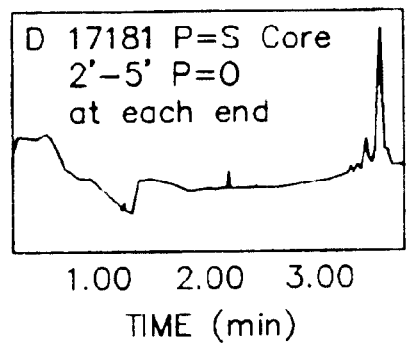
Figure 6:
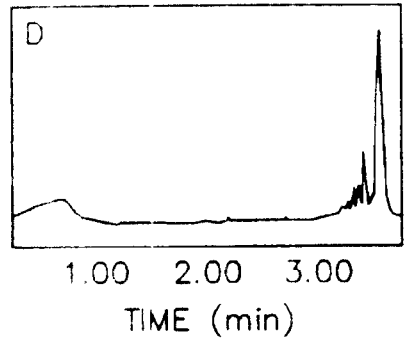

CGE traces of test oligonucleotides and a standard phosphorothioate oligonucleotide in both mouse liver samples and mouse kidney samples after 24 hours are shown in FIG. 6. As is evident from these traces, there is a greater amount of intact oliogonucleotide for the oligonucleotides of the invention as compared to the standard seen in panel A. The oligonucleotide shown in panel B included one substituent of the invention at each of the 5' and 3' ends of a phosphorothioate oligonucleotide while the phosphorothioate oligonucleotide seen in panel C included one substituent at the 5' end and two at the 3' end. The oligonucleotide of panel D includes a substituent of the invention incorporated in a 2',5' phosphodiester linkage at both its 5' and 3' ends. While less stable than the oligonucleotide seen in panels B and C, it is more stable than the full phosphorothioate standard oligonucleotide of panel A.

EXAMPLE 57
Control of c-raf Message in bEND Cells Using Modified Oligonucleotides In order to assess the activity of some of the oligonucleotides, an in vitro cell culture assay was used that measures the cellular levels of c-raf expression in bEND cells.

Cells and Reagents

The bEnd.3 cell line, a brain endothelioma, was obtained from Dr. Werner Risau (Max-Planck Institute). Opti-MEM, trypsin-EDTA and DMEM with high glucose were purchased from Gibco-BRL (Grand Island, N.Y.). Dulbecco's PBS was purchased from Irvine Scientific (Irvine, Calif.). Sterile, 12 well tissue culture plates and Facsflow solution were purchased from Becton Dickinson (Mansfield, Mass.). Ultrapure formaldehyde was purchased from Polysciences (Warrington, Pa.). NAP-5 columns were purchased from Pharmacia (Uppsala, Sweden).

Oligonucleotide Treatment

Cells were grown to approximately 75% confluency in 12 well plates with DMEM containing 4.5 g/L glucose and 10% FBS. Cells were washed 3 times with Opti-MEM prewarmed to 37° C. Oligonucleotide were premixed with a cationic lipid (Lipofectin reagent, (GIBCO/BRL) and, serially diluted to desired concentrations and transferred on to washed cells for a 4 hour incubation at 37° C. Media was then removed and replaced with normal growth media for 24 hours for northern blot analysis of mRNA.

Northern Blot Analysis

Figure 7:
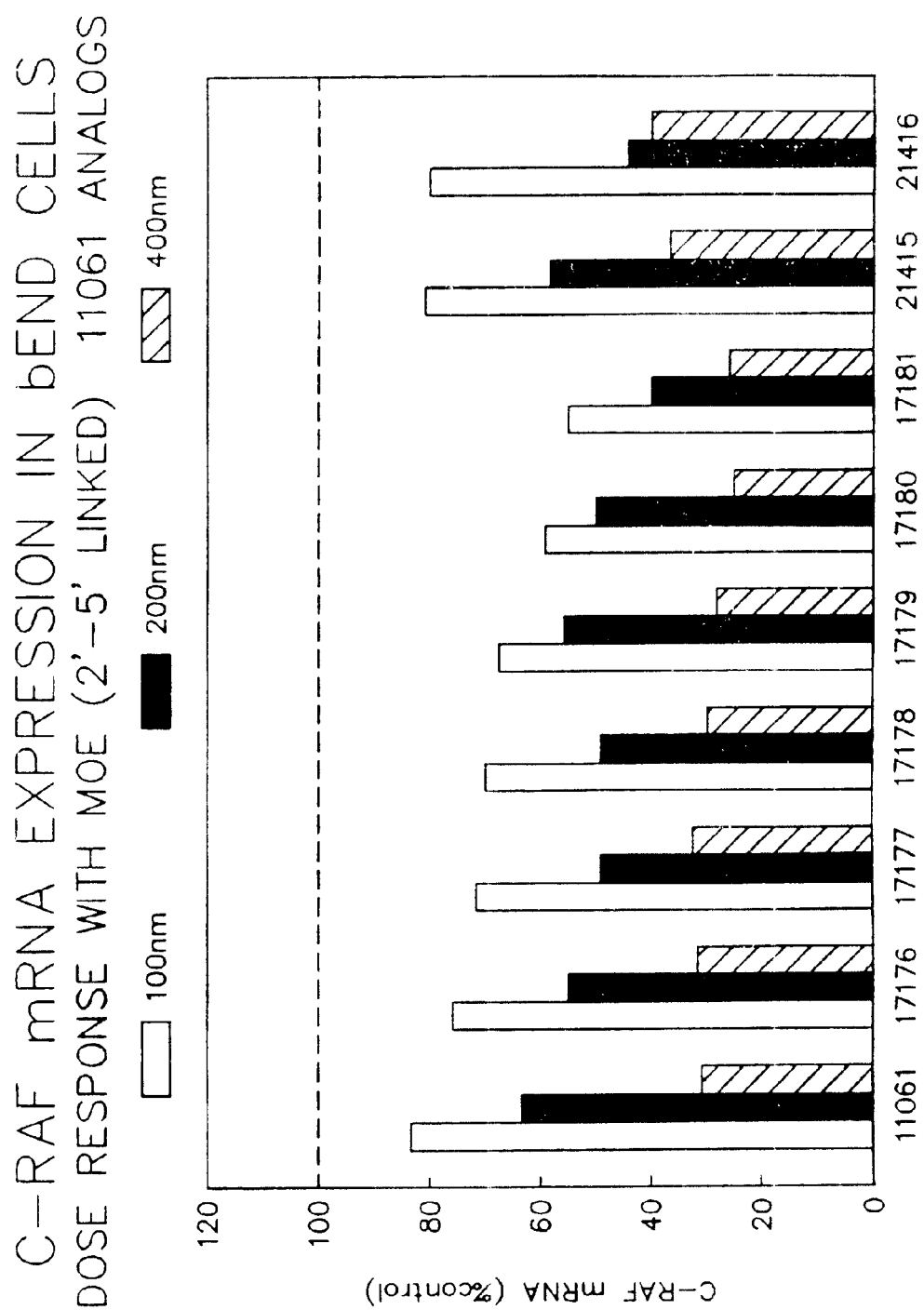
FIG. 7 shows a graph of the effect of the oligonucleotides of the present invention on c-raf expression (compared to control) in bEND cells.

For determination of mRNA levels by Northern blot analysis, total RNA was prepared from cells by the guanidinium isothiocyanate procedure (Monia et al., *Proc. Natl. Acad. Sci. USA*, 1996, 93, 15481–15484) 24 h after initiation of oligonuclcotide treatment. Total RNA was isolated by centrifugation of the cell lysates over a CsCl cushion. Northern blot analysis, RNA quantitation and normalization to G#PDH mRNA levels were done according to a reported procedure (Dean and McKay, *Proc. Natl. Acad. Sci. USA*, 1994, 91, 11762–11766). In bEND cells the 2-,5-linked-3'-O-methoxyethyl oligonucleotides showed reduction of c-raf message activity as a function of concentration. The fact that these modified oligonucleotides retained activity promises reduced frequency of dosing with these oligonucleotides which also show increased in vivo nuclease resistance. All 2',5'-linked oligonucleotides retained the activity of parent 11061 (Table III) oligonucleotide and improved the activity even further. A graph of the effect of the oligonucleotides of the present invention on c-raf expression (compared to control) in bEND cells is shown in FIG. 7.

EXAMPLE 58

Synthesis of MMI-Containing Oligonucleotides a. Bis-2'-O-Methyl MMI Building Blocks The synthesis of MMI (i.e., R=CH$_3$) dimer building blocks have been previously described (see, e.g., Swayze, et al., *Synlett* 1997, 859; Sanghvi, et al., *Nucleosides & Nucleotides* 1997, 16 907; Swayze, et al., *Nucleosides & Nucleotides* 1997, 16, 971; Dimock, et al., *Nucleosides & Nucleotides* 1997, 16, 1629). Generally, 5'-O-(4,4'-dimethoxytrityl)-2'-O-methyl-3'-C-formyl nucleosides were condensed with 5'-O—(N-methylhydroxylamino)-2'-O-methyl-3'-O-TBDPS nucleosides using 1 equivalent of BH$_3$ pyridine/1 equivalent of pyridinium para-toluene sulfonate (PPTS) in 3:1 MeOH/THF. The resultant MMI dimer blocks were then deprotected at the lower part of the sugar with 15 equivalents of Et$_3$N-2HF in THF. Thus the T*G$^{iBu}$ dimer unit was synthesized and phosphitylated to give T*G(MMI) phosphoramidite. In a similar fashion, A$^{BZ}$*T(MMI) dimer was synthesized, succinylated and attached to controlled pore glass.

b. Oligonucleotide Synthesis

Oligonucleotides were synthesized on a Perseptive Biosystems Expedite 8901 Nucleic Acid Synthesis System. Multiple 1-μmol syntheses were performed for each oligonucleotide. A*$_{MMI}$T solid support was loaded into the column. Trityl groups were removed with trichloroacetic acid (975 μL over one minute) followed by an acetonitrile wash. The oligonucleotide was built using a modified thioate protocol. Standard amidites were delivered (210 μL) over a 3 minute period in this protocol. The T*$_{MMI}$G amidite was double coupled using 210 μL over a total of 20 minutes. The amount of oxidizer, 3H-1,2-benzodithiole-3-one-1,1-dioxide (Beaucage reagent, 3.4 g Beaucage reagent/200 mL acetonitrile), was 225 μL (one minute wait step). The unreacted nucleoside was capped with a 50:50 mixture of tetrahyrdofuran/acetic anhydride and tetrahydrofuran/pyridine/1-methyl imidazole. Trityl yields were followed by the trityl monitor during the duration of the synthesis. The final DMT group was left intact. After the synthesis, the contents of the synthesis cartridge (1 μmole) were transferred to a Pyrex vial and the oligonucleotide was cleaved from the controlled pore glass (CPG) using 5 mL of 30% ammonium hydroxide (NH$_4$OH) for approximately 16 hours at 55° C.

C. Oligonucleotide Purification

After the deprotection step, the samples were filtered from CPG using Gelman 0.45 μm nylon acrodisc syringe filters. Excess NH$_4$OH was evaporated away in a Savant AS 160 automatic SpeedVac. The crude yield was measured on a Hewlett Packard 8452A Diode Array Spectrophotometer at 260 nm. Crude samples were then analyzed by mass spectrometry (MS) on a Hewlett Packard electrospray mass spectrometer. Trityl-on oligonucleotides were purified by reverse phase preparative high performance liquid chromatography (HPLC). HPLC conditions were as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/min flow rate; Gradient: 5% B for first five minutes with linear increase in B to 60% during the next 55 minutes. Fractions containing the desired product (retention time=41 min. for DMT-ON-16314; retention time=42.5 min. for DMT-ON-16315) were collected and the solvent was dried off in the SpeedVac. Oligonucleotides were detritylated in 80% acetic acid for approximately 60 minutes and lyophilized again. Free trityl and excess salt were removed by passing detritylated oligonucleotides through Sephadex G-25 (size exclusion chromatography) and collecting appropriate samples through a Pharmacia fraction collector. The solvent was again evaporated away in a SpeedVac. Purified oligonucleotides were then analyzed for purity by CGE, HPLC (flow rate: 1.5 mL/min; Waters Delta Pak C4 column, 3.9×300 mm), and MS. The final yield was determined by spectrophotometer at 260 nm.

The synthesized oligonucleotides and their physical characteristics are shown, respectively, in Tables VIII and IX. All nucleosides with an asterisk contain MMI linkage.

TABLE VIII

ICAM-1 Oligonucleotides Containing MMI Dimers Synthesized for in Vivo Nuclease and Pharmacology Studies.

| SEQ ID NO. # | (ISIS)# | Sequence (5'-3') | Backbone | 2'-Chemistry |
|---|---|---|---|---|
| 21 | (16134) | TGC ATC CCC CAG GCC ACC | P=S, MMI | Bis-2'-OMe-MMI, A*T 2'-H |
| 22 | (16315) | T*GC ATC CCC CAG GCC | P=S, MMI | Bis-2'-OMe-MMI, ACCA*T2'-H |

TABLE VIII-continued

ICAM-1 Oligonucleotides Containing MMI Dimers Synthesized for in Vivo Nuclease and Pharmacology Studies.

| SEQ ID NO. # | (ISIS)# | Sequence (5'-3') | Backbone | 2'-Chemistry |
|---|---|---|---|---|
| 23 | (3082) | TGC ATC CCC CAG GCG ACC | P=S | 2'-H, single AT mismatch |
| 23 | (13001) | TGC ATC CCC CAG GCC ACC | P=S | 2'-H AT |

TABLE IX

Physical Characteristics of MMI Oligomers Synthesized for Pharmacology, and In Vivo Nuclease Studies

| SEQ ID NO. # | (ISIS)# | Sequence (5'-3') | Expected mass (g) | Observed Mass (g) | HPLC Time (min) Retn. |
|---|---|---|---|---|---|
| 21 | (16314) | TGC ATC CCC CAG GCC ACC A*T | 6295 | 6297 | 23.9 |
| 22 | (16315) | T*G C ATC CCC CAG GCC ACC A*T | 6302 | 6303 | 24.75 |

HPLC Conditions: Waters 600E with detector 991; Waters C4 column (3.9×300 mm); Solvent A: 50 mM TEA-Ac, pH 7.0; B: 100% acetonitrile; 1.5 mL/min. flow rate; Gradient: 5% B for first five minutes with linear increase in B to 60% during the next 55 minutes.

EXAMPLE 59

Synthesis of Sp Terminal Oligonucleotide a. 3'-O-t-Butyldiphenylsilyl-thymidine (1)

5'-O-Dimethoxytritylthymidine is silylated with 1 equivalent of t-butyldiphenylsilyl chloride (TBDPSCl) and 2 equivalents of imidazole in DMF solvent at room temperature. The 5'-protecting group is removed by treating with 3% dichloracetic acid in $CH_2Cl_2$.

b. 5'-O-Dimethoxytrityl-thymidin-3'-O-yl-N,N-diisopropylamino (S-pivaloyl-2-mercaptoethoxy) phosphoramidite (2)

5'-O-Dimethoxytrityl thymidine is treated with bis-(N,N-diisopropylamino)-S-pivaloyl-2-mercaptoethoxy phosphoramidite and tetrazole in $CH_2Cl_2/CH_3CN$ as described by Guzaev et al., *Bioorganic & Medicinal Chemistry Letters* 1998, 8, 1123) to yield the title compound.

c. 5'-O-Dimethoxytrityl-2'-deoxy-adenosin-3'-O-yl-N,N-diisopropylamino (S-pivaloyl-2-mercapto Ethoxy) Phosphoramidite (3)

5'-O-Dimethoxytrityl-N-6-benzoyl-2'-deoxy-adenosine is phosphitylated as in the previous example to yield the desired amidite.

d. 3'-O-t-Butyldiphenylsilyl-2'-deoxy-$N_2$-isobutyryl-guanosine (4)

5'-O-Dimethoxytrityl-2'-deoxy-$N_2$-isobutyryl-guanisine is silylated with TBDPSCl and imidazole in DMF. The 5'-DMT is then removed with 3% DCA in $CH_2Cl_2$.

e. $T_{(Sp)}G$ Dimers and $T_{(S)}$ Phosphoramidite

Compounds 4 and 2 are condensed (1:1 equivalents) using 1H-tetrazole in $CH_3CN$ solvent followed by sulfurization employing Beaucage reagent (see, e.g., Iyer, et al., *J. Org. Chem.* 1990, 55, 4693). The dimers (TG) are separated by column chromatography and the silyl group is deprotected using t-butyl ammonium fluoride/THF to give Rp and Sp dimers of $T_sG$. Small amounts of these dimers are completely deprotected and treated with either P1 nuclease or snake venom phosphodiesterase. The R isomer is resistant to P1 nuclease and hydrolyzed by SVPD. The S isomer is resistant to SVPD and hydrolyzed P1 nuclease. The Sp isomer of the fully protected $T_sG$ dimer is phosphitylated to give DMT-T-Sp-G-phosphoramidite.

f. AST Dimers and Solid Support Containing $A_{SP}$ Dimer

Compounds 3 and 1 are condensed using 1H-tetrazole in $CH_3CN$ solvent followed by sulfurization to give AT dimers. The dimers are separated by column chromatography and the silyl group is deprotected with TBAF/THF. The configurational assignments are done generally as in the previous example. The Sp isomer is then attached to controlled pore glass according to standard procedures to give DMT-Asp-$T_{SP}$-CPG oligomerization with chirally pure Sp dimer units at the termini.

g. Oligonucleotide Synthesis

The oligonucleotide having the sequence T*GC ATC CCC CAG GCC ACC A*T SEQ ID NO: 22 is synthesized, where T*G and A*T represent chiral Sp dimer blocks described above. DMT-Asp-T—CPG is taken in the synthesis column and the next 16b residues are built using standard phosphorothioate protocols and 3H-1,2-benzodithiol-3-one 1,1 dioxide as the sulfurizing agent. After building this 18 mer unit followed by final detritylation, the chiral Sp dimer phosphoramidite of 5'-DMT-Tsp-G amidite is coupled to give the desired antisense oligonucleotide. This compound is then deprotected in 30% $NH_4OH$ over 16 hours and the oligomer purified in HPLC and desalted in Sephader G-25 column. The final oligomer has Sp configuration at the 5'-terminus and 3'-terminus and the interior has diastereomeric mixture of Rp and Sp configurations.

EXAMPLE 60

Evaluation of in Vivo Stability of MMI Capped Oligonucleotides Mouse Experiment Procedures For each oligonucleotide tested, 9 male BALB/c mice (Charles River, Wilmington, Mass.), weighing about 25 g was used (Crooke et al., *J. Pharmacol. Exp. Ther.*, 1996, 277, 923). Following a 1-week acclimation, mice received a single tail vein injection of oligonucleotide (5 mg/kg) administered in phosphate buffered saline (PBS), pH 7.0 One retro-orbital bleed (either 0.25, 0.5, 2 or 4 lv post dose) and a terminal bleed (either 1, 3, 8 or 24 h post dose) were collected from each group. The terminal bleed (approximately 0.6–0.8 mL) was collected by cardiac puncture following ketamine/xylazine anesthesia. The blood was transferred to an EDTA-coated collection tube and centrifuged to obtain plasma. At termination, the liver and kidneys were collected from each mouse. Plasma and tissues homogenates were used for analysis for determination of intact oligonucleotide content by CGE. All samples were immediately frozen on dry ice after collection and stored at −80° C. until analysis.

The capillary gel electrophoretic analysis indicated the relative nuclease resistance of MMI capped oligomers compared to ISIS 3082 (uniform 2'-deoxy phosphorothioate). Because of the resistance of MMI linkage to nucleases, the compound 16314 was found to be stable in plasma while 3082 was not. However, in kidney and liver, the compound 16314 also showed certain amount of degradation. This implied that while 3'-exonuclease is important in plasma, 5'-exonucleases or endonucleases may be active in tissues.

To distinguish between these two possibilities, the data from 16315 was analyzed. In plasma as well as in tissues, (liver and kidney) the compound was stable in various time points. (1, 3 and 24 hrs.). The fact that no degradation was detected proved that 5'-exonucleases and 3'-exonuclease are prevalent in tissues and endonucleases are not active. Furthermore, a single linkage (MMI or Sp thioate linkage) is sufficient as a gatekeeper against nucleases.

Control of ICAM-1 Expression Cells and Reagents

The bEnd.3 cell line, a brain endothelioma, was the kind gift of Dr. Werner Risau (Max-Planck Institute). Opti-MEM, trypsin-EDTA and DMEM with high glucose were purchased from Gibco-BRL (Grand Island, N.Y.). Dulbecco's PBS was purchased from Irvine Scientific (Irvine, Calif.). Sterile, 12 well tissue culture plates and Facsflow solution were purchased from Becton Dickinson (Mansfield, Mass.). Ultrapure formaldehyde was purchased from Polysciences (Warrington, Pa.). Recombinant human TNF-α was purchased from R&D Systems (Minneapolis, Minn.). Mouse interferon-γ was purchased from Genzyme (Cambridge, Mass.). Fraction V, BSA was purchased from Sigma (St. Louis, Mo.). The mouse ICAM-1-PE, VCAM-1-FITC, hamster IgG-FITC and rat $IgG_{2a}$-PE antibodies were purchased from Pharmingen (San Diego, Calif.). Zeta-Probe nylon blotting membrane was purchased from Bio-Rad (Richmond, Calif.). QuickHyb solution was purchased from Stratagene (La Jolla, Calif.). A cDNA labeling kit, Prime-a-Gene, was purchased from ProMega (Madison, Wis.). NAP-5 columns were purchased from Pharmacia (Uppsala, Sweden).

Oligonucleotide Treatment

Cells were grown to approximately 75% confluency in 12 well plates with DMEM containing 4.5 g/L glucose and 10% FBS. Cells were washed 3 times with Opti-MEM prewarmed to 37° C. Oligonucleotide was premixed with Opti-MEM, serially diluted to desired concentrations and transferred onto washed cells for a 4 hour incubation at 37° C. Media was removed and replaced with normal growth media with or without 5 ng/mL TNF-α and 200 U/mL interferon-γ, incubated for 2 hours for northern blot analysis of mRNA or overnight for flow cytometric analysis of cell surface protein expression.

Flow Cytometry

After oligonucleotide treatment, cells were detached from the plates with a short treatment of trypsin-EDTA (1–2 min.). Cells were transferred to 12×75 mm polystyrene tubes and washed with 2% BSA, 0.2% sodium azide in D-PBS at 4° C. Cells were centrifuged at 1000 rpm in a Beckman GPR centrifuge and the supernatant was then decanted. ICAM-1, VCAM-1 and the control antibodies were added at 1 ug/mL in 0.3 mL of the above buffer. Antibodies were incubated with the cells for 30 minutes at 4° C. in the dark, under gentle agitation. Cells were washed again as above and then resuspended in 0.3 mL of FacsFlow buffer with 0.5% ultrapure formaldehyde. Cells were analyzed on a Becton Dickinson FACScan. Results are expressed as percentage of control expression, which was calculated as follows: [((CAM expression for oligonucleotide-treated cytokine induced cells)–(basal CAM expression))/((cytokine-induced CAM expression)–(basal CAM expression))]×100. For the experiments involving cationic lipids, both basal and cytokine-treated control cells were pretreated with Lipofectin for 4 hours in the absence of oligonucleotides.

The results reveal the following: 1) Isis 3082 showed an expected dose response (25–200 nM); 2) Isis 13001 lost its ability to inhibit ICAM-1 expression as expected from a mismatch compound, thus proving an antisense mechanism; 3) 3'-MMI capped oligomer 16314 improved the activity of 3082, and at 200 nM concentration, nearly twice as active as 3082; 4) 5'- and 3'-MMI capped oligomer is the most potent compound and it is nearly 4 to 5 times more efficacious than the parent compound at 100 and 200 nM concentrations. Thus, improved nuclease resistance increased the potency of the antisense oligonucleotides.

EXAMPLE 61

Control of H-ras Expression

Figure 8:
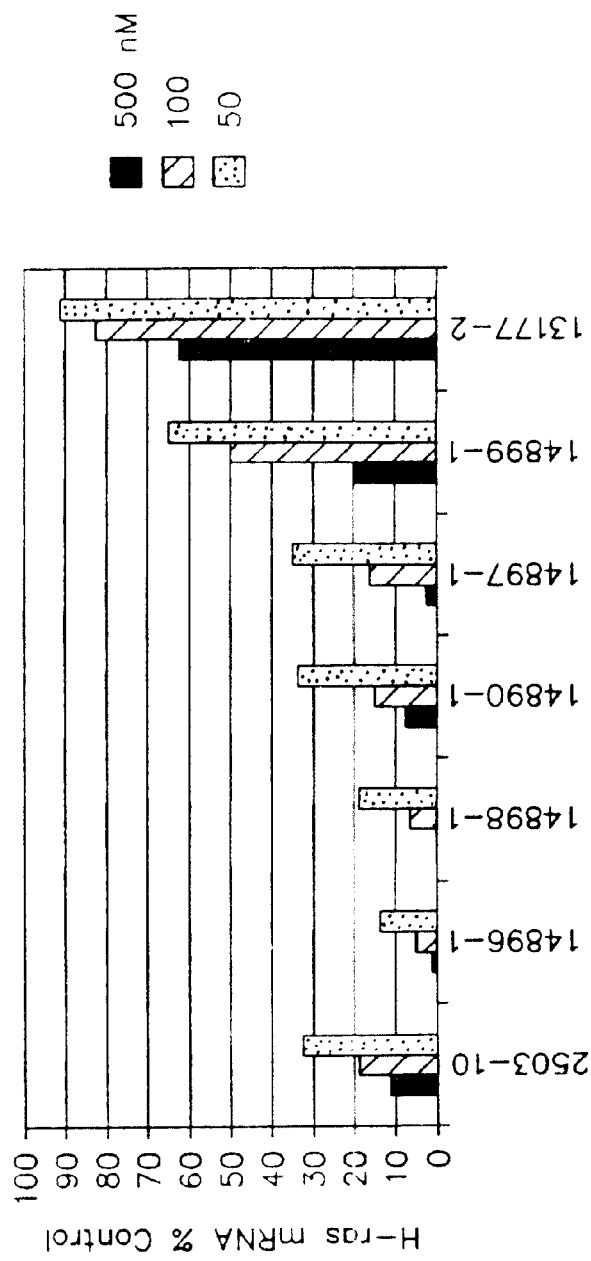
FIGS. 8 and 9 shows bar graphs as percent control normalized for the G3PDH signal eighteen hours after treatment with specified compounds.
Figure 9:
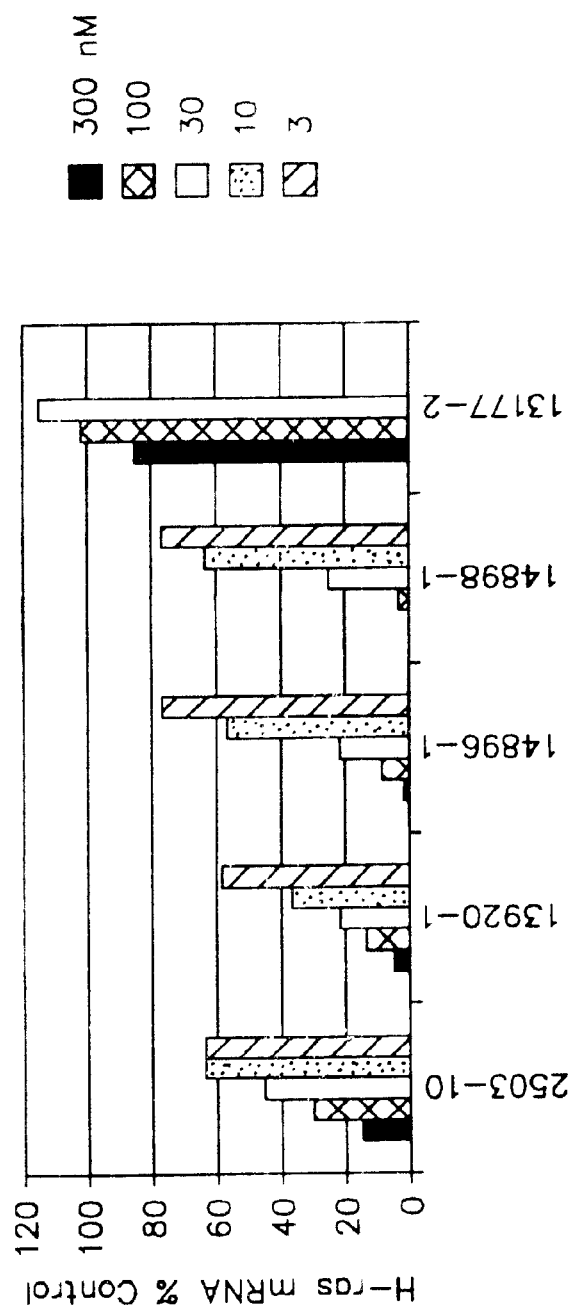

Antisense oligonucleotides targeting the H-ras message were tested for their ability to inhibit production of H-ras mRNA in T-24 cells. For these test, T-24 cells were plated in 6-well plates and then treated with various escalating concentrations of oligonucleotide in the presence of cationic lipid (Lipofectin, GIBCO) at the ratio of 2.5 μg/ml Lipofectin per 100 nM oligonucleotide. Oligonucleotide treatment was carried out in serum free media for 4 hours. Eighteen hours after treatment the total RNA was harvested and analyzed by northern blot for H-ras mRNA and control gene G3PDH. The data is presented in FIGS. 8 and 9 in bar graphs as percent control normalized for the G3PDH signal. As can be seen, the oligonucleotide having a single MMI linkage in each of the flank regions showed significant reduction of H-ras mRNA.

EXAMPLE 62

5-Lipoxygenase Analysis and Assays

A. Therapeutics

For therapeutic use, an animal suspected of having a disease characterized by excessive or abnormal supply of 5-lipoxygenase is treated by administering a compound of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotides of the invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 30 to about 50° C. The cleaved 5-lipoxygenase RNA can be analyzed by agarose gel electrophoresis and hybridization with radiolabeled DNA probes or by other standard methods.

C. Diagnostics

The oligonucleotides of the invention will also be useful in diagnostic applications, particularly for the determination of the expression of specific mRNA species in various tissues or the expression of abnormal or mutant RNA species. In this example, while the macromolecules target a abnormal mRNA by being designed complementary to the abnormal sequence, they would not hybridize to normal mRNA. Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotides which interfere with 5-lipoxygenase synthesis in these cells.

A second test system for oligonucleotides makes use of the fact that 5-lipoxygenase is a "suicide" enzyme in that it inactivates itself upon reacting with substrate. Treatment of differentiated HL-60 or other cells expressing 5 lipoxygenase, with 10 $\mu$M A23 187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Macromolecules directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

A direct effect which oligonucleotides can exert on intact cells and which can be easily be quantitated is specific inhibition of 5-lipoxygenase protein synthesis. To perform this technique, cells can be labeled with $^{35}$S-methionine (50 $\mu$Ci/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 $\mu$M, 10 $\mu$M, and 30 $\mu$M of the macromolecules of the invention for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000× g for 30 min and the supernatants analyzed for 5-lipoxygenase activity. Cytosolic proteins are incubated with 10 $\mu$M $^{14}$C-arachidonic acid, 2 mM ATP, 50 $\mu$M free calcium, 100 $\mu$g/mL phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective the macromolecules of the invention at 1 $\mu$M, 10 $\mu$M, and 30 $\mu$M would be as follows. Control cells oxidize 200 pmol arachidonic acid/5 min/$10^6$ cells. Cells treated with 1 $\mu$M, 10 $\mu$M, and 30 $\mu$M of an effective oligonucleotide would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. Purified 5-lipoxygenase (25 ng) is bound to the microtiter plates overnight at 4° C. The wells are blocked for 90 min with 5% goat serum diluted in 20 mM Tris!HCL buffer, pH 7.4, in the presence of 150 mM NaCl (TBS). Cell extracts (0.2% Triton X-100, 12,000× g for 30 min.) or purified 5-lipoxygenase were incubated with a 1:4000 dilution of 5-lipoxygenase polyclonal antibody in a total volume of 100 $\mu$L in the microtiter wells for 90 min. The antibodies are prepared by immunizing rabbits with purified human recombinant 5-lipoxygenase. The wells are washed with TBS containing 0.05% tween 20 (TBST), then incubated with 100 $\mu$L of a 1:1000 dilution of peroxidase conjugated goat anti-rabbit IgG (Cappel Laboratories, Malvern, Pa.) for 60 min at 25° C. The wells are washed with TBST and the amount of peroxidase labeled second antibody determined by development with tetramethylbenzidine.

Predicted results from such an assay using a 30 mer oligonucleotide at 1 $\mu$M, 10 $\mu$M, and 30 $\mu$M would be 30 ng, 18 ng and 5 ng of 5-lipoxygenase per $10^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells ($2\times10^5$ cells/mL) will be treated with increasing concentrations of the macromolecule for 48–72 hours in the presence of 1.3% DMSO. The cells are washed and resuspended at a concentration of $2\times10^6$ cell/mL in Dulbecco's phosphate buffered saline containing 1% delipidated bovine serum albumin. Cells are stimulated with 10 μM calcium ionophore A23187 for 15 min and the quantity of LTB4 produced from $5\times10^5$ cell determined by radioimmunoassay as described by the manufacturer.

Using this assay the following results would likely be obtained with an oligonucleotide directed to the 5-LO mRNA. Cells will be treated for 72 hours with either 1 μM, 10 μM or 30 μM of the macromolecule in the presence of 1.3% DMSO. The quantity of $LTB_4$ produced from $5\times10^5$ cells would be expected to be about 75 pg, 50 pg, and 35 pg, respectively with untreated differentiated cells producing 75 pg $LTB_4$.

E. In Vivo Assay

Inhibition of the production of 5-lipoxygenase in the mouse can be demonstrated in accordance with the following protocol. Topical application of arachidonic acid results in the rapid production of leukotriene $B_4$, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by mycloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Oligonucleotides will be applied topically to both ears 12 to 24 hours prior to administration of arachidonic acid to allow optimal activity of the compounds. Both ears are pretreated for 24 hours with either 0.1 μmol, 0.3 μmol, or 1.0 μmol of the macromolecule prior to challenge with arachidonic acid. Values are expressed as the mean for three animals per concentration. Inhibition of polymorphonuclear cell infiltration for 0.1 μmol, 0.3 μmol, and 1 μmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

EXAMPLE 63

5'-O-DMT-2'-deoxy-2'-methylene-5-methyl uridine-3'-(2-cyanoethyl-N,N-diisoproppyl) phosphoramidite 2'-Deoxy-2'-methylene-3',5'-O-(tetraisopropyl disiloxane-1,3,diyl)-5-methyl uridine is synthesized following the procedures reported for the corresponding uridine derivative (Hansske, F.; Madej, D.; Robins, M. J. Tetrahedron (1984) 40, 125; Matsuda, A.; Takenusi, K.; Tanaka, S.; Sasaki, T.; Ueda, T. J. Med. Chem. (1991) 34, 812; See also Cory, A. H.; Samano, V.; Robins, M. J.; Cory, J. G. 2'-Deoxy-2'-methylene derivatives of adenosine, guanosine, tubercidin, cytidine and uridine as inhibitors of L1210 cell growth in culture. Biochem. Pharmacol. (1994), 47(2), 365–71.)

It is treated with IM TBAF in THF to give 2'-deoxy-2'-methylene-5-methyl uridine. It is dissolved in pyridine and treated with DMT-Cl and stirred to give the 5'-O-DMT-2'-deoxy-2'-methylene-5-methyl uridine. This compound is treated with 2-cyanoethyl-N,N-diisopropyl phosphoramidite and diisopropylaminotetrazolide. In a similar manner the corresponding N-6 benzoyl adenosine, N-4-benzoyl cytosine, N-2-isobutyryl guanosine phosphoramidite derivatives are synthesized.

EXAMPLE 63

Synthesis of 3'-O-4'-C-methyleneribonucleoside

5'-O-DMT-3'-O-4'-C-methylene uridine and 5-methyl uridine are synthesized and phosphitylated according to the procedure of Obika et al. (Obika et al. Bioorg. Med. Chem. Lett. (1999) 9, 515–158). The amidites are incorporated into oligonucleotides using the protocols described above.

EXAMPLE 64

Synthesis of 2'-methylene Phosphoramidites

5'-O-DMT-2'-(methyl)-3'-O-(2-cyanoethyl-N,N-diisopropylamine)-5-methyluridine-phosphoramidite, 5'-O-DMT-2'-(methyl)-N-6-benzoyl adenosine (3'-O-2-cyanoethyl-N,N-diisopropylamino) phosphoramidite, 5'-O-DMT-2'-(methyl)-N-2-isoburytyl guanosine-3'-O-(2-cyanoethyl-N,N-diisopropylamino) phosphoramidite and 5'-O-DMT-2'-(methyl)-N-4-benzoyl cytidine-3'-O-(2-cyanoethyl-N,N-diisopropylamino) phosphoramidites were obtained by the phosphitylation of the corresponding nucleosides. The nucleosides were synthesized according to the procedure described by Iribarren, Adolfo M.; Cicero, Daniel O.; Neuner, Philippe J. Resistance to degradation by nucleases of (2'S)-2'-deoxy-2'-C-methyloligonucleotides, novel potential antisense probes. Antisense Res. Dev., (1994), 4(2), 95–8; Schmit, Chantal; Bevierre, Marc-Olivier; De Mesmaeker, Alain; Altmann, Karl-Heinz. "The effects of 2'- and 3'-alkyl substituents on oligonucleotide hybridization and stability". Bioorg. Med. Chem. Lett. (1994), 4(16), 1969–74.

The phosphitylation is carried out by using the bisamidite procedure.

EXAMPLE 65

Synthesis of 2'-S-methyl Phosphoramidites

5'-O-DMT-2'-S-(methyl)-3'-O-(2-cyanoethyl-N,N-diisopropylamine)-5-methyl uridine-phosphoramidite, 5'-O-DMT-2'-S(methyl)-N-6-benzoyl adenosine (3'-O-2-cyanoethyl-N,N-diisopropylamino) phosphoramidite, 5'-O-DMT-2'-S-(methyl)-N-2-isoburytyl guanosine-3'-O-(2-cyanoethyl-N,N-diisopropylamino) phosphoramidite and 5'-O-DMT-2'-S-(methyl)-N-4-benzoyl cytidine-3'-O-(2-cyanoethyl-N,N-diisopropylamino) phosphoramidites were obtained by the phosphitylation of the corresponding nucleosides. The nucleosides were synthesized according to the procedure described by Fraser et al. (Fraser, A.; Wheeler, P.; Cook, P. D.; Sanghvi, Y. S. J. Heterocycl. Chem. (1993) 31, 1277–1287). The phosphitylation is carried out by using the bisamidite procedure.

EXAMPLE 66

Synthesis of 2'-O-methyl-β-D-arabinofuranosyl Compounds

2'-O-Methyl-β-D-arabinofuranosyl-thymidine containing oligonucleotides were synthesized following the procedures of Gotfredson et. al. (Gotfredson, C. H. et. al. Tetrahedron Lett. (1994) 35, 6941–6944; Gotfredson, C. H. et. al. Bioorg. Med. Chem. (1996) 4, 1217–1225). 5'-O-DMT-2'-ara-(O-methyl)-3'-O-(2-cyanoethyl-N,N-diisopropylamine)-5-methyl uridine-phosphoramidite, 5'-O-DMT-2'-ara-(O-methyl)-N-6-benzoyl adenosine (3'-O-2-cyanoethyl-N,N-diisopropylamino) phosphoramidite, 5'-O-DMT-2'-ara-(O-methyl)-N-2-isoburytyl guanosine-3'-O-(2-cyanoethyl-N,N-diisopropylamino) phosphoramidite and 5'-O-DMT-2'-ara-(O-methyl)-N-4-benzoyl cytidine-3'-O-(2-cyanoethyl-N,N-diisopropylamino) phosphoramidites are obtained by the phosphitylation of the corresponding nucleosides. The nucleosides are synthesized according to the procedure described by Gotfredson, C. H. et. al. Tetrahedron Lett. (1994) 35, 6941–6944; Gotfredson, C. H. et. al. Bioorg.

Med. Chem. (1996) 4, 1217–1225. The phosphitylation is carried out by using the bisamidite procedure.

EXAMPLE 67
Synthesis of 2'-fluoro-β-D-arabinofuranosyl Compounds

2'-Fluoro-β-D-arabinofuranosyl oligonucleotides are synthesized following the procedures by Kois, P. et al., Nucleosides Nucleotides 12, 1093,1993 and Damha et al., J. Am. Chem. Soc., 120, 12976,1998 and references sited therin. 5'-O-DMT-2'-ara-(fluoro)-3'-O-(2-cyanoethyl-N,N-diisopropylamine)-5-methyl uridine-phosphoramidite, 5'-O-DMT-2'-ara-(fluoro)-N-6-benzoyl adenosine (3'-O-2-cyanoethyl-N,N-diisopropylamino) phosphoramidite, 5'-O-DMT-2'-ara-(fluoro)-N-2-isoburytyl guanosine-3'-O-(2-cyanoethyl-N,N-diisopropylamino) phosphoramidite and 5'-O-DMT-2'-ara-(fluoro)-N-4-benzoyl cytidine-3'-O-(2-cyanoethyl-N,N-diisopropylamino) phosphoramidites are obtained by the phosphitylation of the corresponding nucleosides. The nucleosides are synthesized according to the procedure described by Kois, P. et al., Nucleosides Nucleotides 12, 1093,1993 and Damha et al., J. Am. Chem. Soc., 120, 12976,1998. The phosphitylation is carried out by using the bisamidite procedure.

EXAMPLE 68
Synthesis of 2'-hydroxyl-β-D-arabinofuranosyl Compounds

2'-Hydroxyl-β-D-arabinofuranosyl oligonucleotides are synthesized following the procedures by Resmini and Pfleiderer Helv. Chim. Acta, 76, 158,1993; Schmitt et al., Bioorg. Med. Chem. Lett. 4, 1969, 1994 Resmini, M.; Pfleiderer, W. Synthesis of arabinonucleic acid (tANA). Bioorg. Med. Chem. Lett. (1994), 16, 1910.; Resmini, Matthias; Pfleiderer, W. Nucleosides. Part LV. Efficient synthesis of arabinoguanosine building blocks (Helv. Chim. Acta, (1994), 77, 429–34; and Damha et al., J. Am. Chem. Soc., 1998, 120, 12976, and references sited therin).

5'-O-DMT-2'-ara-(hydroxy)-3'-O-(2-cyanoethyl-N,N-diisopropylamine)-5-methyl uridine-phosphoramidite, 5'-O-DMT-2'-ara-(hydroxy)-N-6-benzoyl adenosine (3'-O-2-cyanoethyl-N,N-diisopropylamino) phosphoramidite, 5'-O-DMT-2'-ara-(hydroxy)-N-2-isoburytyl guanosine-3'-O-(2-cyanoethyl-N,N-diisopropylamino) phosphoramidite and 5'-O-DMT-2'-ara-(hydroxy)-N-4-benzoyl cytidine-3'-O-(2-cyanoethyl-N,N-diisopropylamino) phosphoramidites are obtained by the phosphitylation of the corresponding nucleosides. The nucleosides are synthesized according to the procedure described by Kois, P. et al., Nucleosides Nucleotides 12, 1093,1993 and Damha et al., J. Am. Chem. Soc., 120, 12976,1998. The phosphitylation is carried out by using the bisamidite procedure.

EXAMPLE 69
Synthesis of Difluoromethylene Compounds

5'-O-DMT-2'-deoxy-2'-difluoromethylene-5-methyluridine-3'-(2-cyanoethyl-N,N-diisopropyl phosphoramidite), 5'-O-DMT-2'-deoxy-2'-difluoromethylene-N-4-benzoyl-cytidine, 5'-O-DMT-2'-deoxy-2'-diflyoromethylene-N-6-benzoyl adenosine, and 5'-O-DMT-2'-deoxy-2'-difluoroethylene-N₂-isobutyryl guanosine are synthesized following the protocols described by Usman et. al. (U.S. Pat. No. 5,639,649, Jun. 17, 1997).

EXAMPLE 70
Synthesis of 5'-O-DMT-2'-deoxy-2'-β-(O-acetyl)-2'-α-methyl-N-6-benzoyl-adenosine-3'-(2-cyanoethyl-N,N-diisopropyl Phosphoramidite 5'-O-DMT-2'-deoxy-2'-β-(OH)-2'-α-methyl-adenosine is synthesized from the compound 5'–3'-protected-2'-keto-adenosine (Rosenthal, Sprinzl and Baker, Tetrahedron Lett. 4233, 1970; see also Nucleic acid related compounds. A convenient procedure for the synthesis of 2'- and 3'-ketonucleosides is shown Hansske et al., Dep. Chem., Univ. Alberta, Edmonton, Can., Tetrahedron Lett. (1983), 24(15), 1589–92.) by Grigand addition of MeMgI in THF solvent, followed by seperation of the isomers. The 2-β-(OH) is protected as acetate. 5'–3'-acetal group is removed, 5'-position dimethoxy, tritylated, N-6 position is benzoylated and then 3'-position is phosphitylated to give 5'-O-DMT-2'-deoxy-2'-β-(O-acetyl)-2'-α-methyl-N-6-benzoyl-adenosine-3'-(2-cyanoethyl-N,N-diisopropyl) phosphoramidite.

EXAMPLE 71
Synthesis of 5'-O-DMT-2'-α-ethynyl-N-6-benzoyl-adenosine-3'-(2-cyanoethyl-N,N-diisopropyl Phosphoramidite 5'-O-DMT-2'-deoxy-2'-β-(OH)-2'-α-ethynyl-adenosine is synthesized from the compound 5'–3'-protected-2'-keto-adenosine (Rosenthal, Sprinzl and Baker, Tetrahedron Lett. 4233, 1970) by Grigand addition of Ethynyl-MgI in THF solvent, followed by seperation of the isomers. The 2'-β-(OH) is removed by Robins' deoxygenation procedure (Robins et al., J. Am. Chem. Soc. (1983), 105, 4059–65. 5'–3'-acetal group is removed, 5'-position dimethoxytritylated, N-6 position is benzoylated and then 3'-position is phosphitylated to give the title compound.

EXAMPLE 72
2'-O-(guaiacolyl)-5-methyluridine

2-Methoxyphenol (6.2 g, 50 mmol) was slowly added to a solution of borane in tetrahydrofuran (1 M, 10 mL, 10 mmol) with stirring in a 100 mL bomb. Hydrogen gas evolved as the solid dissolved O-2,2'-anhydro-5-methyluridine (1.2 g, 5 mmol), and sodium bicarbonate (2.5 mg) were added and the bomb was sealed, placed in an oil bath and heated to 155° C. for 36 hours. The bomb was cooled to room temperature and opened. The crude solution was concentrated and the residue partitioned between water (200 mL) and hexanes (200 mL). The excess phenol was extracted into hexanes. The aqueous layer was extracted with ethyl acetate (3×200 mL) and the combined organic layer was washed once with water, dried over anhydrous sodium sulfate and concentrated. The residue was purified by silica gel flash column chromatography using methanol-:methylene chloride (1/10, v/v) as the eluent. Fractions were collected and the target fractions were concentrated to give 490 mg of pure product as a white solid. Rf=0.545 in $CH_2Cl_2/CH_3OH$ (10:1). MS/ES for $C_{17}H_{20}N_2O_7$, 364.4; Observed 364.9.

EXAMPLE 73
5'-Dimethoxytrityl-2'-O-(2-methoxyphenyl)-5-methyluridine-3'-O-(2-cyanoethyl-N,N-diisopropylamino) Phosphoramidite 2'-O-(guaiacolyl)-5-methyl-uridine is treated with 1.2 equivalents of dimethoxytrityl chloride (DMT-Cl) in pyridine to yield the 5'-O-dimethoxy tritylated nucleoside. After evaporation of the pyridine and work up ($CH_2Cl_2$/saturated $NaHCO_3$ solution) the compound is purified in a silica gel column. The 5'-protected nucleoside is dissolved in anhydrous methylene chloride and under argon atmosphere, N,N-diisopropyl-aminohydrotetrazolide (0.5 equivalents) and bis-N,N-diisopropylamino-2-cyanoethyl-phosphoramidite (2 equivalents) are added via syringe over 1 min. The reaction mixture is stirred under argon at room temperature for 16 hours and then applied to a silica column. Elution with hexane:ethylacetate (25:75) gives the title compound.

EXAMPLE 74

5'-Dimethoxytrityl-2'-O-(2-methoxyphenyl)-5-methyluridine-3'-O-succinate

The 5'-protected nucleoside from Example 73 is treated with 2 equivalents of succinic anhydride and 0.2 equivalents of 4-N,N-dimethylaminopyridine in pyridine. After 2 hours the pyridine is evaporated, the residue is dissolved in $CH_2Cl_2$ and washed three times with 100 mL of 10% citric acid solution. The organic layer is dried over anhydrous $MgSO_4$ to give the desired succinate. The succinate is then attached to controlled pore glass (CPG) using established procedures (Pon, R. T., Solid phase supports for oligonucleotide synthesis, in *Protocols for Oligonucleotides and Analogs*, S. Agrawal (Ed.), Humana Press: Totawa, N.J., 1993, 465–496).

EXAMPLE 75

5'-Dimethoxytrityl-2'-O-(trans-2-methoxycyclohexyl)-5-methyl Uridine

2'–3'-O-Dibutylstannyl-5-methyl uridine (Wagner et al., *J. Org. Chem.*, 1974, 39, 24) is alkylated with trans-2-methoxycyclohexyl tosylate at 70° C. in DMF. A 1:1 mixture of 2'-O— and 3'-O-(trans-2-methoxycyclohexyl)-5-methyluridine is obtained in this reaction. After evaporation of the DMF solvent, the crude mixture is dissolved in pyridine and treated with dimethoxytritylchloride (DMT-Cl) (1.5 equivalents). The resultant mixture is purified by silica gel flash column chromatography to give the title compound.

EXAMPLE 76

5'-Dimethoxytrityl-2'-O-(trans-2-methoxycyclohexyl)-5-methyluridine-3'-O-(2-cyanoethyl-N,N-diisopropylamino) Phosphoramidite 5'-Dimethoxytrityl-2'-O-(trans-2-methoxycyclohexyl)-5-methyl uridine is phosphitylated according to the procedure described above to give the required phosphoramidite.

EXAMPLE 77

5'-Dimethoxytrityl-2'-O-(trans-2-methoxycyclohexyl)-5-methyluridine-3'-O-(succinyl-amino) CPG 5'-Dimethoxytrityl-2'-O-(trans-2-methoxycyclohexyl)-5-methyl uridine is succinylated and attached to controlled pore glass to give the solid support bound nucleoside.

EXAMPLE 78 trans-2-ureido-cyclohexanol

Trans-2-amino-cyclohexanol (Aldrich) is treated with triphosgene in methylene chloride (⅓ equivalent). To the resulting solution, excess ammonium hydroxide is added to give after work up the title compound.

EXAMPLE 79

2'-O-(trans-2-uriedo-cyclohexyl)-5-methyl Uridine

Trans-2-uriedo-cyclohexanol (50 mmol) is added to a solution of borane in tetrahydrofuran (1 M, 10 mL, 10 mmol) while stirring in a 10 mL bomb. Hydrogen gas evolves as the reactant dissolves. O2,2'-Anhydro-5-methyluridine (5 mmol) and sodium bicarbonate (2.5 mg) are added to the bomb and sealed. Then it is heated to 140 for 72 hrs. The bomb is cooled to room temperature and opened. The crude material was worked up as illustrated above followed by purification by silica gel flash column chromatography to give the title compound.

EXAMPLE 80

5'-O-(Dimethoxytrityl)-2'-O-(trans-2-uriedo-cyclohexyl) 3'-O-(2-cyanoethyl, N,N,-diisopropyl) Uridine Phosphoramidite 2'-O-(trans-2-uriedo-cyclohexyl)-5-methyl uridine tritylated at the 5'-OH and phosphitylated at the 3'-OH following the procedures illustrated in example 2 to give the title compound.

EXAMPLE 81

5'-O-dimethoxytrityl-2'-O-(trans-2-uriedo-cyclohexyl)-5-methyl-3'-O-(succinyl)-amino CPG uridine 5'-O-dimethoxytrityl-2'-O-(trans-2-uriedo-cyclohexyl)-5-methyl uridine is succinylated and attached to CPG as illustrated above.

EXAMPLE 82

2'-O-(trans-2-methoxy-cyclohexyl) Adenosine

Trans-2-methoxycyclopentanol, trans-2-methoxycylcohexanol, trans-2-methoxy-cyclopentyl tosylate and trans-2-methoxy-cyclohexyl tosylate are prepared according to reported procedures (Roberts, D. D., Hendrickson, W., *J. Org. Chem.*, 1967, 34, 2415–2417; *J. Org. Chem.*, 1997, 62, 1857–1859). A solution of adenosine (42.74 g, 0.16 mol) in dry dimethylformamide (800 mL) at 5° C. is treated with sodium hydride (8.24 g, 60% in oil prewashed thrice with hexanes, 0.21 mol). After stirring for 30 min, trans-2-methoxy-cyclohexyl tosylate (0.16 mol) is added over 20 minutes at 5° C. The reaction is stirred at room temperature for 48 hours, then filtered through Celite. The filtrate is concentrated under reduced pressure followed by coevaporation with toluene (2×100 mL) to give the title compound.

EXAMPLE 83

$N^6$-Benzoyl-2'-O-(trans-2-methoxycyclohexyl) Adenosine

A solution of 2'-O-(trans-2-methoxy-cyclohexyl) adenosine (0.056 mol) in pyridine (100 mL) is evaporated under reduced pressure to dryness. The residue is redissolved in pyridine (560 mL) and cooled in an ice water bath. Trimethylsilyl chloride (36.4 mL, 0.291 mol) is added and the reaction is stirred at 5° C. for 30 minutes. Benzoyl chloride (33.6 mL, 0.291 mol) is added and the reaction is allowed to warm to 25° C. for 2 hours and then cooled to 5° C. The reaction is diluted with cold water (112 mL) and after stirring for 15 min, concentrated ammonium hydroxide (112 mL). After 30 min, the reaction is concentrated under reduced pressure (below 30° C.) followed by coevaporation with toluene (2×100 mL). The residue is dissolved in ethyl acetate-methanol (400 mL, 9:1) and the undesired silyl by-products are removed by filtration. The filtrate is concentrated under reduced pressure and purified by silica gel flash column chromatography (800 g, chloroform-methanol 9:1). Selected fractions are combined, concentrated under reduced pressure and dried at 25° C./0.2 mmHg for 2 h to give the title compound.

EXAMPLE 84

$N^6$-Benzoyl-5'-O-(dimethoxytrityl)-2'-O-(trans-2-methoxycyclohexyl) Adenosine

A solution of $N^6$-benzoyl-2'-O-(trans-2-methoxycyclohexyl) adenosine (0.285 mol) in pyridine (100 mL) is evaporated under reduced pressure to an oil. The residue is redissolved in dry pyridine (300 mL) and 4,4'-dimethoxytriphenylmethyl chloride (DMT-Cl, 10.9 g, 95%, 0.31 mol) added. The mixture is stirred at 25° C. for 16 h and then poured onto a solution of sodium bicarbonate (20 g) in ice water (500 mL). The product is extracted with ethyl acetate (2×150 mL). The organic layer is washed with brine (50 mL), dried over sodium sulfate (powdered) and evaporated under reduced pressure (below 40° C.). The residue is chromatographed on silica gel (400 g, ethyl acetate-hexane 1:1. Selected fractions were combined, concentrated under reduced pressure and dried at 25° C./0.2 mmHg to give the title compound.

EXAMPLE 85

[N6-Benzoyl-5'-O-(4,4'-dimethoxytrityl)-2'-O-(trans-2-methoxycyclohexyl) Adenosine-3'-O-yl]-N,N-diisopropylamino-cyanoethoxy Phosphoramidite Phosphitylation of $N^6$-benzoyl-5'-O-(dimethoxytrityl)-2'-O-(trans-2-methoxycyclohexyl) adenosine was performed as illustrated above to give the title compound.

EXAMPLE 86

General Procedures for Chimeric C3'-Endo and C2'-Endo Modified Oligonucleotide Synthesis Oligonucleotides are synthesized on a PerSeptive Biosystems Expedite 8901 Nucleic Acid Synthesis System. Multiple 1-mmol syntheses are performed for each oligonucleotide. The 3'-end nucleoside containing solid support is loaded into the column. Trityl groups are removed with trichloroacetic acid (975 mL over one minute) followed by an acetonitrile wash. The oligonucleotide is built using a modified diester (P=O) or thioate (P=S) protocol.

Phosphodiester Protocol

All standard amidites (0.1 M) are coupled over a 1.5 minute time frame, delivering 105 µL material. All novel amidites are dissolved in dry acetonitrile (100 mg of amidite/1 mL acetonitrile) to give approximately 0.08–0.1 M solutions. The 2'-modified amidites (both ribo and arabino monomers) are double coupled using 210 µL over a total of 5 minutes. Total coupling time is approximately 5 minutes (210 mL of amidite delivered). 1-H-tetrazole in acetonitrile is used as the activating agent. Excess amidite is washed away with acetonitrile. (1S)-(+)-(10-camphorsulfonyl) oxaziridine (CSO, 1.0 g CSO/8.72 mL dry acetonitrile) is used to oxidize (3 minute wait step) delivering approximately 375 µL of oxidizer. Standard amidites are delivered (210 µL) over a 3-minute period.

Phosphorothioate Protocol

The 2'-modified amidite is double coupled using 210 µL over a total of 5 minutes. The amount of oxidizer, 3H-1,2-benzodithiole-3-one-1,1-dioxide (Beaucage reagent, 3.4 g Beaucage reagent/200 mL acetonitrile), is 225 µL (one minute wait step). The unreacted nucleoside is capped with a 50:50 mixture of tetrahydrofuran/acetic anhydride and tetrahydrofuran/pyridine/1-methylimidazole. Trityl yields are followed by the trityl monitor during the duration of the synthesis. The final DMT group is left intact. After the synthesis, the contents of the synthesis cartridge (1 mmole) is transferred to a Pyrex vial and the oligonucleotide is cleaved from the controlled pore glass (CPG) using 30% ammonium hydroxide ($NH_4OH$, 5 mL) for approximately 16 hours at 55° C.

Oligonucleotide Purification

After the deprotection step, the samples are filtered from CPG using Gelman 0.45 µm nylon acrodisc syringe filters. Excess $NH_4OH$ is evaporated away in a Savant AS160 automatic speed vac. The crude yield is measured on a Hewlett Packard 8452A Diode Array Spectrophotometer at 260 nm. Crude samples are then analyzed by mass spectrometry (MS) on a Hewlett Packard electrospray mass spectrometer. Trityl-on oligonucleotides are purified by reverse phase preparative high performance liquid chromatography (HPLC). HPLC conditions are as follows: Waters 600E with 991 detector; Waters Delta Pak C4 column (7.8×300 mm); Solvent A: 50 mM triethylammonium acetate (TEA-Ac), pH 7.0; Solvent B: 100% acetonitrile; 2.5 mL/min flow rate; Gradient: 5% B for first five minutes with linear increase in B to 60% during the next 55 minutes. Fractions containing the desired product/s (retention time= 41 minutes for DMT-ON-16314; retention time=42.5 minutes for DMT-ON-16315) are collected and the solvent is dried off in the speed vac. Oligonucleotides are detritylated in 80% acetic acid for approximately 60 minutes and lyophilized again. Free trityl and excess salt are removed by passing detritylated oligonucleotides through Sephadex G-25 (size exclusion chromatography) and collecting appropriate samples through a Pharmacia fraction collector. The solvent is again evaporated away in a speed vac. Purified oligonucleotides are then analyzed for purity by CGE, HPLC (flow rate: 1.5 mL/min; Waters Delta Pak C4 column, 3.9×300 mm), and MS. The final yield is determined by spectrophotometer at 260 nm.

Procedures

Procedure 1

ICAM-1 Expression

Oligonucleotide Treatment of HUVECs

Cells were washed three times with Opti-MEM (Life Technologies, Inc.) prewarmed to 37° C. Oligonucleotides were premixed with 10 g/mL Lipofectin (Life Technologies, Inc.) in Opti-MEM, serially diluted to the desired concentrations, and applied to washed cells. Basal and untreated (no oligonucleotide) control cells were also treated with Lipofectin. Cells were incubated for 4 h at 37° C., at which time the medium was removed and replaced with standard growth medium with or without 5 mg/mL TNF-α 7 & D Systems). Incubation at 37° C. was continued until the indicated times.

Quantitation of ICAM-1 Protein Expression by Fluorescence-Activated Cell Sorter

Cells were removed from plate surfaces by brief trypsinization with 0.25% trypsin in PBS. Trypsin activity was quenched with a solution of 2% bovine serum albumin and 0.2% sodium azide in PBS (+Mg/Ca). Cells were pelleted by centrifugation (1000 rpm, Beckman GPR centrifuge), resuspended in PBS, and stained with 3 $1/10^5$ cells of the ICAM-1 specific antibody, CD54-PE (Pharmingin). Antibodies were incubated with the cells for 30 min at 4 C. in the dark, under gently agitation. Cells were washed by centrifugation procedures and then resuspended in 0.3 mL of FacsFlow buffer (Becton Dickinson) with 0.5% formaldehyde (Polysciences). Expression of cell surface ICAM-1 was then determined by flow cytometry using a Becton Dickinson FACScan. Percentage of the control ICAM-1 expression was calculated as follows: [(oligonucleotide-treated ICAM-1 value)–(basal ICAM-1 value)/(non-treated ICAM-1 value)–(basal ICAM-1 value)]. (Baker, Brenda, et. al. 2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells, *The Journal of Biological Chemistry*, 272, 11994–12000, 1997.)

ICAM-1 expression of chimeric C3'-endo and C2'-endo modified oligonucleotides of the invention is measured by the reduction of ICAM-1 levels in treated HUVEC cells. The oligonucleotides are believed to work by RNase H cleavage mechanism. Appropriate scrambled control oligonucleotides are used as controls. They have the same base composition as the test sequence.

Sequences that contain the chimeric C3'-endo (2'-MOE) and C2'-endo (one of the following modifications: 2'-S-Me, 2'-Me, 2'-ara-F, 2'-ara-OH, 2'-ara-O-Me) as listed in Table X below are prepared and tested in the above assay. SEQ ID NO: 24, a C-raf targeted oligonucleotide, is used as a control.

TABLE X

Oligonucleotides Containing chimeric 2'-O-(2-methoxyethyl) and 2'-S-(methyl) modifications.

| SEQ ID NO: | Sequence (5'-3') | Target |
|---|---|---|
| 24 | AsTsGs $C^m$sAsTs TsCs$^m$Ts GsCs$_m$ Cs$^m$Cs$^m$C$^m$sC$^m$s AsAsGs GsA | mouse C-raf |
| 25 | GsC$^m$sC$^m$s C$^m$sAsAs GsC$^m$sTs GsGsC$^m$s ASTsC$^m$S C$^m$sGSTs C$^m$SA | human ICAM-1 |

All nucleosides in bold are 2'-O-(methoxyethyl); subscript s indicates a phosphorothioate linkage; underlined nucleosides indicate 2'-S-Me- modification. Superscript m on C (Cm) indicates a 5-methyl-C.

TABLE XI

Oligonucleotides Containing chimeric 2'-O-(2-methoxyethyl) and 2'-O-(methyl) modifications

| SEQ ID NO: | Sequence (5'-3') | Target |
|---|---|---|
| 24 | AsTsGs $C^m$sAsTs TsCs$^m$Ts GsC$^m$Cs$^m$Cs$^m$C$^m$sC$^m$s AsAsGs GsA | mouse C-raf |
| 25 | GsC$^m$sC$^m$s C$^m$sAsAs GsC$^m$sTs GsGsC$^m$s ASTsC$^m$S C$^m$sGSTs C$^m$SA | human ICAM-1 |

All nucleosides in bold are 2'-O-(methoxyethyl); subscript s indicates a phosphorothioate linkage; underlined nucleosides indicate 2'-Methyl modification. Superscript m on C (Cm) indicates a 5-methyl-C.

TABLE XII

Oligonucleotides Containing chimeric 2'-O-(2-methoxyethyl) and 2'-ara-(fluoro) modifications

| SEQ ID NO: | Sequence (5'-3') | Target |
|---|---|---|
| 24 | AsTsGs $C^m$sAsTs TsCs$^m$Ts GsCs$^m$Cs$^m$Cs$^m$C$^m$sC$^m$s AsAsGs GsA | mouse C-raf |
| 25 | GsC$^m$sC$^m$s C$^m$sAsAs GsC$^m$sTs GsGsC$^m$s ASTsC$^m$S C$^m$sGSTs C$^m$SA -- | human ICAM-1 |

All nucleosides in bold are 2'-O-(methoxyethyl); subscript s indicates a phosphorothioate linkage; underlined nucleosides indicate 2'-ara-(fluoro) modification. superscript m on C (Cm) indicates a 5-methyl-C.

TABLE XIII

Oligonucleotides Containing chimeric 2'-O-(2-methoxyethyl) and 2'-ara-(OH) modifications

| SEQ ID NO: | Sequence (5'-3') | Target |
|---|---|---|
| 24 | AsTsGs $C^m$sAsTs TsCs$^m$Ts GsCs$^m$Cs$^m$Cs$^m$C$^m$sC$^m$s AsAsGs GsA | mouse C-raf |
| 25 | GsC$^m$sC$^m$s C$^m$sAsAs GsC$^m$sTs GsGsC$^m$s ASTsC$^m$S C$^m$sGSTs C$^m$SA | human ICAM-1 |

All nucleosides in bold are 2=-O-(methoxyethyl); subscript s indicates a phosphorothioate linkage; underlined nucleosides indicate 2'-ara-(OH) modification. superscript m on C (Cm) indicates a 5-methyl-C.

TABLE XIV

Oligonucleotides Containing chimeric 2'-O-(2-methoxyethyl) and 2'-ara-(OMe) modifications

| SEQ ID NO: | Sequence (5'-3') | Target |
|---|---|---|
| 24 | AsTsGs $C^m$sAsTs TsCs$^m$Ts GsCs$^m$Cs$^m$Cs$^m$C$^m$sC$^m$s AsAsGs GsA | mouse C-raf |
| 25 | GsC$^m$sC$^m$s C$^m$sAsAs GsC$^m$sTs GsGsC$^m$s ASTsC$^m$S C$^m$sGSTs C$^m$SA-3' | human ICAM-1 |

All nucleosides in bold are 2=-O-(methoxyethyl); subscript S indicates a phosphorothioate linkage; underlined nucleosides indicate 2'-ara-(OMe) modification. superscript m on C ($C^m$) indicates a 5-methyl-C.

Procedure 2

Enzymatic Degradation of 2'-O-Modified Oligonucleotides

Three oligonucleotides are synthesized incorporating the modifications shown in Table 2 below at the 3'-end. These modified oligonucleotides are subjected to snake venom phosphodiesterase action.

Oligonucleotides (30 nanomoles) are dissolved in 20 mL of buffer containing 50 mM Tris-HCl pH 8.5, 14 mM MgCl$_2$, and 72 mM NaCl. To this solution 0.1 units of snake-venom phosphodiesterase (Pharmacia, Piscataway, N.J.), 23 units of nuclease P1 (Gibco LBRL, Gaithersberg, Md.), and 24 units of calf intestinal phosphatase (Boehringer Mannheim, Indianapolis, Ind.) are added and the reaction mixture is incubated at 37 C. for 100 hours. HPLC analysis is carried out using a Waters model 715 automatic injector, model 600E pump, model 991 detector, and an Alltech (Alltech Associates, Inc., Deerfield, Ill.) nucleoside/nucleotide column (4.6×250 mm). All analyses are performed at room temperature. The solvents used are A: water and B: acetonitrile. Analysis of the nucleoside composition is accomplished with the following gradient: 0–5 min., 2% B (isocratic); 5–20 min., 2% B to 10% B (linear); 20–40 min., 10% B to 50% B. The integrated area per nanomole is determined using nucleoside standards. Relative nucleoside ratios are calculated by converting integrated areas to molar values and comparing all values to thymidine, which is set at its expected value for each oligomer.

TABLE XV

Relative Nuclease Resistance of 2'-Modified Chimeric Oligonucleotides

5'-TTT TTT TTT TTT TTT T*T*T*T*-3' SEQ ID NO: 26
(Uniform phosphodiester)

T* = 2'-modified T
—S—Me
—Me
-2'-ara-(F)
-2'-ara-(OH)
-2'-ara-(OMe)

Procedure 3

General Procedure for the Evaluation of Chimeric C3'-Endo and C2'-Endo Modified Oligonucleotides Targeted to Ha-ras Different types of human tumors, including sarcomas, neuroblastomas, leukemias and lymphomas, contain active oncogenes of the ras gene family. Ha-ras is a family of small molecular weight GTPases whose function is to regulate cellular proliferation and differentiation by transmitting signals resulting in constitutive activation of ras are associated with a high percentage of diverse human cancers. Thus, ras represents an attractive target for anticancer therapeutic strategies.

SEQ ID NO: 27 (5'-TsCsCs GsTsCs AsTsCs GsCsTs CsCsTs CsAsGs GsG-3') is a 20-base phosphorothioate oligodeoxynucleotide targeting the initiation of translation region of human Ha-ras and it is a potent isotype-specific inhibitor of Ha-ras in cell culture based on screening assays ($IC_{50}$=45 nm). Treatment of cells in vitro with SEQ ID NO: 27 results in a rapid reduction of Ha-ras mRNA and protein synthesis and inhibition of proliferation of cells containing an activating Ha-ras mutation. When administered at doses of 25 mg/kg or lower by daily intraperitoneal injection (IP), SEQ ID NO: 27 exhibits potent antitumor activity in a variety of tumor xenograft models, whereas mismatch controls do not display antitumor activity. SEQ ID NO: 27 has been shown to be active against a variety of tumor types, including lung, breast, bladder, and pancreas in mouse xenograft studies (Cowsert, L. M. *Anti-cancer drug design*, 1997, 12, 359–371). A second-generation analog of SEQ ID NO: 27, where the 5' and 3' termini ("wings") of the sequence are modified with 2'-methoxyethyl (MOE) modification and the backbone is kept as phosphorothioate (Table XVI, SEQ ID NO: 27 (5'-TsCsCs GsTsCs AsTsCs GsCsTs CsCsTs CsAsGs GsG-3')), exhibits $IC_{50}$ of 15 nm in cell culture assays, thus, a 3-fold improvement in efficacy is observed from this chimeric analog. Because of the improved nuclease resistance of the 2'-MOE phosphorothioate, SEQ ID NO: 27 (5'-TsCsCs GsTsCs AsTsCs GsCsTs CsCsTs CsAsGs GsG-3') increases the duration of antisense effect in vitro. This will relate to frequency of administration of this drug to cancer patients. SEQ ID NO: 27 (5'-TsCsCs GsTsCs AsTsCsGsCsTs CsCsTs CsAsGs GsG-3') is currently under evaluation in ras dependent tumor models (Cowsert, L. M. *Anti-cancer drug design*, 1997, 12, 359–371). The parent compound, SEQ ID NO: 27, is in Phase I clinical trials against solid tumors by systemic infusion.

Antisense oligonucleotides having the 2'-Me modification are prepared and tested in the aforementioned assays in the manner described to determine activity.

Ha-ras Antisense Oligonucleotides with chimeric C3'-endo and C2'-endo modifications and Their Controls.

TABLE XVI

Ha-ras Antisense Oligonucleotides With chimeric C3'-endo and C2'-endo modifications and Their Controls.

| SEQ ID NO: | Sequence | Backbone | 2'-Modif. | Comments |
|---|---|---|---|---|
| 27 | 5'-TsCsCs GsTsCs AsTsCs GsCsTs CsCsTs CsAsGs GsG-3' | P=S | 2'-H | parent |
| 28 | 5'-TsCsAs GsTsAs AsTsAs GsGsCs CsCsAs CsAsTs GsG-3' | P=S | 2'-H | mismatch control |
| 29 | 5'-ToToCo GsTsCs AsTsCs GsCsTs CoCoTo CoAoGo GoG-3' | P=O/ P=S/ P=O | 2'-O-Moe in wings | Parent Gapmer (Mixed Backbone) |

TABLE XVI-continued

Ha-ras Antisense Oligonucleotides With chimeric C3'-endo and C2'-endo modifications and Their Controls.

| SEQ ID NO: | Sequence | Backbone | 2'-Modif. | Comments |
|---|---|---|---|---|
| 27 | 5'-TsCsCs GsTsCs AsTsCs GsCsTs CsCsTs CsAsGs GsG-3' | P=S | 2'-O-MOE in wings | Parent Gapmer as uniform thioate |
| 29 | 5'-ToCoAo GsTsAs AsTsAs GsCsCs GsCsCs GsCoCo CoCoAo CoAoTo GoG-3' | P=O/ P=S/ P=O | 2'-O-MOE in wings | Parent Gapmer (mixed Backbone) |
| 28 | 5'-TsCsAs GsTsAs AsTs As GsCsCs GsCsCs CsCsAs CsAsTs GsC-3' | P=S | 2'-O-MOE in wings | Control Gapmer as uniform Thioate |
| 27 | 5'-TsCsCs GsTsCs AsTsCs GsCsTs CsCsTs CsAsGs GsG-3' | P=S | 2'-O-MOE in wings | Control Gapmer with MOE control |
| 28 | 5'-TsCsAs GsTsAs AsTsAs GsCsCs GsCsCs CsCsAs CsAsTs GsC-3' | P=S | 2'-O-MOE in wings | Control Gapmer with MOE Control |

All underlined portions of sequences are 2'-Me.

Procedure 7

In Vivo Nuclease Resistance

The in vivo Nuclease Resistance of chimeric C3'-endo and C2'-endo modified oligonucleotides is studied in mouse plasma and tissues (kidney and liver). For this purpose, the C-raf oligonucleotide series SEQ ID NO: 30 are used and the following five oligonucleotides listed in the Table below will be evaluated for their relative nuclease resistance.

TABLE XVII

Study of in vivo Nuclease Resistance of chimeric C3'- endo (2'-O-MOE) and C2'-endo (2'S—Me) modified oligonucleotides with and without nuclease resistant caps (2'-5'-phosphate or phosphorothioate linkage with 3'-O-MOE in cap ends).

| SEQ ID NO: | Sequence | Backbone | Description |
|---|---|---|---|
| 30 | 5'-ATG CAT TCT GCC CCA AGGA-3' | P=S, 2'-H | (control) rodent C-raf antisense oligo |
| 31 | AoToGo CoAsTs TsCsTs GsCsCs CsCsAo AoGoGo A | P=O/ P=S/ P=O | 2'-MOE/2'S—Me/ 2'-MOE |
| 32 | AsTsGs CsAsTs TsCsTs GsCsCs CsCsAs AsGsGs A | P=S | 2'-MOE/2'-S—Me/ 2'-MOE |
| 33 | Ao*ToGo CoAsTs TsCsTs GsCsCs CsCsAo AoGoGo *A | P=O/ P=S/ P=O | In asterisk, 2'-5' linkage with 3'-O-MOE; 2'-O-MOE/2'-S—Me/2'-O-MOE/2'-5' linkage with 3'-O-MOE in asterisk; |
| 34 | As*TsGs CsAsTs TsCsTs GsCsCs CsCsAs AsGsGs *A | P=S | In asterisk, 2'-5' linkage with 3'-O-MOE; 2'-O-MOE/ 2'-S—Me/2'-O-MOE/2'-5' linkage with 3'-O-MOE in asterisk. |

TABLE XVIII

Study of in vivo Nuclease Resistance of chimeric C3'-endo (2'-O-MOE) and C2'-endo (2'-Me) modified oligonucleotides with and without nuclease resistant caps (2'-5'-phosphate or phosphorothioate linkage with 3'-O-MOE in cap ends).

| SEQ ID NO: | Sequence | Backbone | Description |
|---|---|---|---|
| 30 | 5'-ATG CAT TCT GCC CCA AGGA-3' | P=S, 2'-H | (control) rodent C-raf antisense oligo |
| 31 | AoToGo CoAsTs TsCsTs GsCsCs CsCsAo AoGoGo A' | P=O/ P=S/ P=O | 2'-MOE/2'-Me/ 2'-MOE |
| 32 | AsTsGs CsAsTs TsCsTs GsCsCs CsCsAs AsGsGs A | P=S | 2'-MOE/2'-Me/ 2'-MOE |
| 33 | Ao*ToGo CoAsTs TsCsTs GsCsCs CsCsAo AoGoGo *A | P=O/ P=S/ P=O | In asterisk, 2'-5' linkage with 3'-O-MOE; 2'-O-MOE/ 2'-Me/2'-O-MOE/2'-5' linkage with 3'-O-MOE in asterisk; |
| 34 | As*TsGs CsAsTs TsCsTs GsCsCs CsCsAs AsGsGs *A | P=S | In asterisk, 2'-5' linkage with 3'-O-MOE; 2'-O-MOE/ 2'-Me/2'-O-MOE/2'-5' linkage with 3'-O-MOE in asterisk; |

TABLE XIX

Study of in vivo Nuclease Resistance of chimeric C3'-endo (2'-O-MOE) and C2'-endo (2'-ara-F) modified oligonucleotides with and without nuclease resistant caps (2'-5'-phosphate or phosphorothioate linkage with 3'-O-MOE in cap ends).

| SEQ ID NO: | Sequence | Backbone | Description |
|---|---|---|---|
| 30 | 5'-ATG CAT TCT GCC CCA AGGA-3' | P=S, 2'-H | (control) rodent C-raf antisense oligo |
| 31 | AoToGo CoAsTs TsCsTs GsCsCs CsCsAo AoGoGo A | P=O/ P=S/ P=O | 2'-MOE/2'-ara-F/ 2'-MOE |
| 32 | AsTsGs CsAsTs TsCsTs CsCsAs GsCsCs AsGsGs A | P=S | 2'-MOE/2'-ara-F/2'-MOE |
| 33 | Ao*ToGo CoAsTs TsCsTs GsCsCs CsCsAo AoGoGo *A | P=O/ P=S/ P=O | In asterisk, 2'-5' linkage with 3'-O-MOE; 2'-O-MOE/ 2'-ara-F/2'-O-MOE/2'-5' linkage with 3'-O-MOE in asterisk; |
| 34 | As*TsGs CsAsTs TsCsTs GsCsCs CsCsAs AsGsGs *A | P=S | In asterisk, 2'-5' linkage with 3'-O-MOE; 2'-o-MO 2'-ara-F/2'-O-MOE/2'-5' linkage with 3'-O-MOE in asterisk; |

TABLE XX

Study of in vivo Nuclease Resistance of chimeric C3'-endo (2'-O-MOE) and C2'-endo (2'-ara-OH) modified oligonuclcotides with and without nuclease resistant caps (2'-5'-phosphate or phosphorothioate linkage with 3'-O-MOE in cap ends).

| SEQ ID NO: | Sequence | Backbone | Description |
|---|---|---|---|
| 30 | 5'-ATG CAT TCT GCC CCA AGGA-3' | P=S, 2'-H | (control) rodent C-raf antisense oligo |
| 31 | AoToGo CoAsTs TsCsTs GsCsCs CsCsAo AoGoGo A | P=O/ P=S/ P=O | 2'-MOE/2'-ara-OH/ 2'-MOE |
| 32 | AsTsGs CsAsTs TsCsTs GsCsCs CsCsAs AsGsGs A | P=S | 2'-MOE/2'-ara-OH/ 2'-MOE |
| 33 | Ao*ToGo CoAsTs TsCsTs GsCsCs CsCsAo AoGoGo *A | P=O/ P=S/ P=O | In asterisk, 2'-5' linkage with 3'-O-MOE; 2'-O-MOE/2'-ara-OH/ 2'-O-MOE/2'-5' linkage with 3'-O-MOE in asterisk; |
| 34 | As*TsGs CsAsTs TsCsTs GsCsCs CsCsAs AsGsGs *A | P=S | In asterisk, 2'-5' linkage with 3'-O-MOE; 2'-O-MOE/2'-ara-OH/2'-O-MOE/2'-5' linkage with 3'-O-MOE in asterisk; |

TABLE XXI

Study of in vivo Nuclease Resistance of chimeric C3'-endo (2'-O-MOE) and C2'-endo (2'-ara-OMe) modified oligonuclcotides with and without nuclease resistant caps (2'-5'-phosphate or phosphorothioate linkage with 3'-O-MOE in cap ends).

| SEQ ID NO: | Sequence | Backbone | Description |
|---|---|---|---|
| 30 | 5'-ATG CAT TCT GCC CCA AGGA-3' | P=S, 2'-H | (control) rodent C-raf antisense oligo |
| 31 | AoToGo CoAsTs TsCsTs GsCsCs CsCsAo AoGoGo Aa | P=O/ P=S/ P=O | 2'-MOE/2'-ara-OMe/ 2'-MOE |
| 32 | AsTsGs CsAsTs TsCsTs GsCsCs CsCsAs AsGsGs A | P=S | 2'-MOE/2'-ara-OMe/ 2'-MOE |
| 33 | Ao*ToGo CoAsTs TsCsTs GsCsCs CsCsAo AoGoGo *A | P=O/ P=S/ P=O | In asterisk, 2'-5' linkage with 3'-O-MOE; 2'-O-MOE/2'-ara-OMe/ 2'-O-MOE/2'-5' linkage with 3'-O-MOE in asterisk; |
| 34 | As*TsGs CsAsTs TsCsTs GsCsCs CsCsAs AsGsGs *A | P=S | In asterisk, 2'-5' linkage with 3'-O-MOE; 2'-O-MOE/2'-ara-OMe/2'-O-MOE/2'-5' linkage with 3'-O-MOE in asterisk; |

Procedure 8

Animal Studies for In Vivo Nuclease Resistance

For each oligonucleotide to be studied, 9 male BALB/c mice (Charles River, Wilmington, Mass.), weighing about 25 g are used (Crooke et al., *J. Pharmacol. Exp. Ther.*, 1996, 277, 923). Following a 1-week acclimation, the mice receive a single tail vein injection of oligonucleotide (5 mg/kg) administered in phosphate buffered saline (PBS), pH 7.0.

The final concentration of oligonucleotide in the dosing solution is (5 mg/kg) for the PBS formulations. One retro-orbital bleed (either 0.25, 9.05, 2 or 4 post dose) and a terminal bleed (either 1, 3, 8 or 24 h post dose) is collected from each group. The terminal bleed (approximately 0.6–0.8 mL) is collected by cardiac puncture following ketamine/xylazine anesthesia. The blood is transferred to an EDTA-coated collection tube and centrifuged to obtain plasma. At termination, the liver and kidneys will be collected from each mouse. Plasma and tissues homogenates will be used for analysis for determination of intact oligonucleotide content by CGE. All samples are immediately frozen on dry ice after collection and stored at −80° C. until analysis.

Procedure 9

RNase H Studies with Chimeric C3'-Endo and C2'-Endo Modified Oligonucleotides With and Without Nuclease Resistant Caps $^{32}$P Labeling of Oligonucleotides The oligoribonucleotide (sense strand) was 5'-end labeled with $^{32}$P using [$^{32}$P]ATP, T4 polynucleotide kinase, and standard procedures (Ausubel, F. M., Brent, R., Kingston, R. E., Moore, D. D., Seidman, J. G., Smith, J. A., and Struhl, K., in *Current Protocols in Molecular Biology*, John Wiley, New York (1989)). The labeled RNA was purified by electrophoresis on 12% denaturing PAGE (Sambrook, J., Frisch, E. F., and Maniatis, T., *Molecular Cloning: A Laboratory Manual*, Cold Spring Harbor Laboratory Press, Plainview (1989)). The specific activity of the labeled oligonucleotide was approximately 6000 cpm/fmol.

Determination of RNase H Cleavage Patterns

Hybridization reactions were prepared in 120 μL of reaction buffer [20 mM Tris-HC (pH 7.5), 20 mM KCl, 10 mM $MgCl_2$, 0.1 mM DTT] containing 750 nM antisense oligonucleotide, 500 nM sense oligoribonucleotide, and 100,000 cpm $^{32}$P-labeled sense oligoribonucleotide. Reactions were heated at 90° C. for 5 min and 1 unit of Inhibit-ACE was added. Samples were incubated overnight at 37° C. degrees. Hybridization reactions were incubated at 37° C. with $1.5 \times 10.8^{-8}$ mg of *E. coli* RNase H enzyme for initial rate determinations and then quenched at specific time points. Samples were analyzed by trichloroacetic acid (TCA) assay or by denaturing polyacrylamide gel electrophoresis as previously described [Crooke, S. T., Lemonidis, K. M., Neilson, L., Griffey, R., Lesnik, E. A., and Monia, B. P., Kinetic characteristics of *Escherichia coli* RNase H1: cleavage of various antisense oligonucleotide-RNA duplexes, *Biochem J*, 312, 599 (1995); Lima, W.F. and Crooke, S. T., Biochemistry 36, 390–398, 1997].

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. An oligonucleotide comprising:
at least one continuous sequence of nucleotides having A-form conformational geometry; and
at least one continuous sequence of nucleotides having B-form conformational geometry;
wherein at least one of said nucleotides having B-form conformational geometry is an arabinonucleotide.

2. The oligonucleotide of claim 1 further comprising at least one nucleotide having A-form conformational geometry bound by an internucleotide linkage to a 3' position of at least one of said sequence of nucleotides having B-form conformational geometry.

3. The oligonucleotide of claim 2 wherein said internucleotide linkage at the 3' end of said oligonucleotide is a 3'–5' phosphodiester, 2'–5' phosphodiester, phosphorothioate, Sp phosphorothioate, Rp phosphorothioate, phosphorodithioate, 3'-deoxy-3'-amino phosphoroamidate, 3'-methylenephosphonate, methylene(methylimino), dimethylhydrazino, amide 3, amide 4 or a boranophosphate.

4. The oligonucleotide of claim 3 wherein said internucleotide linkage is a 2'–5' phosphodiester, 3'-methylenephosphonate, Sp phosphorothioate or a methylene(methylimino).

5. The oligonucleotide of claim 2 further comprising at least two nucleotides having A-form conformational geometry bound by an internucleotide linkage to a 3' position of at least one of said sequence of nucleotides having B-form conformational geometry.

6. The oligonucleotide of claim 2 wherein at least two of said nucleotides having B-form conformational geometry are joined together by phosphate, phosphorothioate, phosphorodithioate or boranophosphate internucleotide linkages.

7. The oligonucleotide of claim 2 wherein at least one of said nucleotides having A-form conformational geometry is a 2'-fluoro nucleotide or a nucleotide having a 2'-substituent having the formula I or II:

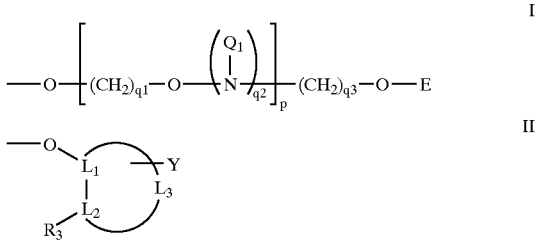

wherein
E is $C_1$–$C_{10}$ alkyl, $N(Q_1)(Q_2)$ or $N=C(Q_1)(Q_2)$;
each $Q_1$ and $Q_2$ is, independently, H, $C_1$–$C_{10}$ alkyl, dialkylaminoalkyl, a nitrogen protecting group, a tethered or untethered conjugate group, a linker to a solid support, or $Q_1$ and $Q_2$, together, are joined in a nitrogen protecting group or a ring structure optionally containing at least one additional heteroatom selected from N and O;
$R_3$ is OX, SX, or $N(X)_2$;
each X is, independently, H, $C_1$–$C_8$ alkyl, $C_1$–$C_8$ haloalkyl, $C(=NH)N(H)Z$, $C(=O)N(H)Z$ or $OC(=O)N(H)Z$;
Z is H or $C_1$–$C_8$ alkyl;
$L_1$, $L_2$ and $L_3$ form a ring system having from about 4 to about 7 carbon atoms or having from about 3 to about 6 carbon atoms and 1 or 2 heteroatoms selected from oxygen, nitrogen and sulfur and wherein said ring system is aliphatic, unsaturated aliphatic, aromatic, or saturated or unsaturated heterocyclic;
Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $O(Q_1)$, halo, $S(Q_1)$, or CN;
each q1 is, independently, from 2 to 10;
each q2 is, independently, 0 or 1;
m is 0, 1 or 2;
p is from 0 to 10; and
q3 is from 1 to 10 with the proviso that when p is 0, q3 is greater than 1.

8. The oligonucleotide of claim 7 wherein at least one nucleotide having A-form conformational geometry has the 2'-substituent group of formula I and p is 0.

9. The oligonucleotide of claim 2 wherein at least one of said nucleotides having A-form conformational geometry is a 2'-F ribonucleotide, a 2'-O—($C_1$–$C_6$ alkyl) ribonucleotide, or a 2'-O—($C_1$–$C_6$ substituted alkyl) ribonucleotide wherein the substitution is $C_1$–$C_6$ ether, $C_1$–$C_6$ thioether, amino, amino($C_1$–$C_6$ alkyl) or amino($C_1$–$C_6$ alkyl)$_2$.

10. The oligonucleotide of claim 2 wherein at least one of said nucleotides having B-form conformational geometry is a 2'-CN arabinonucleotide, a 2'-F arabinonucleotide, a 2'-Cl arabinonucleotide, a 2'-Br arabinonucleotide, a 2'-$N_3$ arabinonucleotide, a 2'-OH arabinonucleotide, a 2'-O—$CH_3$ arabinonucleotide or a 2'-dehydro-2'-$CH_3$ arabinonucleotide.

11. The oligonucleotide of claim 10 wherein at least one of said nucleotides having B-form conformational geometry is a 2'-F arabinonucleotide, a 2'-OH arabinonucleotide or a 2'-O—$CH_3$ arabinonucleotide.

12. The oligonucleotide of claim 11 wherein at least one of said nucleotides having B-form conformational geometry is a 2'-F arabinonucleotide or a 2'-OH arabinonucleotide.

13. The oligonucleotide of claim 12 wherein at least one of said nucleotides having B-form conformational geometry is a 2'-F arabinonucleotide.

14. The oligonucleotide of claim 2 wherein at least one of said nucleotides having B-form conformational geometry is a 2'-CN arabinonucleotide, a 2'-F arabinonucleotide, a 2'-Cl arabinonucleotide, a 2'-Br arabinonucleotide, a 2'-$N_3$ arabinonucleotide, a 2'-OH arabino-nucleotide, a 2'-O—$CH_3$ arabinonucleotide or a 2'-dehydro-2'-$CH_3$ arabinonucleotide; and
at least one of said nucleotides having A-form conformational geometry is a 2'-F ribonucleotide, a 2'-O—($C_1$–$C_6$ alkyl) ribonucleotide, or a 2'-O—($C_1$–$C_6$ substituted alkyl) ribonucleotide wherein the substitution is $C_1$–$C_6$ ether, $C_1$–$C_6$ thioether, amino, amino($C_1$–$C_6$ alkyl) or amino($C_1$–$C_6$ alkyl)$_2$.

15. The oligonucleotide of claim 14 wherein at least one of said nucleotides having B-form conformational geometry is a 2'-F arabinonucleotide or a 2'-OH arabinonucleotide; and
at least one of said nucleotides having A-form conformational geometry is a 2'-O—($C_1$–$C_6$ substituted alkyl) ribonucleotide wherein the substitution is $C_1$–$C_6$ ether, $C_1$–$C_6$ thioether, amino, amino($C_1$–$C_6$ alkyl) or amino($C_1$–$C_6$ alkyl)$_2$.

16. The oligonucleotide of claim 15 wherein at least one of said nucleotides having A-form conformational geometry is a 2'-alkylamino substituted nucleotide.

17. The oligonucleotide of claim 1 further comprising at least one nucleotide having A-form conformational geometry bound by an internucleotide linkage to a 5' position of at least one of said sequence of nucleotides having B-form conformational geometry.

18. The oligonucleotide of claim 17 wherein said internucleotide linkage at the 5' end of said oligonucleotide is a 3'–5' phosphodiester, 2'–5' phosphodiester, phosphorothioate, Sp phosphorothioate, Rp phosphorothioate, phosphorodithioate, 3'-deoxy-3'-amino, phosphoroamidate, 3'-methylenephosphonate, methylene (methylimino), dimethylhydrazino, amide 3, amide 4 or a boranophosphate.

19. The oligonucleotide of claim 18 wherein said internucleotide linkage is a 2'–5' phosphodiester, 3'-methylenephosphonate, Sp phosphorothioate or a methylene(methylimino) linkage.

20. The oligonucleotide of claim 17 further comprising at least two nucleotides having A-form conformational geometry bound by an internucleotide linkage to a 5' position of at least one of said sequence of nucleotides having B-form conformational geometry.

21. The oligonucleotide of claim 17 wherein at least two of said nucleotides having B-form conformational geometry are joined together by phosphate, phosphorothioate, phosphorodithioate or boranophosphate internucleotide linkages.

22. The oligonucleotide of claim 17 wherein at least one of said nucleotides having
A-form conformational geometry is a 2'-fluoro nucleotide or a nucleotide having a 2'-substituent having the formula I or II:

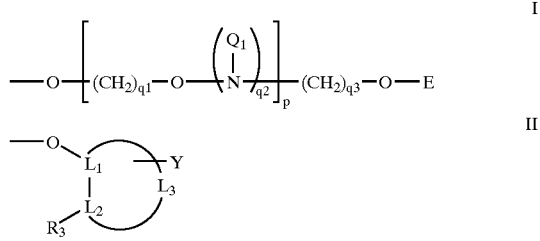

wherein
E is $C_1$–$C_{10}$ alkyl, $N(Q_1)(Q_2)$ or $N=C(Q_1)(Q_2)$;
each $Q_1$ and $Q_2$ is, independently, H, $C_1$–$C_{10}$ alkyl, dialkylaminoalkyl, a nitrogen protecting group, a tethered or untethered conjugate group, a linker to a solid support, or $Q_1$ and $Q_2$, together, are joined in a nitrogen protecting group or a ring structure optionally containing at least one additional heteroatom selected from N and O;

$R_3$ is OX, SX, or $N(X)_2$;

each X is, independently, H, $C_1$–$C_8$ alkyl, $C_1$–$C_8$ haloalkyl, C(=NH)N(H)Z, C(=O)N(H)Z or OC(=O)N(H)Z;

Z is H or $C_1$–$C_8$ alkyl;

$L_1$, $L_2$ and $L_3$ form a ring system having from about 4 to about 7 carbon atoms or having from about 3 to about 6 carbon atoms and 1 or 2 heteroatoms selected from oxygen, nitrogen and sulfur and wherein said ring system is aliphatic, unsaturated aliphatic, aromatic, or saturated or unsaturated heterocyclic;

Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $O(Q_1)$, halo, $S(Q_1)$, or CN;

each q1 is, independently, from 2 to 10;

each q2 is, independently, 0 or 1;

m is 0, 1 or 2;

p is from 0 to 10; and q3 is from 1 to 10 with the proviso that when p is 0, q3 is greater than 1.

23. The oligonucleotide of claim 22 wherein at least one nucleotide having A-form conformational geometry has the 2'-substituent group of formula I and p is 0.

24. The oligonucleotide of claim 17 wherein at least one of said nucleotides having A-form conformational geometry is a 2'-F ribonucleotide, a 2'-O—($C_1$–$C_6$ alkyl) ribonucleotide, or a 2'-O—($C_1$–$C_6$ substituted alkyl) ribonucleotide wherein the substitution is $C_1$–$C_6$ ether, $C_1$–$C_6$ thioether, amino, amino($C_1$–$C_6$ alkyl) or amino($C_1$–$C_6$ alkyl)$_2$.

25. The oligonucleotide of claim 17 wherein at least one of said nucleotides having B-form conformational geometry is a 2'-CN arabinonucleotide, a 2'-F arabinonucleotide, a 2'-Cl arabinonucleotide, a 2'-Br arabinonucleotide, a 2'-$N_3$ arabinonucleotide, a 2'-OH arabinonucleotide, a 2'-O—$CH_3$ arabinonucleotide or a 2'-dehydro-2'-$CH_3$ arabinonucleotide.

26. The oligonucleotide of claim 25 wherein at least one of said nucleotides having B-form conformational geometry is a 2'-F arabinonucleotide, a 2'-OH arabinonucleotide or a 2'-O—$CH_3$ arabinonucleotide.

27. The oligonucleotide of claim 26 wherein at least one of said nucleotides having B-form conformational geometry is a 2'-F arabinonucleotide or a 2'-OH arabinonucleotide.

28. The oligonucleotide of claim 27 wherein at least one of said nucleotides having B-form conformational geometry is a 2'-F arabinonucleotide.

29. The oligonucleotide of claim 17 wherein at least one of said nucleotides having B-form conformational geometry is a 2'-CN arabinonucleotide, a 2'-F arabinonucleotide, a 2'-Cl arabinonucleotide, a 2'-Br arabinonucleotide, a 2'-$N_3$ arabinonucleotide, a 2'-OH arabinonucleotide, a 2'-O—$CH_3$ arabinonucleotide or a 2'-dehydro-2'-$CH_3$ arabinonucleotide; and at least one of said nucleotides having A-form conformational geometry is a 2'-F ribonucleotide, a 2'-O—($C_1$–$C_6$ alkyl) ribonucleotide, or a 2'-O—($C_1$–$C_6$ substituted alkyl) ribonucleotide wherein the substitution is $C_1$–$C_6$ ether, $C_1$–$C_6$ thioether, amino, amino($C_1$–$C_6$ alkyl) or amino($C_1$–$C_6$ alkyl)$_2$.

30. The oligonucleotide of claim 29 wherein at least one of said nucleotides having B-form conformational geometry is a 2'-F arabinonucleotide or a 2'-OH arabinonucleotide; and at least one of said nucleotides having A-form conformational geometry is a 2'-O—($C_1$–$C_6$ substituted alkyl) ribonucleotide wherein the substitution is $C_1$–$C_6$ ether, $C_1$–$C_6$ thioether, amino, amino($C_1$–$C_6$ alkyl) or amino($C_1$–$C_6$ alkyl)$_2$.

31. The oligonucleotide of claim 30 wherein at least one of said nucleotides having A-form conformational geometry is a 2'-alkylamino substituted nucleotide.

32. The oligonucleotide of claim 1 further comprising at least one nucleotide having B-form conformational geometry bound by an internucleotide linkage to a 3' or a 5' position of at least one of said sequence of nucleotides having A-form conformational geometry.

33. The oligonucleotide of claim 32 wherein said nucleotide having B-form conformational geometry is bound to said oligonucleotide by a 3'–5' phosphodiester, 2'–5' phosphodiester, phosphorothioate, Sp phosphorothioate, Rp phosphorothioate, phosphorodithioate, 3'-deoxy-3'-amino phosphoroamidate, 3'-methylenephosphonate, methylene (methylimino), dimethylhydrazino, amide 3, amide 4 or a boranophosphate internucleotide linkage.

34. The oligonucleotide of claim 33 wherein said internucleotide linkage is a 2'–5' phosphodiester, 3'-methylenephosphonate, Sp phosphorothioate or a methylene(methylimino).

35. The oligonucleotide of claim 1 wherein at least one nucleotide of said sequence of nucleotides has a C3' endo type pucker; and at least one of said nucleotides has a C2' endo type pucker or an O4' endo type pucker, provided that said nucleotides are not 2'-deoxy-erythro-pentofuranosyl nucleotides.

36. The oligonucleotide of claim 35 wherein at least one of said nucleotides having said C3' endo type pucker is bound to a 3' position to at least one of said nucleotides having said C2' endo type pucker or O4' endo type pucker.

37. The oligonucleotide of claim 35 wherein at least one of said nucleotides having said C3' endo type pucker is bound to a 5' position to at least one of said nucleotides having said C2' endo type pucker or O4' endo type pucker.

38. The oligonucleotide of claim 35 wherein at least one of said nucleotides having said C3' endo type pucker is bound to a 3' position to at least one of said nucleotides having said C2' endo type pucker or O4' endo type pucker; and at least one of said nucleotides having said C3' endo type pucker is bound to a 5' position to at least one of said nucleotides having said C2' endo type pucker or O4' endo type pucker.

* * * * *

UNITED STATES PATENT AND TRADEMARK OFFICE
CERTIFICATE OF CORRECTION

PATENT NO. : 6,737,520 B1  
DATED : May 18, 2004  
INVENTOR(S) : Muthiah Manoharan et al.

Page 1 of 1

It is certified that error appears in the above-identified patent and that said Letters Patent is hereby corrected as shown below:

<u>Title page,</u>  
Item [56], References Cited, OTHER PUBLICATIONS,  
"Abe" reference, delete "CH3O[(CH2)]yOxCH3" and insert  
-- CH3O[(CH2)]yO]xCH3 --; and  
"Altmann" reference, delete "2'-Ethylene" and insert -- 2'-O-Ethylene --;

<u>Column 93,</u>  
Line 63, delete "arabino-nucleotide" and insert -- arabinonucleotide --.

Signed and Sealed this

Twenty-eighth Day of March, 2006

JON W. DUDAS  
*Director of the United States Patent and Trademark Office*

SEQUENCE LISTING

<160> NUMBER OF SEQ ID NOS: 34

<210> SEQ ID NO 1
<211> LENGTH: 12
<212> TYPE: RNA
<213> ORGANISM: Artificial Sequence
<220> FEATURE:
<221> NAME/KEY: misc_feature
<223> OTHER INFORMATION: Oligonucleotide

<400> SEQUENCE: 1
cgcgaauucg cg                                                            12

<210> SEQ ID NO 2
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 2
tccgtcatcg ctcctcaggg                                                    20

<210> SEQ ID NO 3
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 3
ttagtaatag ccccacatgg                                                    20

```
<210> SEQ ID NO 4
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (20)..(20)
<223> OTHER INFORMATION: 3'- O-MOE linkage

<400> SEQUENCE: 4
atgcattctg cccccaagga                                              20

<210> SEQ ID NO 5
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (19)..(20)
<223> OTHER INFORMATION: 3'- O-MOE linkage

<400> SEQUENCE: 5
atgcattctg cccccaagga                                              20

<210> SEQ ID NO 6
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (18)..(19)
<223> OTHER INFORMATION: sub O linkage
<220> FEATURE:
<221> NAME/KEY: misc_feature
<222> LOCATION: (19)..(20)
<223> OTHER INFORMATION: 3' - O-MOE linkage; sub O linkage
<220> FEATURE:
<221> NAME/KEY: misc_feature
<222> LOCATION: (20)..(20)
<223> OTHER INFORMATION: 3' - O-MOE linkage

<400> SEQUENCE: 6
atgcattctg cccccaagga                                              20

<210> SEQ ID NO 7
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: 3' - O - MOE linkage
<220> FEATURE:
<221> NAME/KEY: misc_feature
<222> LOCATION: (20)..(20)
<223> OTHER INFORMATION: 3' - O - MOE linkage

<400> SEQUENCE: 7
atgcattctg cccccaagga                                              20
```

```
<210> SEQ ID NO 8
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: 3' - O-MOE linkage
<220> FEATURE:
<221> NAME/KEY: misc_feature
<222> LOCATION: (19)..(20)
<223> OTHER INFORMATION: 3' - O-MOE linkage

<400> SEQUENCE: 8
atgcattctg cccccaagga                                                 20

<210> SEQ ID NO 9
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: 3' - O-MOE linkage; sub O linkage
<220> FEATURE:
<221> NAME/KEY: misc_feature
<222> LOCATION: (18)..(19)
<223> OTHER INFORMATION: sub O linkage
<220> FEATURE:
<221> NAME/KEY: misc_feature
<222> LOCATION: (19)..(20)
<223> OTHER INFORMATION: 3' - O-MOE linkage; sub O linkage
<220> FEATURE:
<221> NAME/KEY: misc_feature
<222> LOCATION: (20)..(20)
<223> OTHER INFORMATION: 3' - O-MOE linkage

<400> SEQUENCE: 9
atgcattctg ccaaaaagga                                                 20

<210> SEQ ID NO 10
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: 3' - O-MOE linkage
<220> FEATURE:
<221> NAME/KEY: misc_feature
<222> LOCATION: (2)..(3)
<223> OTHER INFORMATION: 3' - O-MOE linkage
<220> FEATURE:
<221> NAME/KEY: misc_feature
<222> LOCATION: (19)..(20)
<223> OTHER INFORMATION: 3' - O-MOE linkage

<400> SEQUENCE: 10
atgcattctg ccaaaaagga                                                 20

<210> SEQ ID NO 11
<211> LENGTH: 20
<212> TYPE: DNA
```

```
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: 3' - O-MOE linkage; sub O linkage
<220> FEATURE:
<221> NAME/KEY: misc_feature
<222> LOCATION: (2)..(3)
<223> OTHER INFORMATION: 3' - O-MOE linkage; sub O linkage
<220> FEATURE:
<221> NAME/KEY: misc_feature
<222> LOCATION: (18)..(19)
<223> OTHER INFORMATION: sub O linkage
<220> FEATURE:
<221> NAME/KEY: misc_feature
<222> LOCATION: (19)..(20)
<223> OTHER INFORMATION: 3' - O-MOE linkage; sub O linkage
<220> FEATURE:
<221> NAME/KEY: misc_feature
<222> LOCATION: (20)..(20)
<223> OTHER INFORMATION: 3' - O-MOE linkage

<400> SEQUENCE: 11
atgcattctg ccaaaaagga                                              20

<210> SEQ ID NO 12
<211> LENGTH: 12
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(12)
<223> OTHER INFORMATION: 3' - O-MOE linkage

<400> SEQUENCE: 12
cgcgaattcg cg                                                      12

<210> SEQ ID NO 13
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 13
atgcattctg cccccaagga                                              20

<210> SEQ ID NO 14
<211> LENGTH: 11
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (6)..(7)
<223> OTHER INFORMATION: 2' aminolinker linkage

<400> SEQUENCE: 14
ggctguctgc g                                                       11

<210> SEQ ID NO 15
<211> LENGTH: 19
```

```
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (16)..(17)
<223> OTHER INFORMATION: 3' - O-MOE linkage
<220> FEATURE:
<221> NAME/KEY: misc_feature
<222> LOCATION: (17)..(18)
<223> OTHER INFORMATION: 3' - O-MOE linkage
<220> FEATURE:
<221> NAME/KEY: misc_feature
<222> LOCATION: (18)..(19)
<223> OTHER INFORMATION: 3' - O-MOE linkage

<400> SEQUENCE: 15
tttttttttt tttttttt                                                 19

<210> SEQ ID NO 16
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (16)..(17)
<223> OTHER INFORMATION: 2' - O-MOE linkage
<220> FEATURE:
<221> NAME/KEY: misc_feature
<222> LOCATION: (17)..(18)
<223> OTHER INFORMATION: 2' - O-MOE linkage
<220> FEATURE:
<221> NAME/KEY: misc_feature
<222> LOCATION: (18)..(19)
<223> OTHER INFORMATION: 2' - O-MOE linkage

<400> SEQUENCE: 16
tttttttttt tttttttu                                                 19

<210> SEQ ID NO 17
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (15)..(16)
<223> OTHER INFORMATION: sub O linkage
<220> FEATURE:
<221> NAME/KEY: misc_feature
<222> LOCATION: (16)..(17)
<223> OTHER INFORMATION: 3' - O-MOE linkage; sub O linkage
<220> FEATURE:
<221> NAME/KEY: misc_feature
<222> LOCATION: (17)..(18)
<223> OTHER INFORMATION: 3' - O-MOE linkage; sub O linkage
<220> FEATURE:
<221> NAME/KEY: misc_feature
<222> LOCATION: (18)..(19)
<223> OTHER INFORMATION: 3' - O-MOE linkage; sub O linkage
<220> FEATURE:
<221> NAME/KEY: misc_feature
<222> LOCATION: (19)..(19)
<223> OTHER INFORMATION: 3' - O-MOE linkage

<400> SEQUENCE: 17
tttttttttt tttttttt                                                 19
```

<210> SEQ ID NO 18
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (15)..(16)
<223> OTHER INFORMATION: sub O linkage
<220> FEATURE:
<221> NAME/KEY: misc_feature
<222> LOCATION: (16)..(17)
<223> OTHER INFORMATION: 2' - O-MOE; sub O linkage
<220> FEATURE:
<221> NAME/KEY: misc_feature
<222> LOCATION: (17)..(18)
<223> OTHER INFORMATION: 2' - O-MOE; sub O linkage
<220> FEATURE:
<221> NAME/KEY: misc_feature
<222> LOCATION: (18)..(19)
<223> OTHER INFORMATION: 2' - O-MOE; sub O linkage
<220> FEATURE:
<221> NAME/KEY: misc_feature
<222> LOCATION: (19)..(19)
<223> OTHER INFORMATION: 2' - O-MOE

<400> SEQUENCE: 18
tttttttttt tttttttttu                                             19

<210> SEQ ID NO 19
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: 3' - aminopropyl-A linkage
<220> FEATURE:
<221> NAME/KEY: misc_feature
<222> LOCATION: (20)..(20)
<223> OTHER INFORMATION: 3' - aminopropyl-A linkage

<400> SEQUENCE: 19
atgcattctg cccccaagga                                             20

<210> SEQ ID NO 20
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: 3'-aminopropyl-A linkage; sub O linkage
<220> FEATURE:
<221> NAME/KEY: misc_feature
<222> LOCATION: (2)..(5)
<223> OTHER INFORMATION: sub O linkage
<220> FEATURE:
<221> NAME/KEY: misc_feature
<222> LOCATION: (5)..(16)
<223> OTHER INFORMATION: sub S linkage
<220> FEATURE:
<221> NAME/KEY: misc_feature
<222> LOCATION: (16)..(20)
<223> OTHER INFORMATION: sub O linkage

```
<220> FEATURE:
<221> NAME/KEY: misc_feature
<222> LOCATION: (20)..(20)
<223> OTHER INFORMATION: 3'-aminopropyl-A linkage

<400> SEQUENCE: 20
atgcattctg cccccaagga                                                    20

<210> SEQ ID NO 21
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (19)..(20)
<223> OTHER INFORMATION: Bis-2'-OME-MMI,2'-H linkage

<400> SEQUENCE: 21
tgcatccccc aggccaccat                                                    20

<210> SEQ ID NO 22
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: Bis-2'-OME-MMI,2'-H linkage
<220> FEATURE:
<221> NAME/KEY: misc_feature
<222> LOCATION: (19)..(20)
<223> OTHER INFORMATION: Bis-2'-OME-MMI,2'-H linkage

<400> SEQUENCE: 22
tgcatccccc aggccaccat                                                    20

<210> SEQ ID NO 23
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 23
tgcatccccc aggcgaccat                                                    20

<210> SEQ ID NO 24
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(4)
<223> OTHER INFORMATION: sub S linkage
<220> FEATURE:
<221> NAME/KEY: misc_feature
<222> LOCATION: (4)..(5)
<223> OTHER INFORMATION: 5-methyl-C; sub S linkage
<220> FEATURE:
<221> NAME/KEY: misc_feature
<222> LOCATION: (5)..(8)
```

```
<223> OTHER INFORMATION: sub S linkage
<220> FEATURE:
<221> NAME/KEY: misc_feature
<222> LOCATION: (8)..(9)
<223> OTHER INFORMATION: sub S linkage; 5-methyl-C
<220> FEATURE:
<221> NAME/KEY: misc_feature
<222> LOCATION: (10)..(11)
<223> OTHER INFORMATION: sub S linkage
<220> FEATURE:
<221> NAME/KEY: misc_feature
<222> LOCATION: (11)..(14)
<223> OTHER INFORMATION: sub S linkage; 5-methyl-C
<220> FEATURE:
<221> NAME/KEY: misc_feature
<222> LOCATION: (14)..(15)
<223> OTHER INFORMATION: 5-methyl-C; sub S linkage
<220> FEATURE:
<221> NAME/KEY: misc_feature
<222> LOCATION: (17)..(20)
<223> OTHER INFORMATION: sub S linkage

<400> SEQUENCE: 24
atgcattctg cccccaagga                                              20

<210> SEQ ID NO 25
<211> LENGTH: 24
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: sub S linkage
<220> FEATURE:
<221> NAME/KEY: misc_feature
<222> LOCATION: (2)..(3)
<223> OTHER INFORMATION: 5-methyl-C; sub S linkage
<220> FEATURE:
<221> NAME/KEY: misc_feature
<222> LOCATION: (3)..(5)
<223> OTHER INFORMATION: 5-methyl-C; sub S linkage
<220> FEATURE:
<221> NAME/KEY: misc_feature
<222> LOCATION: (5)..(8)
<223> OTHER INFORMATION: sub S linkage
<220> FEATURE:
<221> NAME/KEY: misc_feature
<222> LOCATION: (8)..(9)
<223> OTHER INFORMATION: 5-methyl-C; sub S linkage
<220> FEATURE:
<221> NAME/KEY: misc_feature
<222> LOCATION: (9)..(12)
<223> OTHER INFORMATION: sub S linkage
<220> FEATURE:
<221> NAME/KEY: misc_feature
<222> LOCATION: (12)..(13)
<223> OTHER INFORMATION: 5-methyl-C; sub S linkage
<220> FEATURE:
<221> NAME/KEY: misc_feature
<222> LOCATION: (15)..(16)
<223> OTHER INFORMATION: sub S linkage
<220> FEATURE:
<221> NAME/KEY: misc_feature
<222> LOCATION: (16)..(17)
<223> OTHER INFORMATION: 5-methyl-C
<220> FEATURE:
<221> NAME/KEY: misc_feature
<222> LOCATION: (18)..(19)
<223> OTHER INFORMATION: 5-methyl-C; sub S linkage
<220> FEATURE:
<221> NAME/KEY: misc_feature
<222> LOCATION: (21)..(22)
<223> OTHER INFORMATION: sub S linkage
<220> FEATURE:
```

```
<221> NAME/KEY: misc_feature
<222> LOCATION: (22)..(23)
<223> OTHER INFORMATION: 5-methyl-C

<400> SEQUENCE: 25
gcccaagctg gcastcscgs tcsa                                              24

<210> SEQ ID NO 26
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (16)..(17)
<223> OTHER INFORMATION: 2'-modified T linkage
<220> FEATURE:
<221> NAME/KEY: misc_feature
<222> LOCATION: (17)..(18)
<223> OTHER INFORMATION: 2'-modified T linkage
<220> FEATURE:
<221> NAME/KEY: misc_feature
<222> LOCATION: (18)..(19)
<223> OTHER INFORMATION: 2'-modified T linkage
<220> FEATURE:
<221> NAME/KEY: misc_feature
<222> LOCATION: (19)..(19)
<223> OTHER INFORMATION: 2'-modified T linkage

<400> SEQUENCE: 26
tttttttttt ttttttttt                                                   19

<210> SEQ ID NO 27
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(20)
<223> OTHER INFORMATION: sub S linkage

<400> SEQUENCE: 27
tccgtcatcg ctcctcaggg                                                  20

<210> SEQ ID NO 28
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(20)
<223> OTHER INFORMATION: sub S linkage

<400> SEQUENCE: 28
tcagtaatag gcccacatgg                                                  20

<210> SEQ ID NO 29
<211> LENGTH: 20
<212> TYPE: DNA
<213> ORGANISM: Artificial Sequence
<220> FEATURE:
<221> NAME/KEY: misc_feature
<223> OTHER INFORMATION: Oligonucleotide
```

```
<220> FEATURE:
<221> NAME/KEY: misc_feature
<222> LOCATION: (1)..(4)
<223> OTHER INFORMATION: sub O linkage
<220> FEATURE:
<221> NAME/KEY: misc_feature
<222> LOCATION: (4)..(13)
<223> OTHER INFORMATION: sub S linkage
<220> FEATURE:
<221> NAME/KEY: misc_feature
<222> LOCATION: (13)..(20)
<223> OTHER INFORMATION: sub O linkage

<400> SEQUENCE: 29
ttcgtcatcg ctcctcaggg                                              20

<210> SEQ ID NO 30
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide

<400> SEQUENCE: 30
atgcattctg ccccaagga                                               19

<210> SEQ ID NO 31
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(5)
<223> OTHER INFORMATION: sub O linkage
<220> FEATURE:
<221> NAME/KEY: misc_feature
<222> LOCATION: (5)..(15)
<223> OTHER INFORMATION: sub S linkage
<220> FEATURE:
<221> NAME/KEY: misc_feature
<222> LOCATION: (15)..(19)
<223> OTHER INFORMATION: sub O linkage

<400> SEQUENCE: 31
atgcattctg ccccaagga                                               19

<210> SEQ ID NO 32
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(19)
<223> OTHER INFORMATION: sub S linkage

<400> SEQUENCE: 32
atgcattctg ccccaagga                                               19

<210> SEQ ID NO 33
<211> LENGTH: 19
<212> TYPE: DNA
<213> ORGANISM: Artificial Sequence
<220> FEATURE:
<221> NAME/KEY: misc_feature
```

-continued

```
<223> OTHER INFORMATION: Oligonucleotide
<220> FEATURE:
<221> NAME/KEY: misc_feature
<222> LOCATION: (1)..(2)
<223> OTHER INFORMATION: sub O linkage; 3' - O-MOE linkage
<220> FEATURE:
<221> NAME/KEY: misc_feature
<222> LOCATION: (2)..(5)
<223> OTHER INFORMATION: sub O linkage
<220> FEATURE:
<221> NAME/KEY: misc_feature
<222> LOCATION: (5)..(15)
<223> OTHER INFORMATION: sub S linkage
<220> FEATURE:
<221> NAME/KEY: misc_feature
<222> LOCATION: (15)..(19)
<223> OTHER INFORMATION: sub O linkage

<400> SEQUENCE: 33
atgcattctg ccccaagga                                                  19

<210> SEQ ID NO 34
<211> LENGTH: 19
<212> TYPE: DNA
<213> ORGANISM: Artificial Sequence
<220> FEATURE:
<221> NAME/KEY: misc_feature
<223> OTHER INFORMATION: Oligonucleotide
<220> FEATURE:
<221> NAME/KEY: misc_feature
<222> LOCATION: (1)..(2)
<223> OTHER INFORMATION: sub S linkage; 3' - O-MOE linkage
<220> FEATURE:
<221> NAME/KEY: misc_feature
<222> LOCATION: (2)..(18)
<223> OTHER INFORMATION: sub S linkage
<220> FEATURE:
<221> NAME/KEY: misc_feature
<222> LOCATION: (18)..(19)
<223> OTHER INFORMATION: sub S linkage; 3' - O-MOE linkage

<400> SEQUENCE: 34
atgcattctg ccccaagga                                                  19
```